US012037630B2

(12) United States Patent
Moseley et al.

(10) Patent No.: US 12,037,630 B2
(45) Date of Patent: Jul. 16, 2024

(54) **PRODUCTION OF LIPIDS AND TERPENOIDS IN *AUXENOCHLORELLA PROTOTHECOIDES***

(71) Applicants: PHYCOIL BIOTECHNOLOGY INTERNATIONAL, INC., Fremont, CA (US); PHYCOILBIOTECH KOREA, Inc., Seoul (KR)

(72) Inventors: Jeffrey Moseley, Fremont, CA (US); Byung-Hee Lee, Seoul (KR); Chung Soon Im, Seoul (KR); Jane Kim, Fremont, CA (US); Dayoung Kim, Seoul (KR); Riyaz Bhat, Fremont, CA (US)

(73) Assignees: Phycoil Biotechnology International, Inc., Fremont, CA (US); Phycoilbiotech Korea, Inc.

(*) Notice: Subject to any disclaimer, the term of this patent is extended or adjusted under 35 U.S.C. 154(b) by 316 days.

(21) Appl. No.: 17/519,854

(22) Filed: Nov. 5, 2021

(65) Prior Publication Data

US 2022/0154229 A1 May 19, 2022

Related U.S. Application Data

(60) Provisional application No. 63/109,901, filed on Nov. 5, 2020.

(51) Int. Cl.

| | |
|---|---|
| ***C12N 15/52*** | (2006.01) |
| ***C12N 9/02*** | (2006.01) |
| ***C12N 9/16*** | (2006.01) |
| ***C12N 9/90*** | (2006.01) |
| ***C12P 7/6472*** | (2022.01) |

(52) U.S. Cl.

CPC .......... *C12P 7/6472* (2013.01); *C12N 9/0071* (2013.01); *C12N 9/0083* (2013.01); *C12N 9/16* (2013.01); *C12N 9/90* (2013.01); *C12N 15/52* (2013.01); *C12Y 114/19* (2013.01); *C12Y 114/19002* (2013.01); *C12Y 301/02014* (2013.01); *C12Y 505/01018* (2013.01)

(58) Field of Classification Search

CPC ............. C12N 15/52; C12N 9/16; C12N 9/90

See application file for complete search history.

(56) References Cited

U.S. PATENT DOCUMENTS

2011/0293785 A1* 12/2011 Franklin .................. A23D 7/00 426/61

OTHER PUBLICATIONS

Akihiro Aioi et al., "Effect of squalene on superoxide anion generation induced by a skin irritant, lauroylsarcosine", International Journal of Pharmaceutics 113 (1995) 159-164.

Ryszard Amarowicz, "Squalene: A natural antioxidant?", Eur. J. Lipid Sci. Technol. 2009, 111, 411-412, DOI 10.1002/ejlt.200900102.

Ramesh Bhujade et al., "Algae to Economically Viable Low-Carbon-Footprint Oil", Annu. Rev. Chem. Biomol. Eng. 2017. 8:335-57, https://doi.org/10.1146/annurev-chembioeng-060816-101630.

Arief Budiyanto et al., "Protective effect of topically applied olive oil against photocarcinogenesis following UVB exposure of mice", Carcinogenesis, vol. 21, Issue 11, Nov. 1, 2000, pp. 2085-2090, https://doi.org/10.1093/carcin/21.11.2085.

Sylwester Czaplicki et al., "Characteristics of Biologically-Active Substances of Amaranth Oil Obtained by Various Techniques", Pol. J. Food Nutr Sei., 2012, vol. 62, No. 4, pp. 235-239, DOI: 10.2478/V10222-012-0054-8.

Giuseppe Del Giudice et al., "Vaccines with the MF59 Adjuvant Do Not Stimulate Antibody Responses against Squalene", Clin Vaccine Immunol. Sep. 2006;13(9):1010-3. doi: 10.1128/CVI.00191-06.

H.A.M. Elwan et al., "Red yeast (*Phaffia rhodozyma*) as a source of Astaxanthin and its impacts on productive performance and physiological responses of poultry", World's Poultry Science Journal, vol. 75, Jun. 2019.

Fatma Esra Güneş, "Medical Use of Squalene as a Natural Antioxidant", Journal of Marmara University Institute of Health Sciences, Jan. 2013.

Zih-Rou Huang et al., "Biological and Pharmacological Activities of Squalene and Related Compounds: Potential Uses in Cosmetic Dermatology", Molecules 2009, 14, 540-554, Jan. 23, 2009; doi: 10.3390/molecules14010540.

Slavyana Ivanova et al., "Surface Properties of Squalene/Meibum Films and NMR Confirmation of Squalene in Tears", Int. J. Mol. Sci. 2015, 16, 21813-21831, Sep. 9, 2015; doi:10.3390/ijms160921813.

Se-Kwon Kim et al., "Biological importance and applications of squalene and squalane", Adv Food Nutr Res . 2012;65:223-33. doi: 10.1016/B978-0-12-416003-3.00014-7.

Zdenka Kopicová et al., "Occurrence of Squalene and Cholesterol in Various Species of Czech Freshwater Fish", Czech J. Food Sci., vol. 25, No. 4: 195-201.

Yousry M. A. Naguib, "Antioxidant Activities of Astaxanthin and Related Carotenoids", J. Agric. Food Chem., vol. 48, No. 4, 2000.

N. Nicolaides, "Skin Lipids: Their Biochemical Uniqueness", Science, vol. 186, Oct. 4, 1974.

Alberta Di Pasquale et al., "Vaccine Adjuvants: from 1920 to 2015 and Beyond", Vaccines 2015, 3, 320-343, Apr. 16, 2015; doi:10.3390/vaccines3020320.

Ovidiu Popa et al., "Methods for Obtaining and Determination of Squalene from Natural Sources", Hindawi Publishing Corporation, BioMed Research International, vol. 2015, Article ID 367202, 16 pages, http://dx.doi.org/10.1155/2015/367202.

(Continued)

*Primary Examiner* — Tekchand Saidha
(74) *Attorney, Agent, or Firm* — HelixIP LLP

(57) ABSTRACT

Methods to produce oils with modified profiles of fatty acid, carotenoids and/or terpenoids in microalgal mutants are provided. Microalgal mutants produce the oil containing fatty acids, carotenoids and/or terpenoids of a modified profile with a disruption or ablation of one or more alleles of an endogenous polynucleotide or comprising an exogeneous gene are also provided.

12 Claims, 36 Drawing Sheets

Specification includes a Sequence Listing.

(56) References Cited

OTHER PUBLICATIONS

Teresa Rosales-García et al., "Squalene Extraction: Biological Sources and Extraction Methods.", International Journal of Environment, Agriculture and Biotechnology (IJEAB), vol. 2, Issue-4, Jul.-Aug. 2017; http://dx.doi.org/10.22161/ijeab/2.4.26.

Isabell Schmidt et al., "Biotechnological production of astaxanthin with Phaffia rhodozyma/Xanthophyllomyces dendrorhous", Appl Microbiol Biotechnol (2011) 89:555-571, DOI 10.1007/s00253-010-2976-6.

Colin Ratledge, "Single Cell Oils for the 21st Century", Department of Biological Sciences, University of Hull.

Theresa J Smith, "Squalene: potential chemopreventive agent", Expert Opinion on Investigational Drugs (2009) 9(8):1841-1848.

Yibo Xiao et al., "Industrial Fermentation of Auxenochlorella protothecoides for Production of Biodiesel and Its Application in Vehicle Diesel Engines", Front Bioeng Biotechnol. Oct. 19, 2015;3:164. doi: 10.3389/fbioe.2015.00164. eCollection 2015.

George G. Zaimes et al., "Environmental Sustainability of Emerging Algal Biofuels: A Comparative Life Cycle Evaluation of Algal Biodiesel and Renewable Diesel", Environmental Progress & Sustainable Energy, vol. 32, No. 4, Jul. 19, 2013.

* cited by examiner

【FIG. 1】
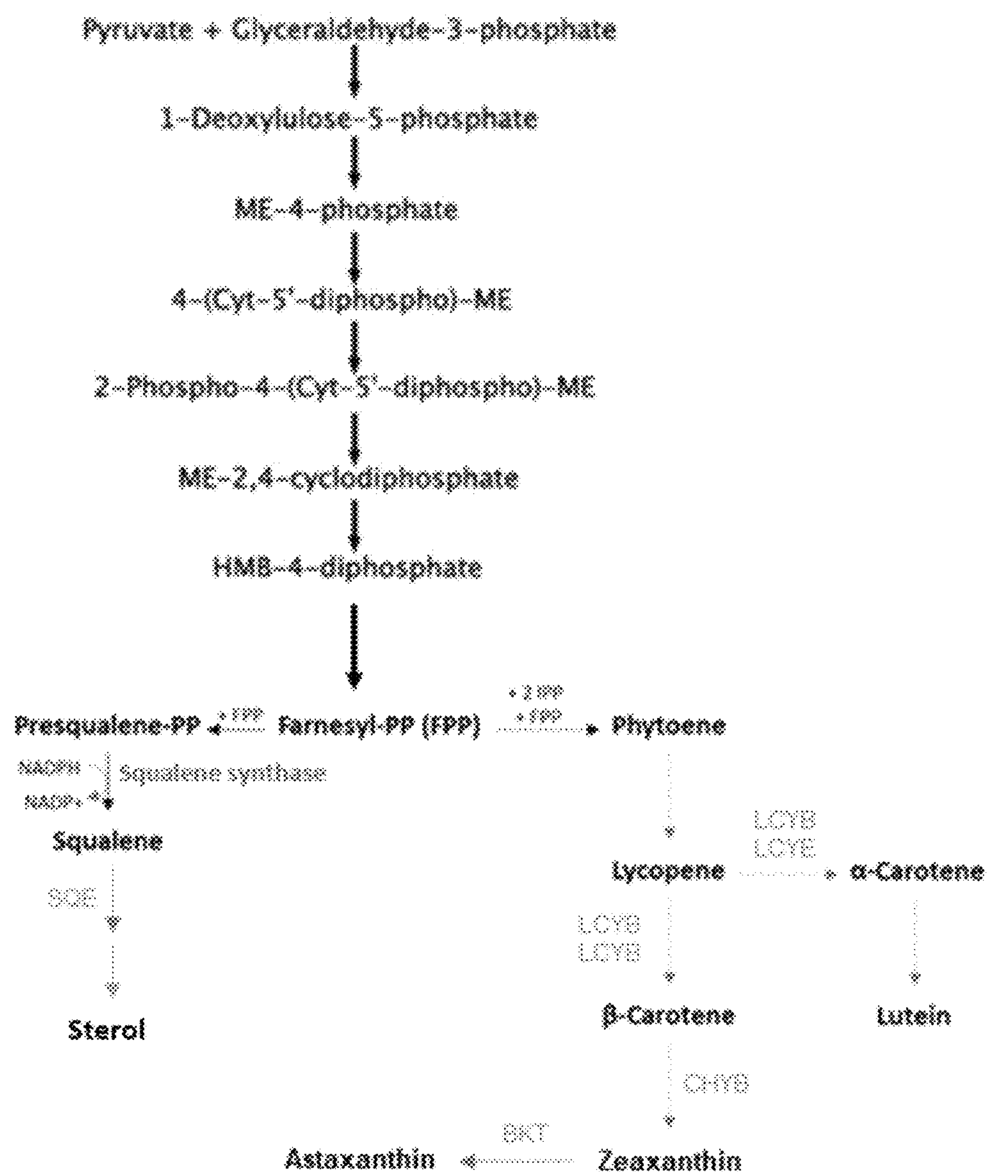

【FIG. 2A】 aagcttCAAGTGCGTGCGTTACAGTGTTACCAACAACAGTCTAACCTACCCCTTTCGGTCATTCTGC

CCTTTGGCAAGAGTTCAGAATGAAGTGTGCTTGCACATCGAGCTAGTGCTGTGAGCGAAGACAA

GGAAGTCCCCACTCACCCACGTGGCCAGATTCTATCTTTTTTCAGATTGCAAGGGCCACGCCCAG

CGAACCCCGCGATGGGGCCGAGCCATGCCCGACATCTCGACATCTTCATATGATAAGGCGCTTCA

AAGTGCAATTTTTGTGCATGGCATCAATTAGGAGAGTGCTTGAACACCAGCCCATCTTCCACCGG

GGAAGGACCGTCGAAATGCCTCTGCAGACGGCCACCGTCTGATCGCTGCCTGTCCCGAGGTGA

CGGCGATGTCGTCCTTATCCCAAACAATCGTTCGAAGACCTTTCTTTTGTTCGCTCAACCCACCG

AGGAGACCGTCTGGATTCCATGCTGCTGTGACGCCTAGCCCCCTGAGACCCTCCAAGTGGGCG

GTCCCCTCCCTAGCCCCCAGCCTCTCTGACGTGGCAGATGCCTCCGCGGAAGCAAATCAGGATC

GCAGGGAGGGCTCCTACGAGCAGCCCCTGGTCCAACGCCAGGTGCCTAGGGGGAAAGGAGGG

CAGAGGGGCTTGAGGCGAGCCTGGCCCAGGCAGGGCTTCCATGGTCAGTCGTGGCAGTGCCAT

GACAGCCGAAGCCCAACGCGACACCGTGGGTGCAGCATGCGTGGACGGAAACATTGGCAATGC

CTTGCCCCATTGGCCCCCCAGGCCCGGAAACGGGACGATCAGCAGGACCCCTTGTCCAGCCTC

CTCCCCACggtaccctttcttgcgctatgacacttccagcaaaaggtagggcgggctgcgagacggcttcccggcgctgcatgcaaca ccgatgatgcttcgacccccccgaagctccttcggggctgcatgggcgctccgatgccgctccagggcgagcgctgtttaaatagccaggccc ccgattgcaaagacattatagcgagctaccaaagccatattcaaacacctagatcactaccacttctacacaggccactcgagcttgtgatcg cactccgctaagggggcgcctcttcctcttcgtttcagtcacaacccgcaaac*ATGctgctgcaggccttcctgttcctgctggccggcttcgcc*

*gccaagatcagcgcctccatgacgaacgagacgtccgaccgccccctggtgcacttcacccccaacaagggctggatgaacgaccccaa*

*cggcctgtggtacgacgagaaggacgccaagtggcacctgtacttccagtacaacccgaacgacaccgtctgggggacgcccttgttctgg*

*ggccacgccacgtccgacgacctgaccaactgggaggaccagcccatcgccatcgccccgaagcgcaacgactccggcgccttctccgg*

*ctccatggtggtggactacaacaacacctccggcttcttcaacgacaccatcgacccgcgccagcgctgcgtggccatctggacctacaaca*

*ccccggagtccgaggagcagtacatctcctacagcctggacggcggctacaccttcaccgagtaccagaagaaccccgtgctggccgcca*

*actccacccagttccgcgacccgaaggtcttctggtacgagccctcccagaagtggatcatgaccgcggccaagtcccaggactacaagat*

*cgagatctactcctccgacgacctgaagtcctggaagctggagtccgcgttcgccaacgagggcttcctcggctaccagtacgagtgccccg*

*gcctgatcgaggtccccaccgagcaggaccccagcaagtcctactgggtgatgttcatctccatcaaccccggcgccccggccggcggctc*

*cttcaaccagtacttcgtcggcagcttcaacggcacccacttcgaggccttcgacaaccagtcccgcgtggtggacttcggcaaggactacta*

*cgccctgcagaccttcttcaacaccgacccgacctacgggagcgccctgggcatcgcgtgggcctccaactgggagtactccgccttcgtgc*

【FIG. 2B】

*ccaccaacccctggcgctcctccatgtccctcgtgcgcaagttctccctcaacaccgagtaccaggccaacccggagacggagctgatcaa*
*cctgaaggccgagccgatcctgaacatcagcaacgccggcccctggagccggttcgccaccaacaccacgttgacgaaggccaacagct*
*acaacgtcgacctgtccaacagcaccggcaccctggagttcgagctggtgtacgccgtcaacaccacccagacgatctccaagtccgtgttc*
*gcggacctctccctctggttcaagggcctggaggaccccgaggagtacctccgcatgggcttcgaggtgtccgcgtcctccttcttcctggacc*
*gcgggaacagcaaggtgaagttcgtgaaggagaacccctacttcaccaaccgcatgagcgtgaacaaccagcccttcaagagcgagaa*
*cgacctgtcctactacaaggtgtacggcttgctggaccagaacatcctggagctgtacttcaacgacggcgacgtcgtgtccaccaacaccta*
*cttcatgaccaccgggaacgccctgggctccgtgaacatgacgacgggggtggacaacctgttctacatcgacaagttccaggtgcgcgag*
*gtcaagTGA*TTGATTGGAACTCACAAAGCGGCCCACGGCTTCGAACGTCCCGTGTCAATTGCGCGGGGTGTGCCAGA
GTTTCTGCGCCACCGATGCTCACCCTAGGGGGGGATGCCCTTTGACATTCATGTGTGCCTGCATGCACGTTTGTATCA
GTCTCACCACACCTTGAAGATTTTTGGGAGGGGGGGGGAAGTCGGAATGGAAACgagctcCGCGATTGTCAGAT
GGTGGAGTGGGTGGATGGCCCTGCTCCGAGGAGCTTTCTAGGGCGCGAACTTGGCCCTTCTCC
CCTCTGATGCAGTGTGGGGGGACGCGGTGTGCTATTTCTCCGAGGGCCGCCCAACTAGGGTGG
GGCGGGCATACGCCCGCGTCGACAGGTGGGTGTGGCCTCGAGGTGTTGAGAGGAGTGTTATGT
CGACAGCCAAAGTGGAGACTGATTGAACCCTACTCCAGGTGCTATCTTGGGAGCACACTGCGCC
CACCGTGGCTGGACTGCCCGAATTCCAACCTTGGTGCCCAGAAACAGGGCAAAGCCGGTCATC
AGTGCAGCATGAGACTCAAGCTCCCTAGCTCATGACCGTTGGCATAGGCAGAAGCTGCGGCAGC
ACCTGGTGGAGGCCTGCCAGGCAAACGGTGTCACCTTCCAGCCGGGGGAGGTAGTGGATGTGG
GCGTGAAGAACGGCACAGCCTCGGTCACCTGCCAAGATGGCTCCGTCCTGACTGCGAGGTGGG
CGCTGTGCATGGCATTTGTTGGCACGAGTCTGCATCTCTGAAGCTGCTGGGTAGCGTCAGAGCA
GTGGAGTCAACAGCACACAGCTCTGGCGGTGCTCAGGGAACATACATCGCACTGTTTCCTGGAG
TTGCTGGCCCTCTGTGGGGCAACCAGGACCCCCCGACGCATGCATGCCCCCTCGCACATCCCG
CACAGGCTGGTGACCCTGGCCTCCGGCGCGGCGGCGGGGCGCTTCCTCAAGTACGAGAGaagc
tt

【FIG. 3A】 aagcttCAAGTGCGTGCGTTACAGTGTTACCAACAACAGTCCAACCTAACCCTTTCGGTCATTCTGT
CCTTTGGCAAGGGCTCAGAATGAAGTGTGCCTGCACATCGAGCTAGTGCTGTGAGCGAAGACAA
GGAAGTCCCCACTCACCCACGTGGCCAGATTTTATCTTTTTTCAGATTGCAAGGGCCACGCCCAG
CGAACCCCGCGATGGGGCCGAGCCATGCCCGACATCTCGACATCTTCATATGACAAGGCGCTTC
AAAGTGCAATTTATGTGCATGGCATCGATTAGGAGAGTGGTTGAACACCAGCCCATCTTCCACCG
GGGAAGGACCGTCGAAATGCCTCTGCAGACGGCCACCGTCTGATCGCTGCCTGTCCCGAGGTG
ACGGCGATGTCGTCCTTATCCCAAACAATCGTTCGAAGACCTTTCTTTTGTTCGCTCAACCCACC
GAGGAGACCGTCTGGATTCCATGCCGCTGTGACGCCTAGCCCCCTGAGACCCTCCAAGTGGGC
GGTCCCCTCCCTAGCCCCCAGCCTCTCTGACGTGGCAGATGCCTCCGCGGAAGCAAATCAGGAT
CGCAGGGAGGGCTCCTACGAGCAGCCCCTGGTCCAACGCCAGGTGCCTAGGGGGAAAGGAGG
GCAGGGGGCCTTGAGGCGAGCCTGGCCCAGGCAGGGCTTCCATGGTCAGTCGTGGCAGTGCC
ATGACAGCCGAAGCCCACCGCGACACCGTGGGTGCAGCATGCGTGGACGGAAACATTGGCAAT
GCCTTGCCCCATTGGACCCCCAGGCCCGGAAACGGGACGATCAGCAGGACCCCCTGTCCAGCC
TCCTCCCCACggtacccccgcttttaattgagccccttcgtcgctgaatcagcgaaagcaccgcgaaacaatgcctgtcccgtccat
gcatctcaacagcctcatgcaaggtttgcacaagcaagaccattctgatctgggaacttgtaggtgttgtatgggggaggttgtgctcttgaatca
agtggtatcacgtttccggaacaccccgaaacgtgcatgggcttattgcgatgagagcatttcccaccgcgattgtctcacgcgcatttcggag
aaggtttgcagaacactccaggacatgaaatgccttgtcacgtatgaaccatctcccacggccttgaaaagatcgctcgacttccattctagat
ggtgcaaaaccctacgactcaagaaggtgccaccgactcaggcattgggcacggcgggcagggagaagagaggagttgatcaaaactg
ctcgatcacgttcccccatggcgatccgagcagcacatgatgcatcgaggtggcgccgttgcaaaggagttgcgcatgggtcgaagcaggg
agaaggaaacggcgaggcgtgccgcgggggtgaattcagagtcaaatctgcgcctgccccggcgctcctgacggggattaacccccacg
actgtatccatcgacactcgtctcgggggaataaaagcggcgacccagctccagaggcgcaatccttctcacaatctgtttaactttcaacaaa
gtataagtcaattcaacttgacaca*ATGgccgcgtccgtccactgcaccctgatgtccgtggtctgcaacaacaagaaccactccgcccgcc*
*ccaagctgcccaactcctccctgctgcccggcttcgacgtggtggtccaggccgcggccacccgcttcaagaaggagacgacgaccaccc*
*gcgccacgctgacgttcgacccccccacgaccaactccgagcgcgccaagcagcgcaagcacaccatcgacccctcctcccccgacttcc*
*agcccatcccctccttcgaggagtgcttccccaagtccacgaaggagcacaaggaggtggtgcacgaggagtccggccacgtcctgaagg*
*tgcccttccgccgcgtgcacctgtccggcggcgagcccgccttcgacaactacgacacgtccggcccccagaacgtcaacgcccacatcgg*
*cctggcgaagctgcgcaaggagtggatcgaccgccgcgagaagctgggcacgccccgctacacgcagatgtactacgcgaagcagggc*
*atcatcacggaggagatgctgtactgcgcgacgcgcgagaagctggaccccgagttcgtccgctccgaggtcgcgcggggccgcgccatc*

【FIG. 3B】

*atcccctccaacaagaagcacctggagctggagcccatgatcgtgggccgcaagttcctggtgaaggtgaacgcgaacatcggcaactcc*
*gccgtggcctcctccatcgaggaggaggtctacaaggtgcagtgggccaccatgtggggcgccgacaccatcatggacctgtccacgggc*
*cgccacatccacgagacgcgcgagtggatcctgcgcaactccgcggtccccgtgggcaccgtccccatctaccaggcgctggagaaggtg*
*gacggcatcgcggagaacctgaactgggaggtgttccgcgagacgctgatcgagcaggccgagcagggcgtggactacttcacgatcca*
*cgcgggcgtgctgctgcgctacatcccccctgaccgccaagcgcctgacgggcatcgtgtcccgcggcggctccatccacgcgaagtggtgc*
*ctggcctaccacaaggagaacttcgcctacgagcactgggacgacatcctggacatctgcaaccagtacgacgtcgccctgtccatcggcg*
*acggcctgcgccccggctccatctacgacgccaacgacacggcccagttcgccgagctgctgacccagggcgagctgacgcgccgcgcg*
*tgggagaaggacgtgcaggtgatgaacgagggccccggccacgtgcccatgcacaagatccccgagaacatgcagaagcagctggagt*
*ggtgcaacgaggcgcccttctacaccctgggccccctgacgaccgacatcgcgcccggctacgaccacatcacctccgccatcggcgcgg*
*ccaacatcggcgccctgggcaccgccctgctgtgctacgtgacgcccaaggagcacctgggcctgcccaaccgcgacgacgtgaaggcg*
*ggcgtcatcgcctacaagatcgccgcccacgcggccgacctggccaagcagcacccccacgcccaggcgtgggacgacgcgctgtcca*
*aggcgcgcttcgagttccgctggatggaccagttcgcgctgtccctggaccccatgacggcgatgtccttccacgacgagacgctgcccgcg*
*gacggcgcgaaggtcgcccacttctgctccatgtgcggccccaagttctgctccatgaagatcacggaggacatccgcaagtacgccgagg*
*agaacggctacggctccgccgaggaggccatccgccagggcatggacgccatgtccgaggagttcaacatcgccaagaagacgatctcc*
*ggcgagcagcacggcgaggtcggcggcgagatctacctgcccgagtcctacgtcaaggccgcgcagaagTGA*GTCCTGGCGACC
CTGCTCCCCTGACCCCTGTTCCCCTGCGCTGCTTCTCCCCGGTGACATCCGACCTGCTGCAAAATTCCCGTTCCTGC
ACAACACTTGCCTGACCGAGGGTCGGGTCGCGAAGTAAAAGCCACAATCAACACCCCAGGCACATTAAGAGTGCACA
GCATGACGCAGCATAGGGTTTGTGTCGGAGGAAGGGGGTCGAGTCGCGTTGGCGAGGGGGTGGTCACGATGACCA
CATCTGCGGGATAATTGAATCCTCAGGGGAAAATACCAGTCTCTGCTTCCAGGTGCTCCGgagctcCGCGATTGTC
AGATGGTGGAGTGGGTGGATGGCCCTGCTCCAGAGGAGCGTTCTAGGGCGCAAACTTGGCACT
TTCCCCCCTCTGATGCAGTGTGGGGGGACGCGGTGTGCTATTTCTCCGAGGGCCGCCCAACCA
GGGTGGGGCGGGCATATGCCCGCGTCGACAGGTGGGTGTGGCCTCGAGGTGTTGAGAGGAGG
GTTATGTCGACAGCCAAAGTGGAGACTGAGTGAACCCTACTCCAGGTGCTGTCGTGGGAGCGCA
CTGCGCCCACCGTGGCTGGACTGCTCGTATTCCAACCTTGGTGCCCAGAAACAGGGCAAAGCC
GGTCATCAGTGCAGCATGAGACTCAAGCTCCCTAACTCATGACCGTTGGCATAGGCAGAAGCTG
CGGCAGCACCTGGTGGAGGCCTGCCAGGCAAACGGTGTCACCTTCCAGCCGGGGGAGGTAGT
GGATGTGGGCGTGAAGAACGGCACAGCCTCGGTCACCTGCCGAGACGGCTCCGTCCTGACTGC
GAGGTGGGCGCTGTGCATGGCACTTGTTGGCACGAGTCTGCATCCCTGAAGCTGCTGGGTAGC
GTCAGAGCAGTGGCGTCAACAGCACACAGCTCTGGCGGTGCCCAGGGAACATACATCGCTCTG 【FIG. 3C】
<u>TTTCCTGGAGTTGCGGGCCCTCTGTGTGGCAGCCAGGGCCCCCCGACGCATGCATGCCTCCTC
GCACATCCCGCACAGGCTGGTGACCCTGGCCTCCGGCGCGGCGGCGGGGCGCTTCCTCAAGT
ACGAGAG</u>aagctt
【FIG. 4A】
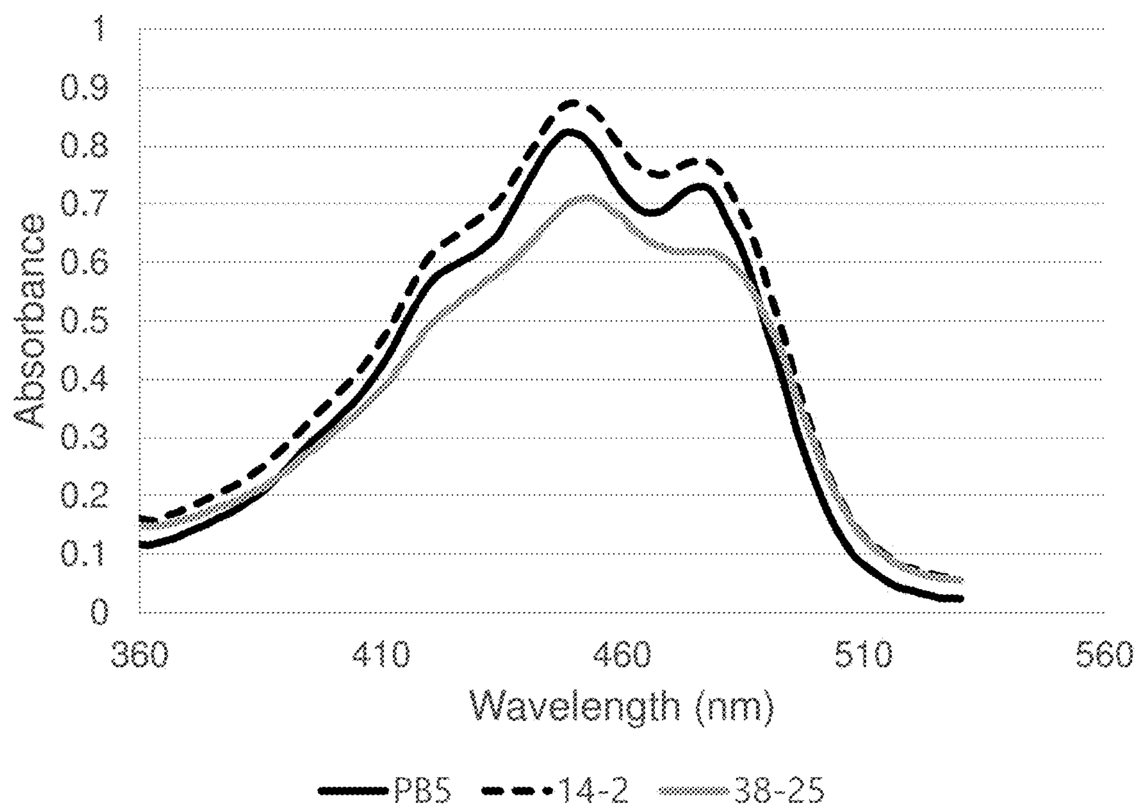

【FIG. 4B】
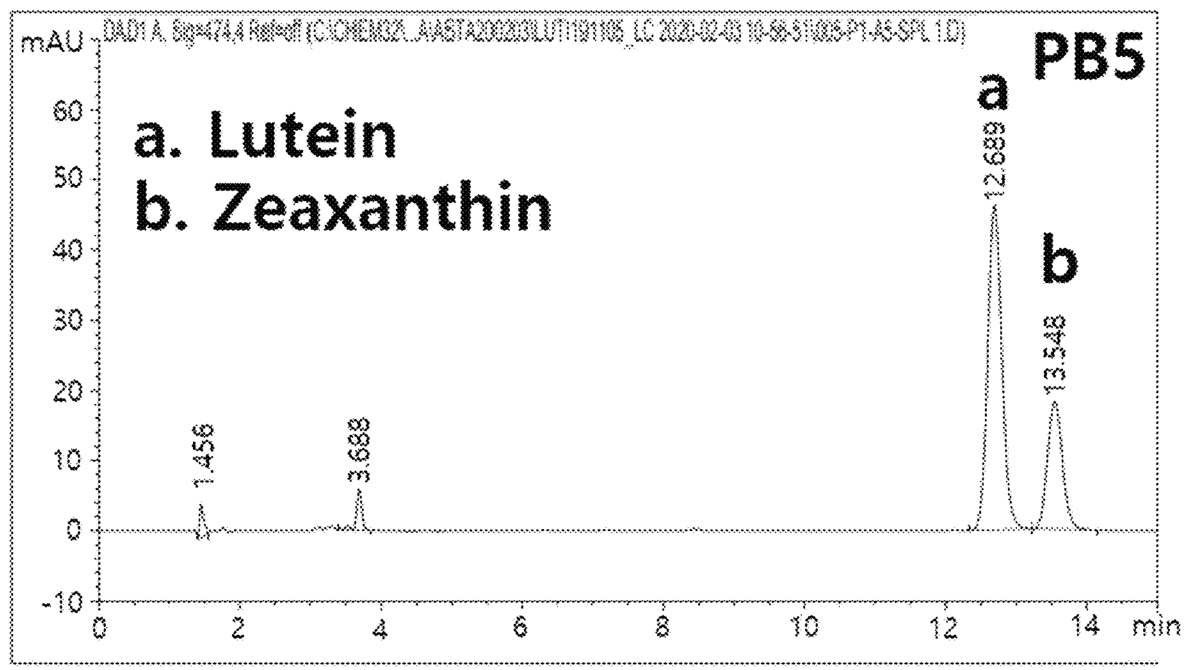
【FIG. 4C】
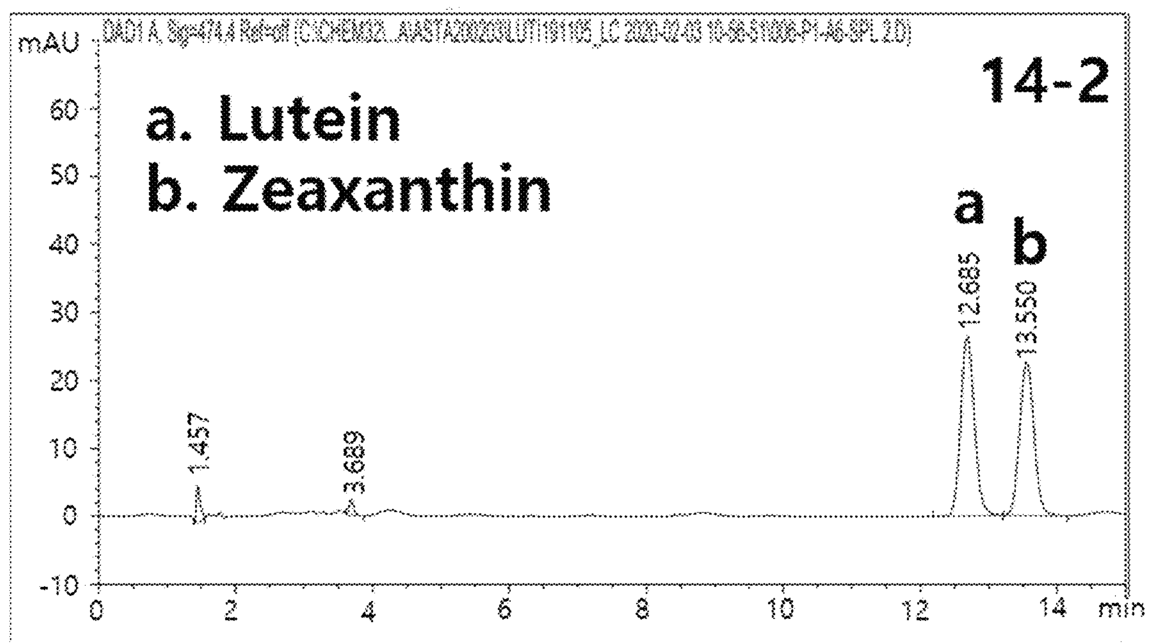

【FIG. 4D】
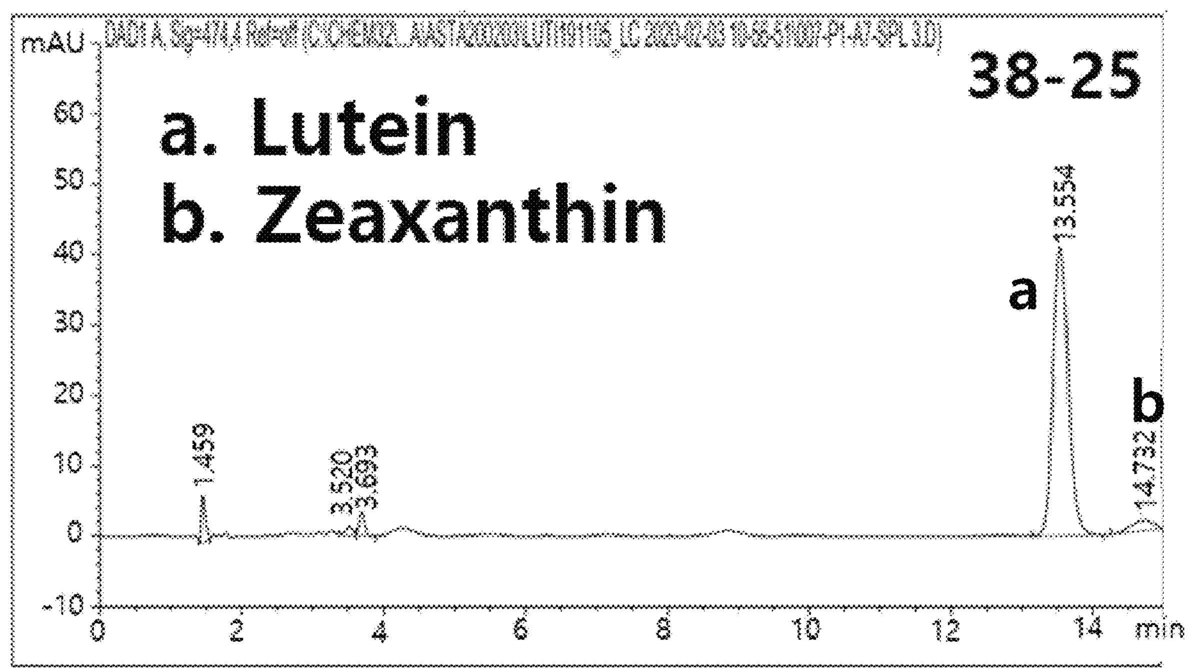

【FIG. 5】 ggtacccttgcagtgccccaaaaactggctaccacctaacaattctcacgcagttttatcctctgcactttgatgtcagcttttgattcgtctgcgta cattacagcgttgagtggccagcaggaaggagaccgcggtccgagacgagtctgagggcgcgctctcgcaacttggattccggatttcttac cctgcatcgacctcggcctggagtcgatcagaaattgtcattgccagattgcctggcgaggacgggtgatatactcaaggcgttgcatcgccc acaaaacacacacttatctgcaagggagttactgcatcaggctctgctcaacagctcgtgacatcgatcgttcagctccccagcaggtgcgtgt ccgcatggagcacccctcccgagacacctgcgttgggtgtcggaggagctcacatgccagggaggtgcccacattgcaccacgcgaccgc gaaataggcagacttcgggcatcctgtcatcgcatgtccgctggccgggaatcatggcctccccaccaggcgtcacgcgctgcccacctccc tccccttgctgcgcagggcaccgcgttcctgtggagagccgaccac*ATGggccccggcatccagcccacctccgcccgcccctgctcccg*

*caccaagcactcccgcttcgccctgctggccgccgccctgaccgcccgccgcgtgaagcagttcaccaagcagttccgctcccgccgcatg*

*gccgaggacatcctgaagctgtggcagcgccagtaccacctgccccgcgaggactccgacaagcgcaccctgcgcgagcgcgtgcacct*

*gtaccgcccccccccgctccgacctgggcggcatcgccgtggccgtgaccgtgatcgccctgtgggccaccctgttcgtgtacggcctgtggttc*

*gtgaagctgccctgggccctgaaggtgggcgagaccgccacctcctgggccaccatcgccgccgtgttcttctccctggagttcctgtacacc*

*ggcctgttcatcaccacccacgacgccatgcacggcaccatcgccctgcgcaaccgccgcctgaacgacttcctgggccagctcgcgatctc*

*cctgtacgcctggttcgactactccgtgctgcaccgcaagcactgggagcaccacaaccacaccggcgagccccgcgtggaccccgacttc*

*caccgcggcaaccccaacctggccgtgtggttcgcccagttcatggtgtcctacatgaccctgtcccagttcctgaagatcgccgtgtggtcca*

*acctgctgctgctggccggcgccccccctggccaaccagctgctgttcatgaccgccgcccccatcctgtccgccttccgcctgttctactacggc*

*acctacgtgccccaccaccccgagaagggccacaccggcgccatgccctggcaggtgtcccgcacctcctccgcctcccgcctgcagtcct*

*tcctgacctgctaccacttcgacctccactgggagcaccaccgctggccctacgcccccctggtgggagctgcccaagtgccgccagatcgcc*

*cgcggcgccgccctggccTGA*GCGGAGGCCTTGGAAATATTCGCGTCACGCGAGGAGTAGGCTCTGCTGGTCGGCCCT

GGATACGCTGACTCTTCAAGCAGTGGGGCACCACACCCACCTTTTGCCAAGGGCAAGGAGTCGGAAGGGGGCGGG

GCTGCCATGCACCCCTGACGGGCATGGCCGTTCCGCGAGGGCGCCAACTGCGGCGGCCTGCCCGCTGGCTCGTGC

CCCCCTACCCCCACCATTGCCTGGAGCGTTTCCATCCCCAAATCACATTCCATCCAAGTTGTATCACTATGCCCCTTTG

GCTCTATACACTGACGGCCTGAGGTCCCTTCTCGGCCGTGGCGGCACACGCCCAACCCCCCACCATACTCTTTGCAT

ACACTGCAATGCTTCGAGCCTGCCTGCCACCTGCTCTGCTTGTCTCCCCTCCCTTCCCTTGAGGTTTTCCAATGCAGT

AAGAGAAGTCGACGTGCATGGACAGATGATTGAGAGATGAGACTAGT

【FIG. 6】

*ATGgccaccgcatccactttctcggcgttcaatgcccgctgcggcgacctgcgtcgctcggcgggctccgggccccggcgcc
cagcgaggcccctccccgtgcgcgctgccatccgctcccgccgcatggccgaggacatcctgaagctgtggcagcgccagt
accacctgccccgcgaggactccgacaagcgcaccctgcgcgagcgcgtgcacctgtaccgcccccccgctccgacctg
ggcggcatcgccgtggccgtgaccgtgatcgccctgtgggccaccctgttcgtgtacggcctgtggttcgtgaagctgccctgg
gccctgaaggtgggcgagaccgccacctcctgggccaccatcgccgccgtgttcttctccctggagttcctgtacaccggcctg
ttcatcaccacccacgacgccatgcacggcaccatcgccctgcgcaaccgccgcctgaacgacttcctgggccagctcgcg
atctccctgtacgcctggttcgactactccgtgctgcaccgcaagcactgggagcaccacaaccacaccggcgagccccgcg
tggacccccgacttccaccgcggcaacccccaacctggccgtgtggttcgcccagttcatggtgtcctacatgaccctgtcccagtt
cctgaagatcgccgtgtggtccaacctgctgctgctggccggcgccccctggccaaccagctgctgttcatgaccgccgccc
ccatcctgtccgccttccgcctgttctactacggcacctacgtgccccaccaccccgagaagggccacaccggcgccatgccc
tggcaggtgtcccgcacctcctccgcctcccgcctgcagtccttcctgacctgctaccacttcgacctccactgggagcaccacc
gctggccctacgccccctggtgggagctgcccaagtgccgccagatcgcccgcggcgccgccctggccTGA*

【FIG. 7A】

MGPGIQPTSARPCSRTKHSRFALLAAALTARRVKQFTKQFRSRRMAEDILKLWQRQYHLP
REDSDKRTLRERVHLYRPPRSDLGGIAVAVTVIALWATLFVYGLWFVKLPWALKVGETATS
WATIAAVFFSLEFLYTGLFITTHDAMHGTIALRNRRLNDFLGQLAISLYAWFDYSVLHRKHW
EHHNHTGEPRVDPDFHRGNPNLAVWFAQFMVSYMTLSQFLKIAVWSNLLLLAGAPLANQL
LFMTAAPILSAFRLFYYGTYVPHHPEKGHTGAMPWQVSRTSSASRLQSFLTCYHFDLHWE
HHRWPYAPWWELPKCRQIARGAALA*

【FIG. 7B】

MATASTFSAFNARCGDLRRSAGSGPRRPARPLPVRAAIRSRRMAEDILKLWQRQYHLPRE
DSDKRTLRERVHLYRPPRSDLGGIAVAVTVIALWATLFVYGLWFVKLPWALKVGETATSWA
TIAAVFFSLEFLYTGLFITTHDAMHGTIALRNRRLNDFLGQLAISLYAWFDYSVLHRKHWEH
HNHTGEPRVDPDFHRGNPNLAVWFAQFMVSYMTLSQFLKIAVWSNLLLLAGAPLANQLLF
MTAAPILSAFRLFYYGTYVPHHPEKGHTGAMPWQVSRTSSASRLQSFLTCYHFDLHWEH
HRWPYAPWWELPKCRQIARGAALA*

| parent | - | PBS | 14-2 | PBS | PBS | 14-2 | 14-2 |
|---|---|---|---|---|---|---|---|
| construct | - | pPB0014 | pPB0038 | pPB0120 | pPB0123 | pPB0120 | pPB0123 |
| strain | PBS | 14-2 | 38-25 | 120A-2 | 123A-5 | 120B-5 | 123B-24 |

【FIG. 8B】
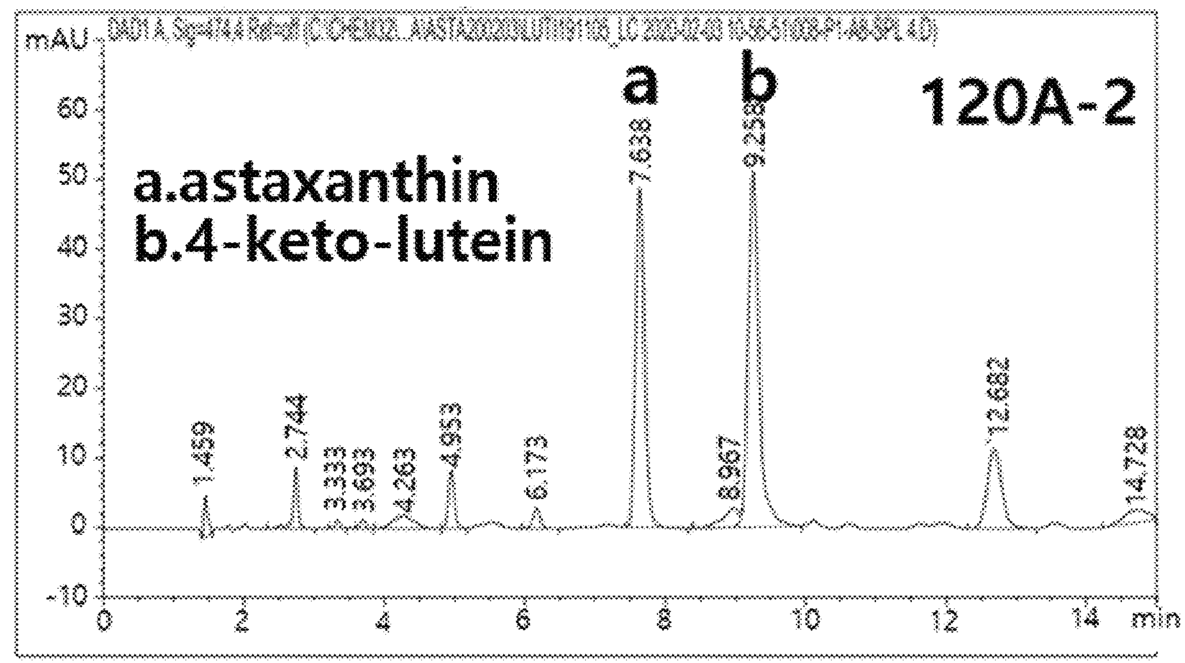
【FIG. 8C】
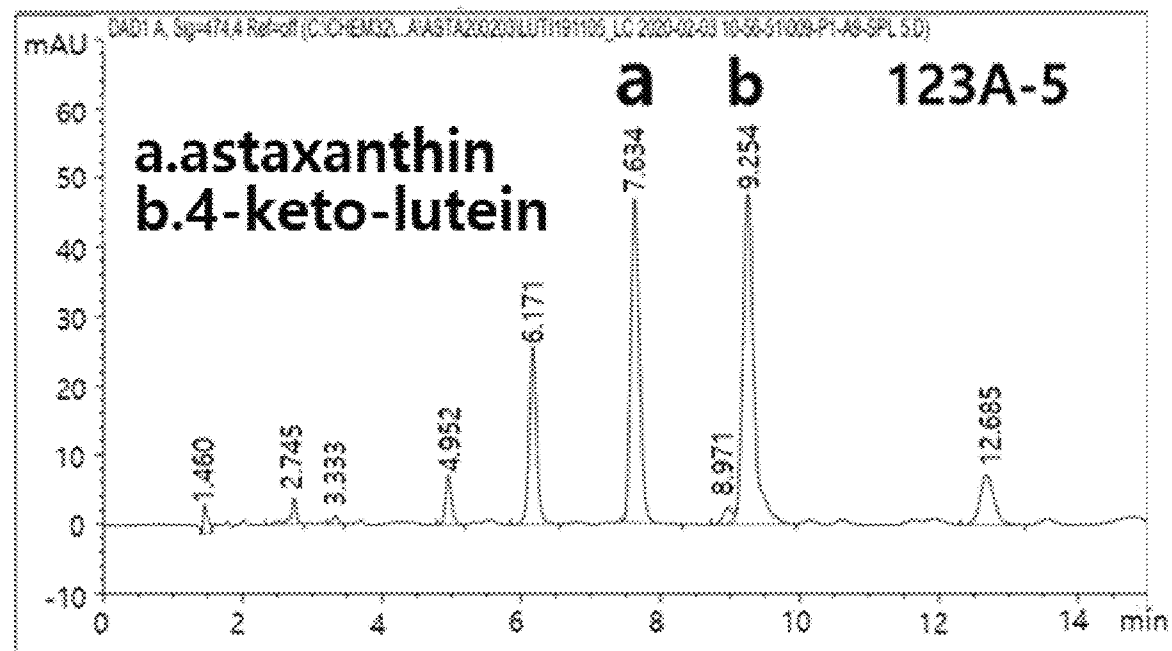

【FIG. 8D】
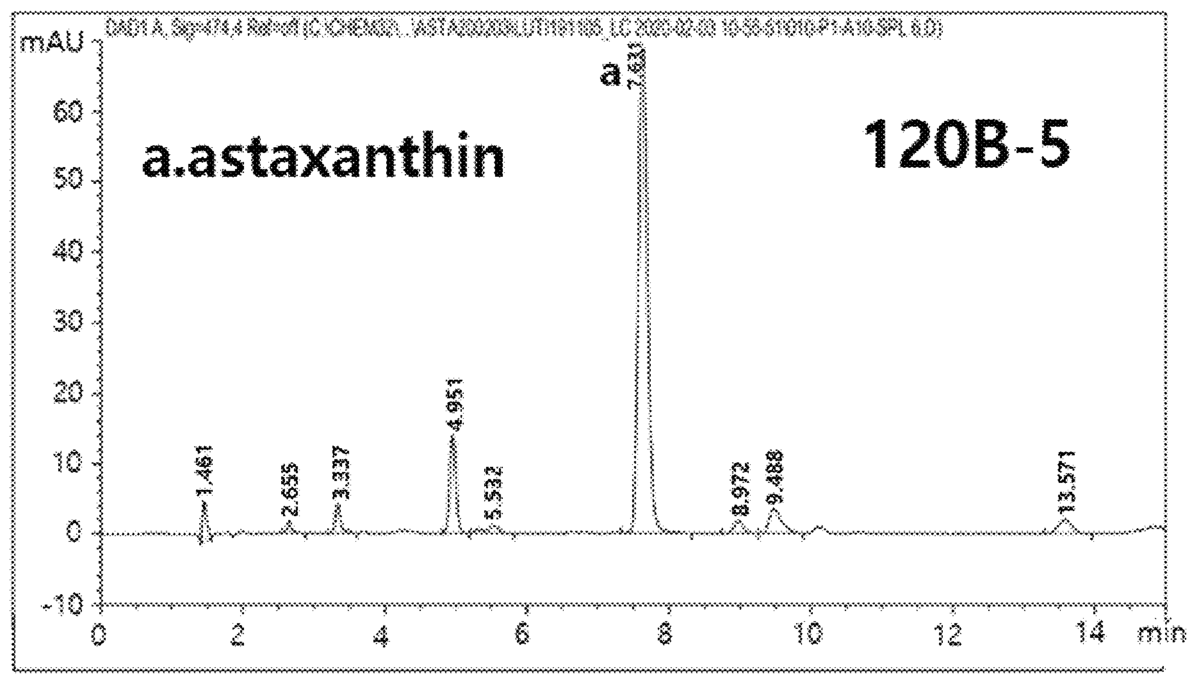

【FIG. 8E】
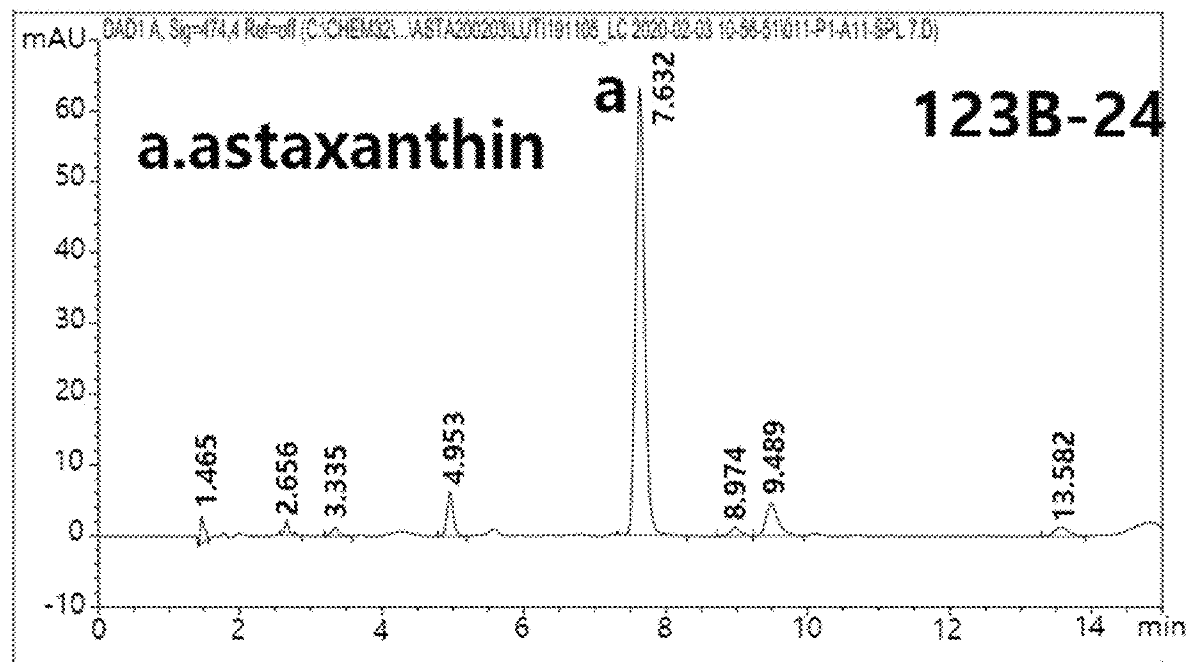

【FIG. 9A】 aagcttTCACTGCTCCATTCACACCCAATTTCCCACCGCCGCACCCGCTCCCAGGTGGGAGGATGG

GAGGGAACCCAGCTGGGAGCCGGAGGAGCATGTGACCCCGGACCTGATCGAGCTATATGCCGC

CAGGGACGCTCGAGCACGGGATGTCAAGGCCGCGGCTGACAAGGCTGGCAAGGGTAGGACAC

CTGCGTTGAGGCAAACGCTGGAGACGGCCGGTCTCAGCATGTGATCCTGTACTTGCTGTGACAA

GGTGGACAATGCAGTACGAGGTGTACCAGGCTAAGTATTCCTAGTATACCGGCACGCCAGATCAT

CTGTACAGGAGTCTGTGCAGGAGTGAAAAGGTAAGAGCCAGAGCCATGACCGGCGACCATCCAT

GTCCCGTCACTCGGATGCACTGGCTGACATCGGCGGCAGGTCATCCAACGGTCCTGAATGATCG

AGAGGAAGCTGCCCGATTTCAAAACGCCCCCCCACGTCGCCCTCCATGGCCGCACAGCATGCT

CAGCACAGGTTGCTGCGTGTCCTCACACAAACTGCTCCTTTAAAGCGATCAACTTTCCAGGGCAT

GGGGCACTCGTACTGACAATCACCCACATTCGTATACCTTTGACGTCATTATTTTTTCGCCCCAAC

GCGGTTGCCATCCCGAGTTGTACCTCCGCGGCTACCATACCCCTGTCTTCTGGCCCTCACCGTC

GCTCGCAGGCGGGATCCAGCGCAGCCAGTCTGAATACTTTTACACAACATAGTACGTAACGCGCA

TTAGGCCCCCAATACCAGCAGCTGGCTCCAGCATGGGCAAGGGTGCGCGGCAGGAGgaattcccc gctttttaattgagcccctttcgtcgctgaatcagcgaaagcaccgcgaaacaatgcctgtcccgtccatgcatctcaacagcctcatgcaaggt ttgcacaagcaagaccattctgatctgggaacttgtaggtgttgtatgggggaggttgtgctcttgaatcaagtggtatcacgtttccggaacacc ccgaaacgtgcatgggcttattgcgatgagagcatttcccaccgcgattgtctcacgcgcatttcggagaaggtttgcagaacactccaggac atgaaatgccttgtcacgtatgaaccatctcccacggccttgaaaagatcgctcgacttccattctagatggtgcaaaaccctacgactcaaga aggtgccaccgactcaggcattgggcacggcgggcagggagaagagaggagttgatcaaaactgctcgatcacgttcccccatggcgatc cgagcagcacatgatgcatcgaggtggcgccgttgcaaaggagttgcgcatgggtcgaagcagggagaaggaaacggcgaggcgtgcc gcgggggtgaattcagagtcaaatctgcgcctgccccggcgctcctgacggggattaacccccacgactgtatccatcgacactcgtctcgg gggaataaaagcggcgacccagctccagaggcgcaatccttctcacaatctgtttaactttcaacaaagtataagtcaattcaacttgacaca

*ATGgccgcgtccgtccactgcaccctgatgtccgtggtctgcaacaacaagaaccactccgcccgccccaagctgcccaactcctccctgc*

*tgcccggcttcgacgtggtggtccaggccgcggccacccgcttcaagaaggagacgacgaccacccgcgccacgctgacgttcgacccccc*

*ccacgaccaactccgagcgcgccaagcagcgcaagcacaccatcgacccctcctcccccgacttccagcccatcccctccttcgaggagt*

*gcttccccaagtccacgaaggagcacaaggaggtggtgcacgaggagtccggccacgtcctgaaggtgcccttccgccgcgtgcacctgtc*

*cggcggcgagcccgccttcgacaactacgacacgtccggcccccagaacgtcaacgcccacatcggcctggcgaagctgcgcaaggag*

*tggatcgaccgccgcgagaagctgggcacgccccgctacacgcagatgtactacgcgaagcagggcatcatcacggaggagatgctgta*

*ctgcgcgacgcgcgagaagctggaccccgagttcgtccgctccgaggtcgcgcggggccgcgccatcatcccctccaacaagaagcacct*

【FIG. 9B】

*ggagctggagcccatgatcgtgggccgcaagttcctggtgaaggtgaacgcgaacatcggcaactccgccgtggcctcctccatcgaggag*
*gaggtctacaaggtgcagtgggccaccatgtggggcgccgacaccatcatggacctgtccacgggccgccacatccacgagacgcgcga*
*gtggatcctgcgcaactccgcggtccccgtgggcaccgtccccatctaccaggcgctggagaaggtggacggcatcgcggagaacctgaa*
*ctgggaggtgttccgcgagacgctgatcgagcaggccgagcagggcgtggactacttcacgatccacgcgggcgtgctgctgcgctacatc*
*cccctgaccgccaagcgcctgacgggcatcgtgtcccgcggcggctccatccacgcgaagtggtgcctggcctaccacaaggagaacttc*
*gcctacgagcactgggacgacatcctggacatctgcaaccagtacgacgtcgccctgtccatcggcgacggcctgcgccccggctccatcta*
*cgacgccaacgacacggcccagttcgccgagctgctgacccagggcgagctgacgcgccgcgcgtgggagaaggacgtgcaggtgatg*
*aacgagggccccggccacgtgcccatgcacaagatccccgagaacatgcagaagcagctggagtggtgcaacgaggcgcccttctaca*
*ccctgggcccccctgacgaccgacatcgcgcccggctacgaccacatcacctccgccatcggcgcggccaacatcggcgccctgggcacc*
*gccctgctgtgctacgtgacgcccaaggagcacctgggcctgcccaaccgcgacgacgtgaaggcgggcgtcatcgcctacaagatcgcc*
*gcccacgcggccgacctggccaagcagcacccccacgcccaggcgtgggacgacgcgctgtccaaggcgcgcttcgagttccgctggat*
*ggaccagttcgcgctgtccctggaccccatgacggcgatgtccttccacgacgagacgctgcccgcggacggcgcgaaggtcgcccacttc*
*tgctccatgtgcggccccaagttctgctccatgaagatcacggaggacatccgcaagtacgccgaggagaacggctacggctccgccgag*
*gaggccatccgccagggcatggacgccatgtccgaggagttcaacatcgccaagaagacgatctccggcgagcagcacggcgaggtcg*
*gcggcgagatctacctgcccgagtcctacgtcaaggccgcgcagaag*TGAGTCCTGGCGACCCTGCTCCCCTGACCCCTGTTC
CCCTGCGCTGCTTCTCCCCGGTGACATCCGACCTGCTGCAAAATTCCCGTTCCTGCACAACACTTGCCTGACCGAGG
GTCGGGTCGCGAAGTAAAAGCCACAATCAACACCCCAGGCACATTAAGAGTGCACAGCATGACGCAGCATAGGGTTT
GTGTCGGAGGAAGGGGGTCGAGTCGCGTTGGCGAGGGGGTGGTCACGATGACCACATCTGCGGGATAATTGAATCC
TCAGGGGAAAATACCAGTCTCTGCTTCCAGGTGCTCCGgagctcCCCAGGCGAGTCAATCAGTTGTGTCATG
AGATTGATCTGCCTGTTGCAGATCCCCCGACCCGCTGCCGGCCCCTCTGCCGTGCGACACCCCT
TGCCCTGGGGTGTGCCTCTTGTCCTGCATCGCACACCTCCTCCGCCGGACCTTCACCCCCTCCC
ACCTCGACACAAGCAGGTGTGGGACGTGATAGTGGTGGGCGCGGGCGTGGCCGGCGCGGCGC
TGGCGCATCAGCAGGGCTTGGACGGCCGACGCGTGCTGCTCCTCGAGCGGGATCTGGCCCAG
CCCGACCGCATCGTGGGCGAGCTGCTGCAGCCTGGCGGCGTGCTGGCCCTGGAGCGCCTGGG
CCTGGGCGGCGCCGTGGACGGCATCGACGCGCAGCCCGTGGTCGGGTACTGCATGTTCAAGG
GCGGGCGCGAGGCGTGCATCGCCTACCCCACCCCCGCCGAGCTGGGGGGTCCAGCGGCTGC
GGCTGCGGCATGCAGGGGCCCCACTGGAAGCGCCAGCGCCGCGCCCGCCGGCGACGCCCCC
GTCACGGGCTTCTCCTTCCACAACGGGCGATTCGTGCAGCGGCTGCGCGCCGCGGCGGCGGC
TGCGCCCGGGGTCACGCTGCGTCGCGGCACGGTGCGCGCGCTGGTGGATGACGCCGGCGCG

【FIG. 9C】

GACTGGGAGGAGGGGCGCGTGGTGACGGGCGTGCGGTACCGCGCGGGCGACGGCGGCGAGC
GCGTGGCACTGGGCCACCTCACCGTGGTCTGCGACGGCATGTACTCGGCCCTGCGGTCCAAGC
TGGCGGTGCCCGACCTGCGCACGCCCTCCCACTTCATCaagctt

【FIG. 10A】 aagcttTCACTGCTCCATTCACACCCAATTTCCCACCGCCGCACCCGCTCCCAGGTGGGAGGATGG
GAGGGAACCCAGCTGGGAGCCAGAGGAGCATGTGACCCCGGACCTGATCAAGCTATATGCCGC
CAGGGACGCTCGAGCACGGGATGTCAAGGCCGCGGCTGACAAGGCTGGCAAGGGCAGGACAC
CTGCGCCGAGGCAAACGCTGGAGACGGCCGGTCTCAGCATGTGATCCTGTACTTGCTGTGACAA
GGTGGACAATGCAGTACGAGTTGTACCAGGCTAAGTATCCCTAGTATACCGGCACGCCAGATCAT
CTGTACAGGAGTCTGTGCAGGAGTAAAAAGGCAACAGCCAGAGCCATGACCGGCGACTATCCAC
ATCCCGTCACTCCGATGCACTGGCTGACATCGGCGGCAGGTCGTCCAACGGTCCTGAATGATCG
AGAGGAAGCTGCCCGATTTCACCCCCCCCCCCCACGTCGCCCTCCATGGCCGCACAGCATGCT
CAGCACAGGTTGCTGCGTGTCCTCACACAAACTGCTCCTTTAAAGCGATCAACTTTCCAGGGCAT
GGGGCACTCGTACTGACAATCACCCACATTCGTATACCTTTGACGTCATTTTTTTTTCGCCCCAAC
GCGGTTGCCATCCCGAGTTGTACCTCCGCGGCTACCATACCCCTGTCTTCTGGCCCTCACCGTC
GCTCGCAGGCGGGATCCAGCGCAGCCAGTCTGAATACTTTTACACAACATAGTACGTAACGCGCA
TTAGGCCCCCAATACCAGCAGCTGGCTCCAGCATGGGCAAGGGTGCGCGGCAGGAGgaattcctttct
tgcgctatgacacttccagcaaaaggtagggcgggctgcgagacggcttcccggcgctgcatgcaacaccgatgatgcttcgacccccccga
agctccttcggggctgcatgggcgctccgatgccgctccagggcgagcgctgtttaaatagccaggcccccgattgcaaagacattatagcg
agctaccaaagccatattcaaacacctagatcactaccacttctacacaggccactcgagcttgtgatcgcactccgctaagggggcgcctctt
cctcttcgtttcagtcacaacccgcaaac*ATGctgctgcaggccttcctgttcctgctggccggcttcgccgccaagatcagcgcctccatgac*
*gaacgagacgtccgaccgccccctggtgcacttcacccccaacaagggctggatgaacgaccccaacggcctgtggtacgacgagaagg*
*acgccaagtggcacctgtacttccagtacaacccgaacgacaccgtctgggggacgcccttgttctggggccacgccacgtccgacgacct*
*gaccaactgggaggaccagcccatcgccatcgccccgaagcgcaacgactccggcgccttctccggctccatggtggtggactacaacaa*
*cacctccggcttcttcaacgacaccatcgacccgcgccagcgctgcgtggccatctggacctacaacaccccggagtccgaggagcagtac*
*atctcctacagcctggacggcggctacaccttcaccgagtaccagaagaaccccgtgctggccgccaactccacccagttccgcgacccga*
*aggtcttctggtacgagccctcccagaagtggatcatgaccgcggccaagtcccaggactacaagatcgagatctactcctccgacgacctg*
*aagtcctggaagctggagtccgcgttcgccaacgagggcttcctcggctaccagtacgagtgccccggcctgatcgaggtccccaccgagc*
*aggaccccagcaagtcctactgggtgatgttcatctccatcaaccccggcgccccggccggcggctccttcaaccagtacttcgtcggcagctt*
*caacggcacccacttcgaggccttcgacaaccagtcccgcgtggtggacttcggcaaggactactacgccctgcagaccttcttcaacaccg*
*acccgacctacgggagcgccctgggcatcgcgtgggcctccaactgggagtactccgccttcgtgcccaccaacccctggcgctcctccatg*
*tccctcgtgcgcaagttctccctcaacaccgagtaccaggccaacccggagacggagctgatcaacctgaaggccgagccgatcctgaac*

【FIG. 10B】

*atcagcaacgccggcccctggagccggttcgccaccaacaccacgttgacgaaggccaacagctacaacgtcgacctgtccaacagcac*
*cggcacccctggagttcgagctggtgtacgccgtcaacaccacccagacgatctccaagtccgtgttcgcggacctctccctctggttcaaggg*
*cctggaggaccccgaggagtacctccgcatgggcttcgaggtgtccgcgtcctccttcttcctggaccgcgggaacagcaaggtgaagttcgt*
*gaaggagaacccctacttcaccaaccgcatgagcgtgaacaaccagcccttcaagagcgagaacgacctgtcctactacaaggtgtacgg*
*cttgctggaccagaacatcctggagctgtacttcaacgacggcgacgtcgtgtccaccaacacctacttcatgaccaccgggaacgccctgg*
*gctccgtgaacatgacgacgggggtggacaacctgttctacatcgacaagttccaggtgcgcgaggtcaagTGA*TTGATTGGAACTCA
CAAAGCGGCCCACGGCTTCGAACGTCCCGTGTCAATTGCGCGGGGTGTGCCAGAGTTTCTGCGCCACCGATGCTCA
CCCTAGGGGGGGATGCCCTTTGACATTCATGTGTGCCTGCATGCACGTTTGTATCAGTCTCACCACACCTTGAAGATT
TTTGGGAGGGGGGGGGAAGTCGGAATGGAAACgagctcCCCAGGCGAGTCAATCAGTTGTGTCATGAGAT
TGATCTGCCTGTTGCAGATCCCCCGACCCGCTGCCGGCCCCTCTGCCGTGCGACACCCCTTGC
CCTGGGGTGTGCCTCTTGTCCTGCATCGCACACCTCCTCCGCCGGACCTTCACCCCCTCCCACC
TCGACACAAGCAGGTGTGGGACGTGATAGTGGTGGGCGCGGGCGTGGCCGGCGCGGCGCTGG
CGCATCAGCAGGGCTTGGACGGCCGACGCGTGCTGCTCCTCGAGCGGGATCTGGCCCAGCCC
GACCGCATCGTGGGCGAGCTGCTGCAGCCTGGCGGCGTGCTGGCCCTGGAGCGCCTGGGCCT
GGGCGGCGCCGTGGACGGCATCGACGCGCAGCCCGTGGTCGGGTACTGCATGTTCAAGGGCG
GGCGCGAGGCGTGCATCGCCTACCCCACCCCCGCCGAGCTGGGGGGTCCAGCGGCTGCGGCT
GCGGCATGCAGGGGCCCCACTGGAAGCGCCAGCGCCGCGCCCGCCGGCGACGCCCCCGTCA
CGGGCTTCTCCTTCCACAACGGGCGATTCGTGCAGCGGCTGCGCGCCGCGGCGGCGGCTGCG
CCCGGGGTCACGCTGCGTCGCGGCACGGTGCGCGCGCTGGTGGATGACGCCGGCGCGGACT
GGGAGGAGGGGCGCGTGGTGACGGGCGTGCGGTACCGCGCGGGCGACGGCGGCGAGCGCG
TGGCACTGGGCCACCTCACCGTGGTCTGCGACGGCATGTACTCGGCCCTGCGGTCCAAGCTGG
CGGTGCCCGACCTGCGCACGCCCTCCCACTTCATCaagctt

【FIG. 12】

<u>MQFSLAGMNTRALQTGARPSLPAARPSRRVRPAR</u>RSAPCPVARTMGGGEEQPSSAEGV
AWDKISTDELADWAGAGPPTPLLDTVAFPVHIKNFNSRQLQQLCKELRADLIHTVAKTGGH
LGSSLGVVELTVALHHVFNTPEDRIVWDVGHQAYIHKMLTGRRARMHTIRQQGGLSGFTR
RAESVYDPFGAGHSSTSVSAALGMAVGRDRKGRANNCIAVIGDGAITGGMAYEAMNHAG
FLDTNMIVILNDNQQVSLPTQYNGKNQEPVGALSSALARLQANRQLRELREIAKGVTKQLP
DVIQNATAKIDEYARGMISGTGSTLFEELGFYYIGPVDGHNMQDLVDVLSEIKATETVGPVL
LHVVTQKGRGYTPAETASDRMHGVVQYDTLTGKQKKGSGGPQSYTNYFADALVAEAKRD
ARVLGIHAAMGGGTGMNRFEAAFPDRVFDTGIAEQHAVTFAAGLATEGLVPFVAIYSTFLQ
RGYDQIVHDVSLQSLPVRFALDRAGNVGADGATHAGAFDVTYLACLPNMVVMAPSNEAE
LVHAVATAAAIDDRPSAFRFPRGNGLGVDLAAAGVTDDLKGQPMEVGRGVVRRGGADVA
LLGYGTCVNACLAAADLLAAQGVSATVVDARFCKPLDTALVRRMAAEHPVMITVEEGSIGG
FAAHVMQFLALEGLLDGKLKFRPMTLPDRYIEHGTQAEQMAEAGLTASHIAGTALSVMGV
KRDAPSIFST*

【FIG. 13】

MRCSAQLNTRGPTLPNSARPRTCRVVSASAAPVPSAWPGRVVLPEKSASRTGPKKFSLL
GSTGSIGTQTLDIVAEHPDRFQVVSLAAGGNVALLAEQIARFSPSLVSVRDSGGARALEAA
LDAAGVDRRPEIQIGAAGIDAVAAHPEADACVTGIVGCAGLRPTMAAIEAGKDICLANKETLI
AGGPTVLPAAAKHGVSILPADSEHSAIFQCLQGLPEGGLRRIILTASGGAFRDLPVSELPKV
TVADALKHPNWAMGKKITIDSATLMNKGLEVIEAHYLFGASYDNIDIVIHPQSIVHSMIETQD
SSVLAQLGWPDMRLPILYTMSWPERVPCSEVTWPRLDFVKAGNLTFRQPDHAKYPAMEL
AYSAGRAGGTMTGVMSAANEAAVELFLEEAIGYLDIVPVVEAACEAHRVELVERPSLEEIV
HYDQWARRHVRESVAKRAPAAVPAL*

【FIG. 14】

MAAVVEAGHAASKQKTEAHQTKQEFLAVFEKLRDELLEDSILAGQPESSKDWLRTMLDYN
VPHGKLNRGMAVLDVLLAARGGDVTEKEREAANVLGWCIELLQAYFLVADDIMDSSLTRR
GQPCWYRQPHVGMVAINDGIILESCIYRLLKLHFRAHPAYVHLLELFHDTTHRTAHGQLLDT
TTAPPGGVDLTRYTEGTYLRIVTYKTAFYTIYLPVACGLALAGVTDEASLALAEDLSVRMGR
YFQIQDDVLDAFGEPEVIGKVGTDIQDSKCSWLVVRALAVASAEQREAIKANYGRDDAEAV
EAVKAVYRELDLPAAFAAYEQESYDGLVQAIEGQDKFPPAVFMGILAKIYKRTK

【FIG. 15】

MGKLGELLSHPDEIIPMAAMYLAARRAAVLPHDPDLAFCYSMLNKVSRSFAIVIQQLPEQL
RDAVCVFYLVLRALDTVEDDMAIDQAEKVPILLSFHEKTYEKDWSMKCGHGHYVELMEQY
PVVCAAFQGLEPQYQEVITDICRRMGAGMAEFIVKEVETVKDYDLYCHYVAGLVGVGLSN
LFAGSGLESEDFASLHELSNGMGLFLQKTNIIRDYLEDIMEEPAPRMFWPKEIWGKHGDSL
EDFKDPENAEAAVACLNDMIADALRHVDASLDYMQRLRNRPIFRFCAVPQIMAIGTLAACF
DNPSVFTGVVKMRRGQTAKIMHDVEDYADLLAYFRAFGQALAAKARAARGKGAESVGRA
AERVVAGCSAALADLSRAENARMAAAARRPLSLPARALLLVAALLYLFLAWRAEGVRRWL
GVDSPPAAHKLDYYNQIVASMFLGYSLFAVGTGRRP*

【FIG. 16A】 aagcttGCACAGTCAGTCGTCATCCACGAAGTCGCGCCCGTCTGTCCACCGGGGTCTCCTGAACG

CAGCAATCTCCTCCTGAGTGTATGAGCCCGTGGCCGGGAGTTTGTATGCAGGGCGAGGCAAGGA

CGACCATGCCGGGAGAAACCCAAGGTGACGAAGTGACATTGTGCTCGATCACTCCATGCACTGC

CTCACTCGCCCATGTACCTTGGTCATGTACTCCCCAGTCTGCATCTTGGTGTTCCTGTTCAGCTC

GCGGAGCTCCTCCAGGCGCTGCTCGTCGCGGCGGTCCCGCGAGATGTAAAAGGCAGGGACAC

CCACCCCCAGGGCCACTCCCAGTAGAGCCCCCCTACAGCAACCAGGGTGTCCGGATCGCTAA

AGTCGATGTTGATCGCGCGGCACGGTGGCATTATCGGGCGTGGATGGCCCCATGATCGGTGCAA

CGAAGGCGCCCTCATGGCAGGTCCGCATGGTCGTCCATTGCAGGGGATACCCGCTCGCACTTTC

GTTGACAATAACATCCTCGTATAGTTGGAGAAAGGATTTGTGATCTGTCTCTGGAGGCCCTTAAAG

TCCTGCCCCTCCTCTGCTGGAACCTGACCTCTCATGCCCCTGCGCCACGCCCCCGGATCTGATA

TGGCTCTGATATGGGTGGCTCGTACCTCTTGGCTAGGCGACCCCCCTAAGCACGCGTGCGGGCC

AGGGCACAACATTATATTTTGCCCTCTCCTTCGTCAACGCTCATTTTTTTGGAATACTAACGTTTAA

AAGCTCTCGggtacctcccgcttttaattgagccccttcgtcgctgaatcagcgaaagcaccgcgaaacaatgcctgtcccgtccatg catctcaacagcctcatgcaaggtttgcacaagcaagaccattctgatctgggaacttgtaggtgttgtatgggggaggttgtgctcttgaatcaa gtggtatcacgtttccggaacaccccgaaacgtgcatgggcttattgcgatgagagcatttcccaccgcgattgtctcacgcgcatttcggaga aggtttgcagaacactccaggacatgaaatgccttgtcacgtatgaaccatctcccacggccttgaaaagatcgctcgacttccattctagatg gtgcaaaaccctacgactcaagaaggtgccaccgactcaggcattgggcacggcgggcagggagaagagaggagttgatcaaaactgc tcgatcacgttcccccatggcgatccgagcagcacatgatgcatcgaggtggcgccgttgcaaaggagttgcgcatgggtcgaagcaggga gaaggaaacggcgaggcgtgccgcgggggtgaattcagagtcaaatctgcgcctgccccggcgctcctgacggggattaacccccacga ctgtatccatcgacactcgtctcgggggaataaaagcggcgacccagctccagaggcgcaatccttctcacaatctgtttaactttcaacaaag tataagtcaattcaacttgacaca*ATGgccgcgtccgtccactgcaccctgatgtccgtggtctgcaacaacaagaaccactccgcccgccc*

*caagctgcccaactcctccctgctgcccggcttcgacgtggtggtccaggccgcggccacccgcttcaagaaggagacgacgaccacccg*

*cgccacgctgacgttcgacccccccacgaccaactccgagcgcgccaagcagcgcaagcacaccatcgacccctcctcccccgacttcca*

*gcccatcccctccttcgaggagtgcttccccaagtccacgaaggagcacaaggaggtggtgcacgaggagtccggccacgtcctgaaggt*

*gcccttccgccgcgtgcacctgtccggcggcgagcccgccttcgacaactacgacacgtccggcccccagaacgtcaacgcccacatcgg*

*cctggcgaagctgcgcaaggagtggatcgaccgccgcgagaagctgggcacgccccgctacacgcagatgtactacgcgaagcagggc*

*atcatcacggaggagatgctgtactgcgcgacgcgcgagaagctggaccccgagttcgtccgctccgaggtcgcgcggggccgcgccatc*

*atcccctccaacaagaagcacctggagctggagcccatgatcgtgggccgcaagttcctggtgaaggtgaacgcgaacatcggcaactcc*

【FIG. 16B】

*gccgtggcctcctccatcgaggaggaggtctacaaggtgcagtgggccaccatgtggggcgccgacaccatcatggacctgtccacgggc*

*cgccacatccacgagacgcgcgagtggatcctgcgcaactccgcggtccccgtgggcaccgtccccatctaccaggcgctggagaaggtg*

*gacggcatcgcggagaacctgaactgggaggtgttccgcgagacgctgatcgagcaggccgagcagggcgtggactacttcacgatcca*

*cgcgggcgtgctgctgcgctacatcccccctgaccgccaagcgcctgacgggcatcgtgtcccgcggcggctccatccacgcgaagtggtgc*

*ctggcctacccacaaggagaacttcgcctacgagcactgggacgacatcctggacatctgcaaccagtacgacgtcgccctgtccatcggcg*

*acggcctgcgccccggctccatctacgacgccaacgacacggcccagttcgccgagctgctgacccagggcgagctgacgcgccgcgcg*

*tgggagaaggacgtgcaggtgatgaacgagggccccggccacgtgcccatgcacaagatccccgagaacatgcagaagcagctggagt*

*ggtgcaacgaggcgcccttctacaccctgggccccctgacgaccgacatcgcgcccggctacgaccacatcacctccgccatcggcgcgg*

*ccaacatcggcgccctgggcaccgccctgctgtgctacgtgacgcccaaggagcacctgggcctgcccaaccgcgacgacgtgaaggcg*

*ggcgtcatcgcctacaagatcgccgcccacgcggccgacctggccaagcagcacccccacgcccaggcgtgggacgacgcgctgtcca*

*aggcgcgcttcgagttccgctggatggaccagttcgcgctgtccctggaccccatgacggcgatgtccttccacgacgagacgctgcccgcg*

*gacggcgcgaaggtcgcccacttctgctccatgtgcggccccaagttctgctccatgaagatcacggaggacatccgcaagtacgccgagg*

*agaacggctacggctccgccgaggaggccatccgccagggcatggacgccatgtccgaggagttcaacatcgccaagaagacgatctcc*

*ggcgagcagcacggcgaggtcggcggcgagatctacctgcccgagtcctacgtcaaggccgcgcagaagTGA*GTCCTGGCGACC

CTGCTCCCCTGACCCCTGTTCCCCTGCGCTGCTTCTCCCCGGTGACATCCGACCTGCTGCAAAATTCCCGTTCCTGC

ACAACACTTGCCTGACCGAGGGTCGGGTCGCGAAGTAAAAGCCACAATCAACACCCCAGGCACATTAAGAGTGCACA

GCATGACGCAGCATAGGGTTTGTGTCGGAGGAAGGGGGTCGAGTCGCGTTGGCGAGGGGGTGGTCACGATGACCA

CATCTGCGGGATAATTGAATCCTCAGGGGAAAATACCAGTCTCTGCTTCCAGGTGCTCCGactagtcttgcagtgccccaa aaactggctaccacctaacaattctcacgcagttttatcctctgcactttgatgtcagcttttgattcgtctgcgtacattacagcgttgagtggcca gcaggaaggagaccgcggtccgagacgagtctgagggcgcgctctcgcaacttggattccggatttcttaccctgcatcgacctcggcctgg agtcgatcagaaattgtcattgccagattgcctggcgaggacgggtgatatactcaaggcgttgcatcgcccacaaaacacacacttatctgc aagggagttactgcatcaggctctgctcaacagctcgtgacatcgatcgttcagctccccagcaggtgcgtgtccgcatggagcacccctccc gagacacctgcgttgggtgtcggaggagctcacatgccagggaggtgcccacattgcaccacgcgaccgcgaaataggcagacttcggg catcctgtcatcgcatgtccgctggccgggaatcatggcctccccaccaggcgtcacgcgctgcccacctccctccccttgctgcgcagggca ccgcgttcctgtggagagccgaccacATGGTCCTGTGCGCTGGTAGTTTGAGCTGCAGGGCGCCGCCTTCA

GGCGGTGCTAGGTTGGAGCGGGGGTCCCCCTTCGTGCGCCTGGGCCACCATGCCCGCCCACA

AGCTCGCAGACGGATGTCAGACCTCGTAATAAGGTCCATCGCAGCCCCTGCTCCGCCCCCGCTG

CGACCTGCATCTCAGCCTCAAGCCCCACCTGCATCAGAGACCTTCACGGTGAGTCATGATCGAG

【FIG. 16C】

GTCGGCCCCTGCAGCGCTCGTGCTCCGGAAACGACCCGCTACTCAATCCCTGAACCATGAATAC
TTCAGGGGGGCCGCGAACTGGCCAACCGCCCTCCCTTCTCCCTCCAAGACATCCGCAACGCCA
TCCCGGCGGAGTGCTGGAAGAAGGACACCTTCAAGTCCTTCGCCTACCTGGCGCTAGATGTAGG
AATCGTTGCTGCCCTGGCCGTGACAGCACATGCCGTCAACTCGCCATGGCTCTGGCCCTTCTAC
TGGCTGGCGCAGGGGACCATGTTCTGGGCCCTGTTTGTCGTCGGCCACGACTGGTGCGGTTGG
AGGGGGTAATCTGGCGACCCTGCAGGGCATGCAGTGGGGACAAGAGCATCGCCAGGCTCCGCC
TTGCCTGCTGATCCCAGCCCGACTTGGCTGGACAATAGATGCTGTCGGGGACATGCCGCAGTGC
ATGCCACAATGGGCCCCTTCAACAACTGACCACCACTATGACCCATATTCCCTGCAGCGGCCACC
AGAGCTTCAGCACAAACAAGCAGCTGAATGACGTGGaagctt

【FIG. 17】 ggaatcccgcctccgagatgaagccgtggttggcacggaggaggccgctgcgggccagagtgttcttctgctgcacgtcctcc ggctttggtggctcgctgggcttgggtgcggccatgagctgcagtgcaagtgtacatataggtcaatcttatgacccggcactac caatgatgatcaacaccgagcggccctctgtgttgtgcttgcctctttaccttcactgcgtactgctgcaggagcttcatgaggatc acactgacggtcagggggatcagcacccagtcccggacatcccgatccagtacgaggtcctggctgaccatgatggtaggt gaagttgggccctgggaggagcgctagaggagcctcggggcaaagatcaccctactctgacgtggctggctcaatcaccca tccctcccctttgaagtcggctctcagtttgcgttgtttcgaaatcgagccacaatcgaatatacactacctaaaggctctcaccac ctggcgtacctcggaatgcccatcagcccaaacacatgagaaaggcgcgcgcggttcgaccccagtccgtcgattgacgc agtggggagctccattctgtcagctcttgggtggccaggtcgctgacagattggcacatacaggaccctgccgacccgttcctc cagcactttgtgaatttaagcagcgcattagatcgtcgatggcttagagaaccccgcgcctgctcccccatctccctttcacacgt ttgaacacccggaccggcc

【FIG. 18A】 aagcttAGCATACTCCTATTCTGACAATGTCACAGTCGGTCTGCCAGGCGATAGTGGCTTTGCTGTC
AGACTCGGCCCCGGACTCTCCCCTGAACTGCGACGCCGGGAATCTGTTGAGAGGAGGCGATCT
GCGAGGGTTCGCCTCCATGGCCCGCATGTACACCATCGAGTATGCCATGAAGCGATGATGTCTGT
GAAAATGATGTTCAGAATTCATTATATACTCATGTTTTTGTGTAAATGCTGTGTCGACTTAAGTTACC
GAGCTGGCTGACAGAGACAATCTTCAGGTCAAATGTTGGCACCAATGATCGCGACGATCGTTCA
GGGGTTATCAAGTCAGATCTGAACGAAAACCAGAAATCAAATTTGCCAAAGCGCATGTTTGTATGT
CGAGAATTATCATGCGGGTGACTGGCTCGCTAATTCTGGCATGGAAGGATGCCACATCGAATTGA
TCCGGGGAGACTAACACTTGTCAGAATTGCAATGTGCCATATTCCAGATATCCCAGCCGGCCCTT
CTATAAACCACCTGCGGGCTCAGATACCTACGAAGAGGCTCAGATAACTCAAGGACGTGCATTCG
AATTATCCCTGCCGCGCGGAAACATCAGACCAGGTGCGGATGCTGAGCGTCGAGTTGGGTGCTT
GATAGACCTTCACCTTGATCTGAGGTTCCCGTCCCCAGAGCACTCGAATCTCCGGCATCTTACAG
GCAAACCGCAAACAGTAAATAATGGCGAGCACCATCACCATGggtacccttgcagtgccccaaaaactggctac
cacctaacaattctcacgcagttttatcctctgcactttgatgtcagcttttgattcgtctgcgtacattacagcgttgagtggccagcaggaagga
gaccgcggtccgagacgagtctgagggcgcgctctcgcaacttggattccggatttcttaccctgcatcgacctcggcctggagtcgatcaga
aattgtcattgccagattgcctggcgaggacgggtgatatactcaaggcgttgcatcgcccacaaaacacacacttatctgcaagggagttact
gcatcaggctctgctcaacagctcgtgacatcgatcgttcagctccccagcaggtgcgtgtccgcatggagcacccctcccgagacacctgc
gttgggtgtcggaggagctcacatgccagggaggtgcccacattgcaccacgcgaccgcgaaataggcagacttcgggcatcctgtcatcg
catgtccgctggccgggaatcatggcctccccaccaggcgtcacgcgctgcccacctccctccccttgctgcgcagggcaccgcgttcctgtg
gagagccgaccac*ATGtccgccgccgccgccgagaccgacgtgtccctgcgccgccgctccaactccctgaacggcaaccacaccaa*
*cggcgtggccatcgacggcaccctggacaacaacaaccgccgcgtgggcgacaccaacacccacatggacatctccgccaagaagac*
*cgacaacggctacgccaacggcgtgggcggcggcggctggcgctccaaggcctccttcaccacctggaccgcccgcgacatcgtgtacgt*
*ggtgcgctaccactggatcccctgcatgttcgccgccggcctgctgttcttcatgggcgtggagtacaccctgcagatgatccccgcccgctccg*
*agcccttcgacctgggcttcgtggtgacccgctccctgaaccgcgtgctggcctcctcccccgacctgaacaccgtgctggccgccctgaaca*
*ccgtgttcgtgggcatgcagaccacctacatcgtgtggacctggctggtggagggccgcgcccgcgccaccatcgccgccctgttcatgttca*
*cctgccgcggcatcctgggctactccacccagctgcccctgccccaggacttcctgggctccggcgtggacttccccgtgggcaacgtgtcctt*
*cttcctgttcttctccggccacgtggccggctccatgatcgcctccctggacatgcgccgcatgcagcgcctgcgcctggccatggtgttcgacat*
*cctgaacgtgctgcagtccatccgcctgctgggcacccgcggccactacaccatcgacctggccgtgggcgtgggcgccggcatcctgttcg*
*actccctggccggcaagtacgaggagatgatgtccaagcgccacctgggcaccggcttctccctgatctccaaggactccctggtgaacTG*

【FIG. 18B】

AGCGGAGGCCTTGGAAATATTCGCGTCACGCGAGGAGTAGGCTCTGCTGGTCGGCCCTGGATACGCTGACTCTTCAA
GCAGTGGGGCACCACACCCACCTTTTGCCAAGGGCAAGGAGTCGGAAGGGGGCGGGGCTGCCATGCACCCCTGAC
GGGCATGGCCGTTCCGCGAGGGCGCCAACTGCGGCGGCCTGCCCGCTGGCTCGTGCCCCCCTACCCCCACCATTG
CCTGGAGCGTTTCCATCCCCAAATCACATTCCATCCAAGTTGTATCACTATGCCCCTTTGGCTCTATACACTCACGGCC
TGAGGTCCCTTCTCGGCCGTGGCGGCACACGCCCAACCCCCCACCATACTCTTTCCATACACTGCAATGCTTCGAGC
CTGCCTGCCACCTGCTCTGCTTGTCTCCCCTCCCTTCCCTTGAGGTTTTCCAATGCAGTAAGAGAAGTCGACGTGCAT
GGACAGATGATTGAGAGATGAGactagtctttcttgcgctatgacacttccagcaaaaggtagggcgggctgcgagacggcttcccgg
cgctgcatgcaacaccgatgatgcttcgacccccgaagctccttcggggctgcatgggcgctccgatgccgctccagggcgagcgctgttta
aatagccaggcccccgattgcaaagacattatagcgagctaccaaagccatattcaaacacctagatcactaccacttctacacaggccact
cgagcttgtgatcgcactccgctaagggggcgcctcttcctcttcgtttcagtcacaacccgcaaac*ATGctgctgcaggccttcctgttcctgct*
*ggccggcttcgccgccaagatcagcgcctccatgacgaacgagacgtccgaccgccccctggtgcacttcacccccaacaagggctggat*
*gaacgaccccaacggcctgtggtacgacgagaaggacgccaagtggcacctgtacttccagtacaacccgaacgacaccgtctgggga*
*cgcccttgttctggggccacgccacgtccgacgacctgaccaactgggaggaccagcccatcgccatcgccccgaagcgcaacgactccg*
*gcgccttctccggctccatggtggtggactacaacaacacctccggcttcttcaacgacaccatcgacccgcgccagcgctgcgtggccatct*
*ggacctacaacaccccggagtccgaggagcagtacatctcctacagcctggacggcggctacaccttcaccgagtaccagaagaacccc*
*gtgctggccgccaactccacccagttccgcgacccgaaggtcttctggtacgagccctcccagaagtggatcatgaccgcggccaagtccc*
*aggactacaagatcgagatctactcctccgacgacctgaagtcctggaagctggagtccgcgttcgccaacgagggcttcctcggctaccag*
*tacgagtgccccggcctgatcgaggtccccaccgagcaggaccccagcaagtcctactgggtgatgttcatctccatcaaccccggcgcccc*
*ggccggcggctccttcaaccagtacttcgtcggcagcttcaacggcacccacttcgaggccttcgacaaccagtcccgcgtggtggacttcgg*
*caaggactactacgccctgcagaccttcttcaacaccgacccgacctacgggagcgccctgggcatcgcgtgggcctccaactgggagtac*
*tccgccttcgtgcccaccaacccctggcgctcctccatgtccctcgtgcgcaagttctccctcaacaccgagtaccaggccaacccggagacg*
*gagctgatcaacctgaaggccgagccgatcctgaacatcagcaacgccggcccctggagccggttcgccaccaacaccacgttgacgaa*
*ggccaacagctacaacgtcgacctgtccaacagcaccggcaccctggagttcgagctggtgtacgccgtcaacaccacccagacgatctc*
*caagtccgtgttcgcggacctctccctctggttcaagggcctggaggaccccgaggagtacctccgcatgggcttcgaggtgtccgcgtcctcc*
*ttcttcctggaccgcgggaacagcaaggtgaagttcgtgaaggagaacccctacttcaccaaccgcatgagcgtgaacaaccagcccttca*
*agagcgagaacgacctgtcctactacaaggtgtacggcttgctggaccagaacatcctggagctgtacttcaacgacggcgacgtcgtgtcc*
*accaacacctacttcatgaccaccgggaacgccctgggctccgtgaacatgacgacgggggtggacaacctgttctacatcgacaagttcc*
*aggtgcgcgaggtcaag*TGATTGATTGGAACTCACAAAGCGGCCCACGGCTTCGAACGTCCCGTGTCAATTGCGCGGG
GTGTGCCAGAGTTTCTGCGCCACCGATGCTCACCCTAGGGGGGGATGCCCTTTGACATTCATGTGTGCCTGCATGCA

【FIG. 18C】

CGTTTGTATCAGTCTCACCACACCTTGAAGATTTTTGGGAGGGGGGGGAAGTCGGAATGGAAACctcgagCAACG
CTACGCAACTCCCTTCGATGGCTTCAAGTACGGAGATGTGGGCATCCAGGATTCGCATGTGCTGC
TTCAGCCCTCCTCATGCCACTAGCACTCATTTTTCGACTCCCGGATTGCCAGGTTCAAGGGCATC
AAGGAGTCGGAGATCAGCCGCGCCATGACCTCCCGCTACTTCGAGGACCTAAACGTCAATGCCG
AGGTGCTTTTGCATATATTTACAGCTAATTATGATGGGTGTGGTGCGCGATATGCTTGCAAGGTCTC
CGGTGAGCTAATGATCGGCACATCCCTTCCGCGCATCCGCAGGTCGATGTCGTCATTGTTGGGG
CTGGGTCTGCGGGCCTCTCGTGCGCCTATGAGCTGAGCAAGCACCCGGATGTCAAGGTATGGG
CTGAGCAGGGCACATCCTCAGATGATGTTGCTGTAATTGCAATTGAAACTTGCGGTTGTTCCCAG
CACAGCCTCAATCAATCATGTGTGCTGCGTTGGAAACGCTATGATACCCCAGCCTTCAACATGGG
GCAGGGATATCGTTTACACCTGCTTGAACCCCCCGCAACAGGTGGCCATCATCGAGCAGGGCGT
CGCCCCTGGGGGTGGAGCGTGGCTGGGGGGTCAGCTCTTCTCGGCTATGTGTGTGAGTCTAGG
CACGGGGACGGGTGGACTGAAGCAAGGGTTGGGCGCAGGGTGTTGATATCCATGTGTTGGACA
TTCTCGTTGGGAAAACAAGATGTGTGTATTTAGTGCTATCTCGGTGGCTGCATTCCaagctt

【FIG. 19A】 aagcttAGCATACTCCTATTCTGACAATGTCACAGTCGGTCTGCCAGGCGATAGTGGCTTTGCTGTC
AGACTCGGCCCCGGACTCTCCCCTGAACTGCGACGCCGGGAATCTGTTGAGAGGAGGCGATCT
GCGAGGGTTCGCCTCCATGGCCCGCATGTACACCATCGAGTATGCCATGAAGCGATGATGTCTGT
GAAAATGATGTTCAGAATTCATTATATACTCATGTTTTTGTGTAAATGCTGTGTCGACTTAAGTTACC
GAGCTGGCTGACAGAGACAATCTTCAGGTCAAATGTTGGCACCAATGATCGCGACGATCGTTCA
GGGGTTATCAAGTCAGATCTGAACGAAAACCAGAAATCAAATTTGCCAAAGCGCATGTTTGTATGT
CGAGAATTATCATGCGGGTGACTGGCTCGCTAATTCTGGCATGGAAGGATGCCACATCGAATTGA
TCCGGGGAGACTAACACTTGTCAGAATTGCAATGTGCCATATTCCAGATATCCCAGCCGGCCCTT
CTATAAACCACCTGCGGGCTCAGATACCTACGAAGAGGCTCAGATAACTCAAGGACGTGCATTCG
AATTATCCCTGCCGCGCGGAAACATCAGACCAGGTGCGGATGCTGAGCGTCGAGTTGGGTGCTT
GATAGACCTTCACCTTGATCTGAGGTTCCCGTCCCCAGAGCACTCGAATCTCCGGCATCTTACAG
GCAAACCGCAAACAGTAAATAATGGCGAGCACCATCACCATGggtacccttgcagtgccccaaaaactggctac
cacctaacaattctcacgcagttttatcctctgcactttgatgtcagcttttgattcgtctgcgtacattacagcgttgagtggccagcaggaagga
gaccgcggtccgagacgagtctgagggcgcgctctcgcaacttggattccggatttcttaccctgcatcgacctcggcctggagtcgatcaga
aattgtcattgccagattgcctggcgaggacgggtgatatactcaaggcgttgcatcgcccacaaaacacacacttatctgcaagggagttact
gcatcaggctctgctcaacagctcgtgacatcgatcgttcagctccccagcaggtgcgtgtccgcatggagcacccctcccgagacacctgc
gttgggtgtcggaggagctcacatgccagggaggtgcccacattgcaccacgcgaccgcgaaataggcagacttcgggcatcctgtcatcg
catgtccgctggccgggaatcatggcctccccaccaggcgtcacgcgctgcccacctccctccccttgctgcgcagggcaccgcgttcctgtg
gagagccgaccac*ATGtccccccccaactccatgtccccgccaccaacggctccaccaacggcgtggccatcaacggcgccaagaa*
*gctgctggacttcgacccctccgccgcccccccttcaagatcgccgacatccgcgccgccatccccccccactgctgggtgaagaacccct*
*ggcgctccctgtcctacgtgctgcgcgacctgctggtgatcctgtccttcgccgtggccgccaccaagctggactcctggaccgtgtggcccctg*
*tactggatcgcccagggcaccatgttctgggccgtgttcgtgctgggccacgactgcggccacggctccttctccgactcctggctgctgaaca*
*acgtgatgggccacatcctgcactcctccatcctggtgccctaccacggctggcgcatctcccacaagacccaccaccagaaccacggcaa*
*cgtggagaaggacgagtcctgggtgcccctgcccgagaaggtgtacaagtccctggacaccggcaccaagttcatgcgcttcaccatcccc*
*ctgcccatgttcgcctaccccatctacctgtggcgccgctcccccggcaagaagggctcccacttcaacccctactccgacctgttcgcccca*
*acgagcgcacctccgtgatgatctccaccctgtgctggaccgccatggccctgctgctgtgctactcctccttcatctacggcttcctgcccgtgtt*
*caagatctacggcgtgccctacctgatcttcgtggcctggctggacatggtgacctacctgcaccaccacggctacgagcagaagctgccctg*
*gtacaggggcaaggagtggtcctacctgcgcggcggcctgaccaccgtggaccgcgactacggcgtgatcaacaacatccaccacgaca*

【FIG. 19B】

*tcggcacccacgtgatccaccacctgttcccccagatgccccactaccacctggtggaggccacccaggccgccaagcacgtgctgggca*
*agtactaccgcgagcccaagaagtccggcccctttccccttccacctgttcggctacctggtgcgctccctgggcgaggaccactacgtgtccg*
*acaccggcgacgtggtgttctaccagtccgacccccacatccccaagttccccacctccgccaccaccaagtccaagtcctcctgagTGA*T
CCGGGAGGAGGGAGTGAGCGGGGAAGGGGGCAGCCACACGGGGCCCGTCTCGACCTGCCACCCCTCCCCTCGTC
GAGCCCTGCCCAGGGGGCGCCGCAACGAGCCATGCGTGTGCATGTGTCTGGAGGGCCCTTCCACCGGGCGATGTG
CGAGCCATCCTCGCCTATTTCAACACACCGCTGCCGGCATGCGCTCCACTCCCCCCAAAACCACCTCGACCCTCCCA
GGGCTCCTCCCCCGCCCCACCCTGCCTGCTGATATAGAAACCAGTGTTCTGTGAACGTTTGACATGCTCAACGAGGG
TACAGGGGTGCACCAACAGAGGAGGAGTGGTTCACACAGTCGGATACactagtccttcctgtcccacaatgcttggtgaatgca
gtgggttgatcaccgcggaggagctgtggcttactcgttctgatcaagggagcctctgcaccttaaccctgccaggatcgaaaccaaccttgtc
agtcccgtggtgggcaacatcatcctcgtgaagctgattgaccaggaaaacatgatgagtcggtatgaggacgagcatgagtggcccaaca
tcgatatgacacatcttggagtttacggcaaatgtatcacacttccatcctggcttgcaccacaatattagtggacccctccttgcagtggcacggt
gagaagctagtttgtagtaatcttcttaattgacgaaccagacgtgtgtaatggcctcctttgagtgatggaaggatggaacctaccccccccctc
cccagtactctgcggtacatccgagtaacccttccattgatcagcccaaacgcaatatgcaacgactctacatacggccaccgagtgcttattc
cttcgctatcaccgcacaaaaatcccatccgcgaactcatccgaggtgatagattgcgatcggggttattcgggttaaggtgcgactagggatc
cctgaatcttttggggatttccccgggtctcgtcctgcatgcttatcatcagtctcgtgggttatttggatcgctgcgcatgccataacagagcgctca
taatatttgctgcggcggtggtgctggcaaaatcccctgcgtaccgggcgcctgtcaagccaaccccgccgtgcggcactcccctgcagatcc
atcacc*ATGatcgagcaggacggcctccacgccggctcccccgccgcctgggtggagcgcctgttcggctacgactgggcccagcagac*
*catcggctgctccgacgccgccgtgttccgcctgtccgcccagggccgccccgtgctgttcgtgaagaccgacctgtccggcgccctgaacg*
*agctgcaggacgaggccgcccgcctgtcctggctggccaccaccggcgtgccctgcgccgccgtgctggacgtggtgaccgaggccggcc*
*gcgactggctgctgctgggcgaggtgcccggccaggacctgctgtcctcccacctggcccccgccgagaaggtgtccatcatggccgacgc*
*catgcgccgcctgcacaccctggaccccgccacctgccccttcgaccaccaggccaagcaccgcatcgagcgcgcccgcacccgcatgg*
*aggccggcctggtggaccaggacgacctggacgaggagcaccagggcctggcccccgccgagctgttcgcccgcctgaaggcccgcat*
*gcccgacggcgaggacctggtggtgacccacggcgacgcctgcctgcccaacatcatggtggagaacggccgcttctccggcttcatcgac*
*tgcggccgcctgggcgtggccgaccgctaccaggacatcgccctggccacccgcgacatcgccgaggagctgggcggcgagtgggccg*
*accgcttcctggtgctgtacggcatcgccgcccccgactcccagcgcatcgccttctaccgcctgctggacgagttcttcTGA*GCTGTTCCT
AGGAACGTGGAGGAGGTGCAAGGAGGGTGATCTCACCCTGGTGTGTCTCTTCATGGAGCTCAGATCTTGAAAACTGT
GAGGTGCTTATCCGATACCTGCTTCGTGCATGGCTTGTGCGATATGTACACGCATTTGCAGATTGGTGGGAGCAGCAG
ATTGGTGGGAGCAGCATAGAGCTTTAGAAGGGGCTTAGGAGCGGGAATGTGAAACTCAGGCGGTTGGGCCAGATGA
GAGCGCAAAGggatccCAACGCTACGCAACTCCCTTCGATGGCTTCAAGTACGGAGATGTGGGCATC

【FIG. 19C】

CAGGATTCGCATGTGCTGCTTCAGCCCTCCTCATGCCACTAGCACTCATTTTTCGACTCCCGGAT
TGCCAGGTTCAAGGGCATCAAGGAGTCGGAGATCAGCCGCGCCATGACCTCCCGCTACTTCGAG
GACCTAAACGTCAATGCCGAGGTGCTTTTGCATATATTTACAGCTAATTATGATGGGTGTGGTGCG
CGATATGCTTGCAAGGTCTCCGGTGAGCTAATGATCGGCACATCCCTTCCGCGCATCCGCAGGTC
GATGTCGTCATTGTTGGGGCTGGGTCTGCGGGCCTCTCGTGCGCCTATGAGCTGAGCAAGCACC
CGGATGTCAAGGTATGGGCTGAGCAGGGCACATCCTCAGATGATGTTGCTGTAATTGCAATTGAA
ACTTGCGGTTGTTCCCAGCACAGCCTCAATCAATCATGTGTGCTGCGTTGGAAACGCTATGATAC
CCCAGCCTTCAACATGGGGCAGGGATATCGTTTACACCTGCTTGAACCCCCCGCAACAGGTGGC
CATCATCGAGCAGGGCGTCGCCCCTGGGGGTGGAGCGTGGCTGGGGGGTCAGCTCTTCTCGG
CTATGTGTGTGAGTCTAGGCACGGGGACGGGTGGACTGAAGCAAGGGTTGGGCGCAGGGTGTT
GATATCCATGTGTTGGACATTCTCGTTGGGAAAACAAGATGTGTGTATTTAGTGCTATCTCGGTGG
CTGCATTCCaagctt

【FIG. 20】

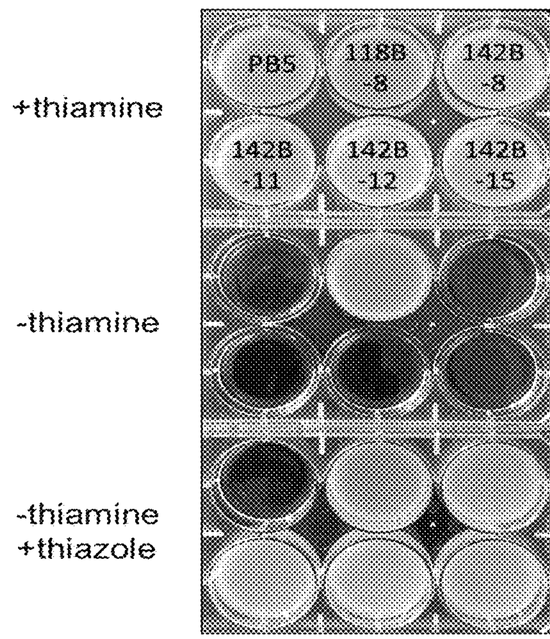

【FIG. 21】

*ATGgccaccgcctccctgcccgtgcaggtggccgtgacctccacccactgcttcggcctgcgcgagccccgccgcaagcg*
*ccagtgggcccgccagacccgctgccacgcctccgccgccggcaagcccaagcgccgcgtggtggtgaccggccagggc*
*gtggtgacctccctgggccagtccacccagcagttctacgaccagctgctggccggcgcctccggcatcacccacatcgagg*
*gcttcgacacctccgactactccaccaagatcgccggcgaggtgaagtccgtggacgccgcccccctacgtggcccgcaagt*
*gggtgaagcgcatggacgaggtgatgaagttcatgttcgtggccggcaagcaggccctggaggacgccggcctgcccttcg*
*agggccccggcctggaggacctggaccgcaagctgtgcggcatcctgatcggcaccgccatgggcggcatgaccaccttcg*
*cctccggcgtggaggccctgaccctgtccggccaccgcaagatgaaccccttctgcatccccttctccatcggcaacatgggc*
*ggcgccatgctggccatggacctgggcttcatgggccccaactactccatctccaccgcctgcgccaccggcaactactgcat*
*catctccgccgccgaccacatccgcaacggcgacgccgtgctgatgctggcgggcggcgccgacgccgccgtgatcccctc*
*cggcatcggcggcttcatcgcctgcaaggccctgtcccgccgcaacgacgcccccgagcgcgcctcccgcccctgggacgc*
*cggccgcgacggcttcgtgatgggcgagggcgccggcgtgctggtgctggaggagctggagcacgcccgcgcccgcggc*
*gccaccatcctggccgagttcatcggcggcgcggccacctgcgacgcccaccacatgaccgagcccgagccctccggccg*
*cggcgtgcgcctgtgcctggagcgcggcctggccgccgccggcgtggcccccgaggaggtgacctacgtgaacgcccacg*
*gcacctccacccccgccggcgacgtggccgagttccgcgccatccgcgccgtgctgggccacgacggcctgcgcatcaact*
*cctccaagggcgccatcggccacctgctgggcgcggcgggcgccgtggaggccgtggccaccatccaggccctgcgcacc*
*ggctggctgcaccccaacctgaacctggacgagcccgacaagggcgtggacgcctccgtgctggtgggcggcgtgaagga*
*gcaggccgacgtgaaggtggccctgtccaactccttcggcttcggcggccacaactcctgcgtgctgttccgcaagttcgagg*
*agTGA*

【FIG. 22】

MATASLPVQVAVTSTHCFGLREPRRKRQWARQTRCHASAAGKPKRRVVVTGQGVVTSL
GQSTQQFYDQLLAGASGITHIEGFDTSDYSTKIAGEVKSVDAAPYVARKWVKRMDEVMKF
MFVAGKQALEDAGLPFEGPGLEDLDRKLCGILIGTAMGGMTTFASGVEALTLSGHRKMNP
FCIPFSIGNMGGAMLAMDLGFMGPNYSISTACATGNYCIISAADHIRNGDAVLMLAGGADA
AVIPSGIGGFIACKALSRRNDAPERASRPWDAGRDGFVMGEGAGVLVLEELEHARARGAT
ILAEFIGGAATCDAHHMTEPEPSGRGVRLCLERGLAAAGVAPEEVTYVNAHGTSTPAGDV
AEFRAIRAVLGHDGLRINSSKGAIGHLLGAAGAVEAVATIQALRTGWLHPNLNLDEPDKGV
DASVLVGGVKEQADVKVALSNSFGFGGHNSCVLFRKFEE

PRODUCTION OF LIPIDS AND TERPENOIDS IN *AUXENOCHLORELLA PROTOTHECOIDES*

CROSS-REFERENCE TO RELATED APPLICATION

This application claims the benefit of U.S. Provisional Application No. 63/109,901 filed on Nov. 5, 2020, the disclosures of which are herein incorporated by reference in their entirety.

TECHNICAL FIELD

The present invention describes microalgae having a functional oil-producing ability comprising an altered profile of fatty acids, carotenoids and/or terpenoids and a method of extracting oil using the microalgae. More specifically, it relates to a method for producing oil having modified fatty acids, carotenoids and/or terpenoids content compared to wild-type microalgae, such as Auxenochlorella protothecoides with inhouse strain designation as PB5.

BACKGROUND ART

Industrial production of lipids and fats from oleaginous microorganisms has been investigated since the late 19th century, but the promise of these "single cell oils" has only been realized in the last 20-30 years[1]. Oleaginous microorganisms trigger biosynthesis of storage lipids in response to imbalances between carbon (C) supply and other major nutrients such as nitrogen (N) or phosphorus (P) that are required for growth. This response allows accumulation of excess C under conditions where limitation for other nutrients prevents cell growth and division. Microbial storage lipids are largely composed of triacylglycerides (TAGs), which can be mobilized and used for rapid growth when the limiting nutrient or nutrients become available. Subsets of yeasts, fungi, and algae, but very few bacteria are oleaginous[1]. In the case of some algae, oil production can be stimulated by photosynthesis or by heterotrophic fermentation of sugars, but there is little economic incentive to make lipids which have similar composition or properties to commodity plant oils. In the early 2000s there was a flurry of interest and investment in photosynthetic production of biofuels from algae, but this has now largely faded due to the unfavorable energy return and economics of fuel production from aquatic microbes[2,3]. Heterotrophic oil productivity is substantially higher than is the case for photoautotrophic production, but the price of common sugar feedstocks is seldom any less that one quarter of the price of typical commodity oils, and the lipid yield for most heterotrophic processes is less than 25%. The economics can improve if the carbon source comes from a low value waste stream (e.g., lactose from cheese production, cellulosic sugars from agricultural waste).

On the other hand, heterotrophic production of very long chain polyunsaturated fatty acids (VLCPUFAs) from algae, thraustochytrids and yeasts provides a roadmap for successful commercialization of microbial oils. Docosahexaenoic acid (DHA) from the dinoflagellate algae *Crypthecodinium cohnii* and arachidonic acid (ARA) from the yeast *Mortierella alpina* are both important components of infant formula[1]. These fatty acids are important components of human breast milk and are vital for brain and nervous system development[4]. The microbial oils address a particular market need for which there are no appropriate substitutes, since the only other significant sources of VLCPUFAs come from fish oils which are subject to contamination with toxins and heavy metals.

Other successful commodity products from aquatic microalgae follow the VLCPUFA model. Astaxanthin and beta-carotene are key carotenoids for human nutrition; the former is one of the most powerful antioxidants known, while beta-carotene also has strong antioxidant activity and is a pro-vitamin A supporting vision[5]. Synthetic astaxanthin derived from petrochemicals is used extensively as a colorant in fish farming but is not approved for human consumption in food or supplements. The major natural source of astaxanthin is the chlorophyte *Haematococcus lacustris* (also *H. pluvalis*), which is grown photoautotrophically in ponds or bioreactors. *Haematococcus* cultures can produce up to 5% of their biomass as astaxanthin when they are subjected to nutrient and high light stress. Astaxanthin is also produced commercially by the heterotrophic fermentation of the yeast *Phaffia rhodozyma*, but the carotenoid content of the biomass is much lower than *Haematococcus*[6,7]. Natural beta-carotene is extracted from another chlorophyte, the halophile *Dunaliella salina*, which is grown photoautotrophically in large salt ponds. Both *Haematococcus* and *Dunaliella* fetch high prices for the biomass, but photoautotrophic cell densities are too low and the production costs for harvesting and extraction are too high for the natural sources to reach the scale where they can compete with synthetic carotenoids.

Squalene is an important component of human sebum (12%), a fact that justifies its role in the physiology of skin[8], its action in skin hydration, repairing of the damaged skin, and rejuvenating the aging skin was demonstrated. The emollient and hydration properties of squalene and its biocompatibility with skin make squalene an important component in cosmetic formulations (moisturizing creams, makeup, lipstick, and nail and hair products).

Furthermore, squalene appears to play an essential role in protecting skin from free radical oxidative damage. Squalene acts in skin as a quencher of singlet oxygen, protecting by this mechanism the skin surface from lipid peroxidation due to exposure to UV light.

Squalene has been known to play diverse biological roles as an antioxidant[9,10], anti-cancer agent[10,11], age defyer[12,13] chemo preventive agent[14,15,16], antibacterial agent[13,17], adjuvant for vaccines and drug carrier[18,19], and detoxifier[11,20] among others.

Squalene has proved to be a well-tolerated, non-toxic cytoprotective agent that mitigates undesirable side effects of cancer chemotherapy. Many anticancer therapies damage normal healthy tissues, even to the point of organ toxicity. These toxic secondary effects can limit the anticancer drug dosage, and even lead to treatment failure. Squalene is effective at scavenging and detoxifying free radicals produced by chemotherapeutic or radiation therapy agents.

The role of squalene is not just confined to these applications, but it is also a precursor to thousands of bioactive molecules, including steroids and hopanoids. Consequently, many chemicals, food, cosmetic, and pharmaceutical industries have started to use squalene extensively. It also acts as a boosting agent, or adjuvant, that improves the immune system and makes vaccines more effective. Over the last decade, global squalene demand has increased and gained much public and scientific attention. In 2014, the global squalene market demand was about 2.67 kilotons[21], with a projected value of 241.9 million USD by 2022, with major revenues expected from the personal care and cosmetic products[22]. In order to fulfill this ever-increasing demand of squalene, a pressing need has arisen to produce squalene in a renewable and sustainable manner.

Squalene is harvested from deep-sea sharks and exists in high concentration in shark liver. However, the intensive fishing of these sharks puts in danger the existence of these species, with many of them being close to extinction as their reproductive cycle is quite long and the growth is slow.

Most plant seed oils contain small amounts of squalene[23]. This phytosqualene has superior qualities compared to shark squalene, in that it is highly stable, generally free of heavy metal contamination, odorless, and colorless. In spite of containing significant amounts of squalene, plants oils are not ideal sources. Some plants are strictly seasonal, and squalene content varies greatly geographically. Oilseed crops require the appropriate climatic conditions, soil quality, scheduled irrigation or sufficient rainfall, fertilizer, and pest management. The process of cultivation is labor intensive and correspondingly the amount of squalene produced from plant sources is not sufficient to fulfill the increasing worldwide demand.

Several microalgae and other microorganisms accumulate comparable levels of squalene to plant oils. Short generation times and ease of genetic engineering make microalgae a better alternative for squalene production than plants.

Native biosynthetic pathways which include squalene as an intermediate are present in many microalgae, and these pathways can be transformed or extended to convert the organisms into "cellular factories" for squalene production.

Auxenochlorella protothecoides is one of the most oleaginous species of microalgae and can be cultivated heterotrophically with productivity in commercial scale[24]. Metabolic engineering using genetic tools on this organism has strong potential to produce variety products including carotenoids, terpenoids, and other active ingredients, which can be an important alternative source of currently depleted natural resources.

BRIEF SUMMARY OF THE INVENTION

The inventors of the present application have developed the Trebouxiophyte alga, Auxenochlorella protothecoides PB5, as a biotechnology platform for the heterotrophic production of valuable lipids, carotenoids, terpenoids, and other compounds. Efficient transformation and facile gene targeting by homologous recombination are features of this system. Targeted knockouts and knock-ins of fatty acid and lipid biosynthetic pathway genes enabled the improved synthesis of polyunsaturated fatty acids. Valuable ketocarotenoids were produced by disrupting endogenous carotenoid biosynthetic genes and expressing heterologous beta-carotene ketolase transgenes. Squalene accumulation was increased by blocking phytosterol biosynthesis. *A. protothecoides* PB5 can be employed as a general platform for the photoautotrophic, mixotrophic, or heterotrophic production of valuable biomolecules. Here the inventors of the present application demonstrate the utility of the system for the biosynthesis of modified fatty acids, lipids, carotenoids, and other terpenoids (FIG. 1).

It is an object of the present invention to provide mutant microalgae having functional oil-producing ability comprising modified profiles of fatty acids, carotenoids and/or terpenoids as proposed to solve the above problems.

Another object of the present invention is to provide a method for producing oil using the microalgal mutant.

Another object of the present invention is to provide oil prepared by the above production method.

Advantageous Effects

The present application shows that when using a microalgal mutant in which Auxenochlorella protothecoides PB5 microalga genes are knocked out or knocked in by homologous recombination, an oil containing fatty acids, carotenoids and/or terpenoids of an altered profile compared to that of wild type thereof can be effectively extracted.

DESCRIPTION OF THE DRAWING

FIG. 1 shows a diagram of the Isoprenoid pathway, an essential metabolic pathway present in microalgae.

FIGS. 2A-B show the sequence of the transforming DNA from the LCYE-1 disruption construct pPB0014. (SEQ ID NO: 1)

FIGS. 3A-C show the sequence of the transforming DNA from the LCYE-2 disruption construct pPB0038. (SEQ ID NO: 2)

FIGS. 4A-D show spectrophotometric and HPLC analysis of carotenoid pigments from wild-type *A. protothecoides* PB5, 14-2, and 38-25. Absorbance spectra of acetone-methanol-extracted pigments from wild-type *A. protothecoides* PB5, LCYE-1 disruption strain 14-2, and LCYE-1/LCYE-2 double knockout strain 38-25. Peak absorbances are indicated for each curve (FIG. 4A). HPLC chromatograms showing carotenoid pigments present in oil extracted from the same strains as in A (FIG. 4B: PB5, FIG. 4C: 14-2, FIG. 4D: 38-25).

FIG. 5 shows the sequence of the expression module cloned into the KpnI site of pPB0038 to generate construct pPB0120. (SEQ ID NO: 3)

FIG. 6. Nucleotide sequence of the ApSAD2tp_CrBKT1 expression module from pPB0123. (SEQ ID NO: 4)

FIG. 7A shows the amino acid sequence of native CrBKT1. The predicted plastid transit peptide is underlined. (SEQ ID NO:5)

FIG. 7B shows the amino acid sequence of chimeric ApSAD2tp_CrBKT1. The predicted ApSAD2 plastid transit peptide is underlined. (SEQ ID NO:6)

FIGS. 8A-E show shake flask cultures illustrating the color differences due to engineered alterations in the carotenoid profiles (FIG. 8A). HPLC chromatograms showing carotenoid pigments present in oil extracted from the same strains as in A (FIG. 8B: 120A-2, FIG. 8C: 123A-5, FIG. 8D: 120B-5, FIG. 8E: 123B-24).

FIGS. 9A-C show the sequence of the transforming construct pPB0065, targeting disruption of ApSQE-2. (SEQ ID NO: 7)

FIGS. 10A-B show the sequence of the transforming DNA from pPB0077. (SEQ ID NO: 8)

FIG. 12 shows the amino acid sequence of *A. protothecoides* 1-deoxy-D-xylulose 5-phosphate synthase (DXS). The predicted plastid transit peptide is underlined. (SEQ ID NO:9)

FIG. 13 shows the amino acid sequence of *A. protothecoides* 1-deoxy-D-xylulose 5-phosphate reductoisomerase (DXR). (SEQ ID NO:10)

FIG. 14 shows the amino acid sequence of *A. protothecoides* farnesyl diphosphate synthase (FDPS). (SEQ ID NO:11)

FIG. 15 shows the amino acid sequence of *A. protothecoides* squalene synthase (SQS). (SEQ ID NO:12)

FIGS. 16A-C show the sequence of the transforming construct pPB0039, targeting insertion of the ApSAD2 promoter upstream of the FAD3-1 coding sequence. (SEQ ID NO: 13)

FIG. 17 shows the nucleotide sequence of the ApFATA promoter in pPB0041 SEQ ID NO: 14)

FIGS. 18A-C show the sequence of the transforming construct pPB0118, targeting AtPDCT and ScSUC2 expression to the THI4 locus. (SEQ ID NO: 15)

FIGS. 19A-C show the sequence of the transforming construct pPB0142, targeting LuFAD3A and neoR expression to the THI4 locus. (SEQ ID NO: 16)

FIG. 20 shows the growth of strains targeting one or both alleles of THI4. Wild-type *A. protothecoides* PB5 is unable to grow without added thiamine. Thiamine prototrophy is observed in strain 118B-8, expressing AtTHIC, targeted to one allele of THI4. Disruption of the second THI4 allele by pPB0142 renders the transformants thiazole auxotrophs.

FIG. 21 shows the coding sequence of KASII from *A. protothecoides*, optimized for translation. (SEQ ID NO:17)

FIG. 22 shows the amino acid sequence of *A. protothecoides* beta-ketoacyl-ACP synthase II. (SEQ ID NO:18)

DETAILED DESCRIPTION OF THE INVENTION

Figure 8A:
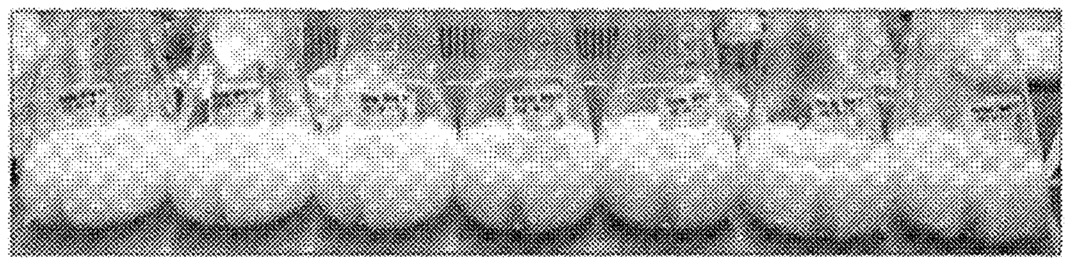

Unless otherwise defined herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner like a term "comprising." The transitional terms/phrases (and any grammatical variations thereof) "comprising," "comprises," "comprise," "consisting essentially of," "consists essentially of," "consisting," and "consists of" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the value as determined by one of ordinary skills in the art, which will depend in part on how the value is measured or determined, i.e., the limitations of the measurement system. Where values are described in the application and claims unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

An "allele" refers to a version of a gene at the same place on homologous chromosomes. An allele may encode the same or similar protein.

"Exogenous gene" shall mean a nucleic acid that codes for the expression of an RNA and/or protein that has been introduced into a cell (e.g., by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Fixed carbon source" is a molecule(s) containing carbon, typically an organic molecule that is present at ambient temperature and pressure in solid or liquid form in a culture media that can be utilized by a microorganism cultured therein. Accordingly, carbon dioxide is not a fixed carbon source.

"Microalgae" are eukaryotic microbial organisms that contain a chloroplast or other plastid, and optionally that can perform photosynthesis, or a prokaryotic microbial organism capable of performing photosynthesis. Microalgae include obligate photoautotrophs, which cannot metabolize a fixed carbon source as energy, as well as heterotrophs, which can live solely off a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis.

In connection with a recombinant cell, the term "knockdown" refers to a gene that has been partially suppressed (e.g., by about 1-95%) in terms of the production or activity of a protein encoded by the gene.

Also, in connection with a recombinant cell, the term "knockout" refers to a gene that has been completely or nearly completely (e.g., >95%) suppressed in terms of the production or activity of a protein encoded by the gene. Knockouts can be prepared by ablating the gene by homologous recombination of a nucleic acid sequence into a coding sequence, gene deletion, mutation, or other methods. When homologous recombination is performed, the nucleic acid that is inserted ("knocked-in") can be a sequence that encodes an exogenous gene of interest or a sequence that does not encode for a gene of interest.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous (especially eukaryotic microalgae that store lipid). An oleaginous cell also encompasses a cell that has had some or all its lipid or other content removed, and both live and dead cells.

In connection with a functional oil, a "profile" is the distribution of species or triglycerides or fatty acyl groups within the oil. A "fatty acid profile" is the distribution of fatty acyl groups in the triglycerides of the oil without reference to the attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of fatty acid in the total fatty acid signal determined from the area under the curve for that fatty acid.

"Recombinant" is a cell, nucleic acid, protein, or vector that has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of the active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The terms "triglyceride", "triacyl glyceride" and "TAG" are used interchangeably as is known in the art.

In the present disclosure, ranges are stated in shorthand, to avoid having to set out at length and describe each value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. When ranges are used herein, combinations and sub-combinations of ranges (e.g., subranges within the disclosed range), specific embodiments therein are intended to be explicitly included.

According to one aspect of the present invention, a method for producing oil comprising a fatty acid, carotenoid, and/or terpenoid of a modified profile using a gene knockout or knock-in microalgal mutant by homologous recombination is provided.

According to one aspect of the present invention, a method for producing oil, characterized in that the weight ratio of zeaxanthin to lutein is high compared to the oil produced from wild-type microalgae, is provided.

According to one aspect of the present invention, a method for producing an oil comprising astaxanthin is provided.

According to one aspect of the present invention, a method for producing an oil comprising squalene is provided.

According to one aspect of the present invention, a method for producing a functional oil, characterized in that the weight ratio of omega-6 to omega-3 is low compared to the oil produced from wild-type microalgae, is provided. Preferably, the ratio of the oil ranges between 1:1 to 5:1 compared to the oil produced from the wild type microalgae which is 7:1.

According to one aspect of the present invention, a method for producing a functional oil, characterized in that the omega-3 fatty acids increased 3-5-fold and the overall PUFA increased 2-3-fold compared to the wild-type strain.

According to one aspect of the present invention, the microalgal mutant may be a gene knockout or knock-in microalgal mutant by homologous recombination. Preferably, the microalgae may be *Auxenochlorella* genus, more preferably, Auxenochlorella protothecoides PB5.

According to one aspect of the present invention, the microalgae mutant is to provide a method for producing functional oil, characterized in that one or more of the alleles LCYE-1 and LCYE-2 of the Lycopene Cyclase Epsilon gene are knocked out.

According to one aspect of the present invention, the microalgal mutant strain may be to provide a method for producing a functional oil, characterized in that one or more of the alleles SQE-1 and SQE-2 of the Squalene Epoxidase gene are knocked out.

According to one aspect of the present invention, the microalgal mutant may be to provide a method for producing a functional oil, characterized in that the native FAD3 promoter is replaced with a Stearoyl-ACP Desaturase (SAD2) promoter, or the native FAD3 promoter is replaced with an acyl-ACP thioesterase (FATA) promoter.

According to one aspect of the present invention, it may be to provide the use of microalgae as a platform to produce functional oils comprising fatty acids, carotenoids, and/or terpenoids of altered profile by modification of the isoprenoid pathway.

According to an aspect of the present invention, it may be to provide a mutant microalga for the production of oil containing fatty acids, carotenoids, and/or terpenoids of an altered profile.

According to an aspect of the present invention, it may be to provide an oleaginous microalgae mutant that produce a functional oil, the microalgae comprising an ablation of one or more alleles of an endogenous polynucleotide or comprising an exogenous gene.

According to one aspect of the present invention, the microalgal mutant is a microalgal mutant knocked out or knocked-in by homologous recombination, preferably, at least one of the alleles LCYE-1 and LCYE-2 of lycopene cyclase epsilon characterized by knocking out, or knocking out at least one of alleles SQE-1 and SQE-2 of squalene epoxidase, or replacing the native FAD3 promoter with a Stearoyl-ACP Desaturase (SAD2) promoter or a mutant strain in which the native FAD3 promoter is replaced with the promoter of the *A. protothecoides* FATA gene encoding acyl-ACP thioesterase.

Hereinafter, the present invention will be explained in detail.

As an aspect for achieving the object of the present invention, the present invention provides an Auxenochlorella protothecoides mutant for producing a fatty acid, a carotenoid, or terpenoid having a modified profile.

As an embodiment, the Auxenochlorella protothecoides mutant may be a mutant of *A. protothecoides* PB5.

The Auxenochlorella protothecoides mutant of the present invention may be prepared using general mutation treatment methods.

In the present invention, "mutation" refers to a change in a nucleotide sequence due to the insertion, deletion, or substitution of a base into the original nucleotide sequence.

As a means of mutation, the number of inserted bases may be different depending on the mutation and thus is not limited thereto. "Deletion mutation" means a mutation in which a base is removed from the original nucleotide sequence, and "substitution mutation" means that an original nucleotide is changed to another base without changing the number in the original nucleotide sequence.

In a specific embodiment of the present invention, pPB0014 has a transforming DNA with the nucleotide sequence of SEQ ID NO: 1 which is a DNA construct in which LCYE-1 encoding one allele of Lycopene Cyclase Epsilon in Auxenochlorella protothecoides PB5 is prepared in order to change the ratio of lutein derived from alpha-carotene and zeaxanthin derived from beta-carotene compared to wild type. Then, strain 14-2 was prepared by introducing pPB0014. Afterward, in order to generate a double knockout strain completely lacking lutein, a carotenoid derived from alpha-carotene, pPB0038, a DNA construct having a transforming DNA with the nucleotide sequence of SEQ ID NO: 2, in which LCYE-2 encoding the second allele of Lycopene Cyclase Epsilon was prepared. The mutant strain 38-25 is prepared by transforming the strain 14-2 with said pPB0038.

It was confirmed that the above strains increased the ratio of zeaxanthin to lutein compared to the wild type.

In a further embodiment, to prepare a keto-carotenoid, an expression module for *C. reinhardtii* beta-carotene ketolase1 (CrBKT1) SEQ ID NO: 4, was introduced into the pPB0038 backbone to produce construct pPB0123, which targeted the LCYE-2 single allele. Alternatively, strains in which LCYE alleles were disrupted were prepared. In addition, when a single LCYE allele is knocked out, 4-keto-lutein and astaxanthin are produced, while when both LCYE alleles are knocked out strains almost exclusively produced astaxanthin.

In a specific embodiment of the present invention, to obtain squalene, ApSQE-2 encoding the Squalene Epoxidase allele 2 in Auxenochlorella protothecoides PB5 is knocked out. DNA construct having a transforming DNA with the nucleotide sequence of SEQ ID NO: 7 pPB0065 was prepared and introduced into wild-type Auxenochlorella protothecoides PB5 to prepare strain 65-4. Then, in order to generate a double knockout strain, pPB0077, a DNA construct having nucleotide sequence SEQ ID NO: 8 was constructed and transformed into the strain 65-4 in which SQE-1 encoding Squalene Epoxidase allele 1 was knocked out. The prepared mutant strain was named strain 77B-21.

It was confirmed that the above strains can accumulate squalene while the wild type cannot.

In a specific embodiment of the present invention, the native FAD3 promoter in *A. protothecoides* PB5 is replaced with a promoter of a gene that is strongly up-regulated during lipid production, thereby activating the endogenous FAD3 gene encoding Fatty acid Desaturase 3 to reduce the ratio of omega-6 to omega-3 compared to the wild type. Specifically, construct pPB0039 having a transforming DNA with the nucleotide sequence of SEQ ID NO: 13 was constructed in which the ApSAD2 promoter was inserted upstream of the FAD3-1 coding sequence. Alternatively, construct pPB0041 was constructed, in which the native FAD3 promoter was replaced with the promoter of the FATA gene encoding acyl-ACP thioesterase SEQ ID NO: 14. Plasmid construct pPB0039 and pPB0041 were introduced into wild-type *A. protothecoides* PB5 to obtain strains 39-1 and 39-9 strains 41-1 and 41-3, respectively. It was confirmed that the strains increased the ratio of omega 3 to omega 6 compared to the wild type.

In a specific embodiment of the present invention, transfer of C18:1 between DAG and phospholipids was improved by transforming a construct, pPB0118 SEQ ID NO:15, encoding *Arabidopsis* phosphatidylchloline:diacylglycerol choline phosphotransferase (PDCT) into strain 41-3. As a result, C18:2 accumulation increased by 2.5-fold in strains 118B-8 and 118B-20, indicating that expression of AtPDCT during lipid production caused significant enhancement of FAD2 activity, and the incorporation of C18:2 into TAG was favored over desaturation by FAD3.

In a specific embodiment of the present invention, the accumulation of fatty acids C18:3 (ALA) was increased by the introduction of a construct, pPB0142 SEQ ID: NO:16, encoding heterologous (*Linum usitatissimum*) FAD3A into strain 118B-8. As a result, ALA accumulation increased about 3% in strain 142B-11.

Auxenochlorella protothecoides PB5 is a superior system for generating engineered microalgae strains due to its ease of transformation and facile homologous recombination that does not require riboprotein-mediated gene editing. PB5 has a higher intrinsic capacity than non-photosynthetic heterotrophic platforms for production of carotenoids and other terpenoids due to the high flux through these biosynthetic pathways during photosynthetic growth.

The Mutants of the present invention are more industrially useful in that they may provide oils having fatty acids, carotenoids, and squalene content of a profile different from that produced in wild-type Auxenochlorella protothecoides.

In some cases, the percent (w/w) of zeaxanthin in the carotenoids produced by using the microalgal mutants of the present invention is 2-3-fold higher compared to the wild-type microalgae and the zeaxanthin is present as a major carotenoid. In a specific embodiment, the percent of zeaxanthin produced ranges between 40 to 90% (w/w) of the total identified carotenoids.

In some cases, the oil produced may contain keto carotenoids, such as the mixture of keto lutein, and astaxanthin, and the astaxanthin is present as a major carotenoid. In a specific embodiment, the percent of keto carotenoids produced ranges between 20-90% (w/w) of the total identified carotenoids.

In some cases, the oil produced may contain squalene. In a specific embodiment, the amount of squalene in the oil produced ranges from 300 to 1300 ppm.

In some cases, the weight ratio of omega-6 to omega-3 in the oil produced by using the microalgal mutants of the present invention is low compared to the oil produced from wild-type microalgae which are 7:1. In a specific embodiment the percent ratio of omega-6 to omega-3 in the oil produced ranges from 1:1 to 5:1.

The mutant of the present invention may grow appropriately in a growth environment (light conditions, temperature conditions, medium, etc.) capable of culturing conventional Auxenochlorella protothecoides.

The mutant of the present invention may be cultured according to the culture conditions of general Auxenochlorella protothecoides, and specifically, a culture medium capable of culturing algae under weak light conditions may be used. To culture a specific microorganism, it may include a nutrient material required for a culture target, that is, a microorganism to be cultured, and may be mixed by adding material for a special purpose. The medium includes an all-natural medium, synthetic medium, or selective medium. The Auxenochlorella protothecoides mutant may be cultured according to a conventional culture method.

The pH of the culture medium is not particularly limited if the Auxenochlorella protothecoides may survive and grow, for example, it is viable at pH 5 or higher, specifically at pH 6 to 8.

The Auxenochlorella protothecoides mutant of the present invention may produce modified profiles of fatty acids, carotenoids, and terpenoids in cells, so that oils extracted from mutants of the present invention may be effectively used as raw materials for pharmaceuticals, cosmetics, food, feed, etc.

In this aspect, the present invention provides a composition comprising the oil derived from the Auxenochlorella protothecoides mutant. The composition may be a cosmetic composition, a food composition, a composition for a food additive, a feed composition, a composition for a feed additive, a pharmaceutical composition, a raw material composition for food, a raw material composition for feed, a raw material composition for pharmaceutics or a raw material composition for cosmetics.

The composition may be used as a raw material for food, feed or pharmaceutics, and may be used as a formulation for oral administration or parenteral administration. For example, it may be used as a formulation for oral, transdermal or injection administration. Accordingly, the composition of the present invention may be a composition for oral administration in that the composition may be orally supplied to be included in food, medicine, or feed.

In the case of compositions for oral administration may be formulated as powders, granules, tablets, pills, dragees, capsules, liquids, gels, syrups, slurries, suspensions, etc. by using methods known in the art. For example, oral preparations may be obtained by mixing the active ingredient with excipients, grinding the mixture, adding suitable additives, and processing it into a granule mixture to obtain tablets or sugar tablets. Examples of suitable excipients include sugars, including lactose, dextrose, sucrose, sorbitol, mannitol, xylitol, erythritol and maltitol, and starches, including corn starch, wheat starch, rice starch and potato starch, cellulose, including methylcellulose, sodium carboxymethylcellulose, and hydroxypropylmethyl-cellulose, and the like, fillers such as gelatin, polyvinylpyrrolidone, and the like may be included. In addition, cross-linked polyvinylpyrrolidone, agar, alginic acid, or sodium alginate may be added as a disintegrant if necessary.

The composition may be used for human and animal health promotion. Specifically, the mutant of the present invention has oil production ability with enhanced antioxidant pigment content, so it is not easily oxidized, and functionally, it is possible to provide an oil superior to conventional microalgae-derived vegetable oil in antioxidant activity, and it can be effectively used as a raw material for health functional food, feed, or medicine.

In addition, since the composition may be added to food or feed to achieve a special purpose use, in this respect it may be a food composition, a composition for food additives, a feed composition or a composition for feed additives. When the composition is used in feed or food, it is possible to maintain or enhance body health by pigments and lipids including zeaxanthin produced by the mutant and accumulated in cells.

In the present invention, “additive” is included as long as it is a material added to food or feed other than the main raw material, and specifically, it may be an effective active material having functionality in food or feed.

In the present invention, the composition for feed may be prepared in the form of fermented feed, compounded feed, pellet form, and silage. The fermented feed may include a functional oil derived from the mutant of the present invention, and additionally include various microorganisms or enzymes.

The composition is mixed with a carrier commonly used in the food or pharmaceutical field, such as tablets, troches, capsules, elixirs, syrups, powders. It can be prepared and administered in the form of powder, suspension, or granules. As the carrier, binders, lubricants, disintegrants, excipients, solubilizers, dispersants, stabilizers, suspending agents, and the like may be used. The administration method may be an oral, or parenteral method, but preferably oral administration. In addition, the dosage may be appropriately selected according to the absorption of the active ingredient in the body, the inactivation rate and excretion rate, the age, sex, condition of the subject, and the like. The pH of the composition can be easily changed according to the manufacturing conditions of the drug, food, cosmetics, etc. in which the composition is used.

The composition may include 0.001 to 99.99% by weight, preferably 0.1 to 99% by weight of any one selected from the group consisting of the microalgal mutants of the present invention, the culture of the mutants, the dried product of the mutant, or the culture thereof, and the extract of the mutant or the culture thereof, and the functional oil derived from the mutant, based on the total weight of the composition, and the method of using the composition and the content of the active ingredient may be appropriately adjusted according to the purpose of use.

The mutant may be included in the composition in its own or dried form, and the culture of the mutant may be included in the composition in a concentrated or dried form. In addition, the dried product refers to the dried form of the mutant or its culture and may be in the form of a powder prepared by freeze-drying or the like.

In addition, the extract means that obtained by extraction from the mutant of the present invention, its culture medium or its dried product, an extract using a solvent, etc. Thus, the mutant of the present invention includes those obtained by crushing the mutant of the present invention. Specifically, the oil with the modified profile accumulated in the cells of the mutant of the present invention may be extracted and separated by a physical or chemical method.

In addition, the method for producing oil with the modified profile according to the present invention may include culturing the mutant of the present invention. In addition, the production method may further include; after the culturing step, isolating the mutant of the present invention from the culture.

The culture may be performed in a medium of pH 5.0 to 8.0 conditions. In addition, it may be carried out under a weak light condition, specifically, a light intensity condition in the range of 0.1-1, 1-3, or 3-5 μmol photons/$m^2$ s.

The production method may further include, in addition to the culturing step, a concentration step to increase the content of algae after culturing, and a drying step of drying by further reducing the moisture of the algae that has undergone the concentration step. However, the concentration step or the drying step is not necessarily required, and in general, the concentration and drying method commonly used in the field to which the present invention pertains, and it can be carried out using a machine.

The production method may further include the step of purifying the material isolated from the culture, which may be performed by a conventional purification method in the art to which the present invention pertains.

DETAILED DESCRIPTION OF THE EMBODIMENTS

Hereinafter, the present invention will be explained in detail through Examples and Experimental Examples, but these Examples and Experimental Examples are presented only as of the illustration of the present invention, and the scope of the present invention is not limited thereby.

The oleaginous Trebouxiophyte alga, Auxenochlorella protothecoides, stores copious amounts of triacylglyceride oil under conditions where the nutritional carbon supply is in excess, but cell division is inhibited due to the limitation of other essential nutrients.

Heterotrophically grown *Auxenochlorella* strains also degrade chlorophyll and down-regulate photosynthesis but maintain significant levels of the yellow carotenoids lutein and zeaxanthin. Bulk biosynthesis of fatty acids with carbon chain lengths up to C18 occurs in the plastids; fatty acids are then exported to the endoplasmic reticulum where incorporation into triacylglycerides (TAGs) occurs. Lipids are stored in large cytoplasmic organelles called lipid bodies until environmental conditions change to favor growth, whereupon they are rapidly mobilized to provide energy and carbon molecules for anabolic metabolism. Wild-type *A. protothecoides* storage lipid is comprised mainly of oleic (~68%), palmitic (~12%), and linoleic (~13%) acids, with minor amounts of stearic, myristic, α-linolenic, and palmitoleic acids. This fatty acid profile results from the relative activities and substrate affinities of the enzymes of the endogenous fatty acid biosynthetic pathway. *A. protothecoides* is amenable to manipulation of fatty acid and lipid biosynthesis using molecular genetic tools, enabling the production of oils with fatty acid profiles that are very different from the wild-type composition. Similarly, the carotenoid and phytosterol profile of the lipid fraction can be altered by genetic engineering of terpenoid biosynthesis pathways.

We have demonstrated efficient transformation and facile nuclear gene targeting via homologous recombination in *A. protothecoides*, PB5. In the following examples, we leverage our ability to perform gene knockouts and knock-ins to produce algal oils with modified fatty acid, carotenoid, and terpenoid profiles.

Wild type *A. protothecoides* PB5 was obtained from the University of Texas Culture Collection of Algae (UTEX catalog number 250), and it is available to the public to purchase via webpage www.utex.org.

Example 1. Production of Strains with Altered Carotenoid Profiles

Lutein is the predominant carotenoid that accumulates in heterotrophic *A. protothecoides* cells. To alter the ratio of lutein (derived from alpha-carotene) to zeaxanthin (derived from beta-carotene) we made a DNA construct to disrupt LCYE-1, encoding one allele of lycopene cyclase epsilon in *A. protothecoides* PB5. In general, flanking regions, promoters, and terminator sequences were PCR amplified from PB5 genomic DNA, and codon-optimized synthetic genes were amplified from plasmid DNA. Herculase II Fusion Enzyme (Agilent, USA) was used for PCR amplification. 50 ml amplification reactions contained 100-500 ng genomic DNA template, 250 micromolar dNTPs, 0.25 micromolar primers, and 0.5 ml Herculase II fusion DNA polymerase. Initial denaturation was at 95° C. for 2 minutes or at 98° C. for 4 minutes for highly GC-enriched templates. PCR products were amplified using 30-35 cycles of 95° C. or 98° C., 20 seconds, 55-65° C. annealing for 20 seconds, and extension at 72° C. for 30 seconds per kb. The sequence of the transforming DNA from the LCYE-1 disruption construct pPB0014 is shown below in FIG. 2.

Relevant restriction sites used to generate linear DNA and for cloning are indicated in lowercase, bold, and are from 5'-3' HindIII, KpnI, SacI, and HindIII. Underlined sequences at the 5' and 3' flanks of the construct represent genomic DNA from *A. protothecoides* PB5 that enable targeted integration of the transforming DNA via homologous recombination at the LCYE-1 locus. Proceeding in the 5' to 3' direction, the *Chlamydomonas reinhardtii* TUB2 promoter (CrTUB2') driving the expression of the *Saccharomyces cerevisiae* SUC2 gene (ScSUC2, codon-optimized for expression in *A. protothecoides* and encoding sucrose invertase, thereby enabling the strain to utilize exogenous sucrose) is indicated by lowercase, boxed text. The initiator ATG and terminator TGA for ScSUC2 are indicated by uppercase italics, while the coding region is indicated with lowercase italics. The terminator region of the *A. protothecoides* enolase gene (ApPGH) gene is indicated by small capitals.

Construct pPB0014 was introduced into *A. protothecoides* PB5 using a modified lithium acetate transformation procedure. Briefly, 50 mL of seed growth medium containing 2% glucose in 250 mL Erlenmeyer flask was inoculated with a loop of cells from a plate. Cultures were grown for 2 days at room temperature on an orbital shaker at 140 rpm, to an OD 750 nm 2-4. 50 ml of cell culture was harvested in a Falcon tube and centrifuged for 5 minutes at 3750 rpm. The cell pellet was washed once with 5 ml wash solution (0.1 M Lithium acetate (LiAc) and 1×TE (10 mM Tris, 0.1 mM EDTA) buffer and centrifuged to discard the supernatant. The cells were resuspended in 500 μl wash solution, transferred to a sterile Eppendorf tube, and incubated for 1 hour on a rotary shaker at room temperature at 150 rpm. For each transformation, 150 μl of cell suspension was aliquoted into a 1.5 ml Eppendorf tube. 5-20 μg of linearized DNA was added to the cell suspension, then incubated for 30 minutes at room temperature at 150 rpm. 750 μl of PEG solution (0.1 M LiAc, 1×TE, 40% PEG-4000) was added to the Eppendorf tube, and transformations were incubated overnight on the shaker at room temperature at 150 rpm. Cells were harvested by centrifugation at 5000 rpm for 30 seconds and resuspended in 250 μl of 1 M sorbitol. About 180 ul of the transformation was spread on growth media plates with 1.5% agar with selection, using glass beads, and incubated at room temperature for 1 to 2 weeks. Single colonies were observed on the agar plate after 5-6 days of plating.

Primary transformants were selected for heterotrophic growth on media with sucrose as the sole carbon source. Colonies were clonally purified, and integration of pPB0014 at the LCYE-1 locus was verified for 11 strains by PCR amplification of the regions flanking the 5' and 3' ends of the integration site. Strain 14-2 was selected as the parent strain for subsequent modifications. Next, we disrupted LCYE-2, encoding the second allele of lycopene cyclase epsilon, with the goal of generating double knockout strains completely lacking in alpha-carotene-derived carotenoids. The sequence of the transforming DNA from the LCYE-2 disruption construct pPB0038 is shown below in FIG. 3. Relevant restriction sites used to generate linear DNA and for cloning are indicated in lowercase, bold, and are from 5'-3' HindIII, KpnI, SacI, and HindIII. Underlined sequences at the 5' and 3' flanks of the construct represent genomic DNA from *A. protothecoides* that enable targeted integration of the transforming DNA via homologous recombination at the LCYE-2 locus. Proceeding in the 5' to 3' direction, the *A. protothecoides* HUP1 promoter (ApHUP1) driving the expression of the *Arabidopsis thaliana* THIC gene (AtTHIC, codon-optimized for expression in *A. protothecoides* and encoding 4-amino-5-hydroxymethyl-2-methylpyrimidine synthase activity, thereby permitting the strain to grow in the absence of exogenous thiamine) is indicated by lowercase, boxed text. The initiator ATG and terminator TGA for AtTHIC are indicated by uppercase italics, while the coding region is indicated with lowercase italics. The terminator region of the *A. protothecoides* heat shock protein 90 (ApHSP90) gene is indicated by small capitals.

Construct pPB0038 was transformed into LCYE-1 disruption strain 14-2. Primary transformants were selected for heterotrophic growth on media without thiamine, and with sucrose as the sole carbon source. Colonies were clonally purified, and double knockout of both LCYE-1 and LCYE-2 was verified in strain 38-25 by PCR amplification of the regions flanking the 5' and 3' ends of the pPB0014 and pPB0038 integrations. Spectrophotometric, and HPLC analysis of carotenoid pigments from wild-type *A. protothecoides* PB5, 14-2, and 38-25 is shown in FIGS. 4A and B. Pigments for spectrophotometric analysis were extracted by mechanical disruption of cell pellets mixed with 0.5 mm glass beads (BioSpec Products, Inc.) suspended in 80:20 acetone:methanol, using a Mini-Beadbeater-16 (BioSpec Products, Inc.). Absorption spectra were acquired using a Thermo Scientific GeneSys 10 uv spectrophotometer. Lutein is the predominant pigment extracted from the wild-type strain. Reduction of lycopene cyclase epsilon activity by disrupting the LCYE-1 allele in 14-2 increases the ratio of zeaxanthin to lutein. Lutein accumulation is abolished in the 38-25 double knockout strain, and zeaxanthin is the major carotenoid.

Cell cultivation—Cells were grown in a growth medium composed of the following chemicals in 1 L deionized water. 0.025 g NaCl, 0.25 g $NaNO_3$, 0.074 g $MgSO_4.7H_2O$, 0.025 g $CaCl_2\cdot 2H_2O$, 0.075 g $K_2HPO_4$, 0.176 g $KH_2PO_4$, 2.38 g HEPES, 3 g Yeast extract, 5 ml stock vitamin solutions, and 20 g glucose. pH was adjusted to 6.8 with 20% NaOH. Stock vitamin solution contained the following in 200 ml HEPES solution (50 mM HEPES, pH7.8); 0.005 g Biotin, 0.44 g Thiamine HCl, 0.027 g B12, and 0.619 g D-Pantothenic acid hemicalcium. The stock vitamin solution was filtered, sterilized, and stored at 4° C. refrigerator.

Seed flask cultivation—in 250 ml Erlenmeyer flask containing 95 ml growth medium and 5 ml 40% stock glucose solution, loopful of cells were inoculated from the agar plate and grown for 2 days on an orbital shaker at 115 rpm at 28° C. under 0.1-1 μmol photons/$m^2$ s low intensity LED light.

Main flask cultivation—in 1 L Erlenmeyer flask containing 332.5 ml growth medium and 17.5 ml 40% stock glucose solution, inoculate cells from seed flask so that initial optical density (OD) at 750 nm wavelength was 0.5-0.6. Incubate the flask on the orbital shaker under 0.1-1 μmol photons/$m^2$ s low intensity LED light at 115 rpm at 28° C. for 4-5 days until all glucose is exhausted. Harvest the cells via centrifugation and freeze dry the cell pellet. Store the freeze-dried cell pellet at −20° C. freezer.

The lipid extraction method and HPLC parameters are described below.

About 3-5 g lyophilized PB5 and modified strain cell powders were finely ground in a mortar using a pestle. 30 ml of ether was added to the milled microalga powders then vortexed for about 30 seconds to extract oil and carotenoids. 30 ml of additional ether was used if necessary to complete the extraction of all the oil and carotenoids. The remaining ether was evaporated using an evaporator at room temperature. The extracted oil was dissolved and diluted at a 1:10 ratio with a mixed Hexane:Ethyl Acetate (70:30, v/v) solvent. 10 ul of the diluted solution was injected into an HPLC (Agilent 1260 Infinity II, Agilent, USA) and separation of analytes was conducted on a Luna silica 100 A column (25 cm×4.6 mm; 5 μm, Phenomenex, USA). The mobile phase consisted of hexane:ethyl acetate (70:30, v/v) at a flow rate of 1.5 ml/min. The column temperature was set at 30° C. and lutein, zeaxanthin, and standards were detected at 446 nm. The lutein standard eluted at a retention time of 12.6 minutes and the zeaxanthin standard eluted at a retention time of 13.5 minutes. Table 1 summarized the results of carotenoid analysis of each genetically modified strain and wild-type strain PB5 (control).

TABLE 1

Carotenoids identified in extracted oil from PB5 and modified strains via HPLC.

| Strains | Carotenoids | Retention time | Percent (%) |
|---|---|---|---|
| PB5 (Control) | Lutein | 12.689 | 67.0392 |
| | Zeaxanthin | 13.548 | 27.9272 |
| 14-2 | Lutein | 12.685 | 50.1228 |
| | Zeaxanthin | 13.55 | 45.4815 |
| 38-25 | Zeaxanthin | 13.554 | 87.8917 |

Next, we sought to express beta-carotene ketolase activity in *A. protothecoides* cells, allowing them to make keto-carotenoids with high value as antioxidants. To achieve this, we introduced an expression module for the *C. reinhardtii* beta-carotene ketolase gene 1 (CrBKT1) into the pPB0038 backbone. The sequence of the expression module cloned into the KpnI site of pPB0038 to generate construct pPB0120 is shown below in FIG. 5. KpnI and SpeI sites flanking the expression module and used for cloning are indicated in lowercase, bold. Proceeding in the 5' to 3' direction, the *A. protothecoides* SAD2 promoter (ApSAD2) driving the expression of the CrBKT1 gene is indicated by lowercase, boxed text. The initiator ATG and terminator TGA for CrBKT1 are indicated by uppercase italics, while the coding region is indicated with lowercase italics. The sequence encoding the predicted plastid transit peptide is underlined. The terminator region of *A. protothecoides* SAD2 is indicated by small capitals.

We considered that the heterologous CrBKT1 protein might not be imported efficiently into *Auxenochlorella* plastids, so we also made a version of the CrBKT1 expression module that replaced the sequence encoding the native plastid transit peptide with the corresponding sequence from the endogenous *Auxenochlorella* SAD2 gene. The sequence of the chimeric ApSAD2tp_CrBKT1 coding sequence in construct pPB0123 is shown below in FIG. 6. pPB0123 was otherwise identical to pPB0120 and targeted the AtTHIC transformation marker and the CrBKT1 expression module to the LCYE-2 locus. The sequences of the native CrBKT1 protein and the ApSAD2tp_CrBKT1 chimeric proteins are shown in FIGS. 7A and 7B, respectively.

Constructs pPB0120 and pPB0123 were both transformed into wild-type *A. protothecoides* PB5 to make LCYE-2 single allele knockouts expressing CrBKT1, and into LCYE-1 disruption strain 14-2 to make LCYE double knockouts expressing CrBKT1. Primary transformants made in the wild-type *A. protothecoides* background were selected for heterotrophic growth on glucose-containing media without thiamine, while transformants generated in the 14-2 parent strain were selected on media without thiamine, supplemented with sucrose. Primary transformants were clonally purified and shake flask cultures of representative strains are shown in FIG. 8A. Strains transformed with pPB0123, expressing chimeric ApSAD2tp_CrBKT1 produced more red-colored ketocarotenoids than pPB0120 transformants that expressed native CrBKT1, suggesting that the chimeric protein was imported and processed more efficiently than the native protein. HPLC analysis, shown in FIG. 8B, showed that the predominant ketocarotenoids in LCYE-2 single allele knockouts (A strains, wild-type *A. protothecoides* parent) were 4-keto-lutein and astaxanthin, derived from lutein and zeaxanthin, respectively. The strains that expressed CrBKT1 with both LCYE alleles disrupted (B strains) made astaxanthin almost exclusively.

The lipid extraction method and HPLC parameters for keto-carotenoids analysis—Ether extraction of oil and carotenoids was performed as described above. The extracted oil was dissolved and diluted at a 1:100 ratio with a solvent mixture of Hexane:Acetone (82:18, v/v). 20 ul of the diluted solution was injected into an HPLC (Agilent 1260 Infinity II, Agilent, USA) and separation of analytes was conducted on a Luna silica column (15 cm×4.6 mm; 3 μm, Phenomenex, USA). The mobile phase consisted of Hexane:Acetone (82:18, v/v) ran at a flow rate of 1.2 ml/min. The column temperature was not set and astaxanthin and standards were detected at 474 nm. The astaxanthin standard was eluted at a retention time of 7.6 minutes. Table 2 summarized HPLC analysis results of genetically modified strains producing different carotenoids.

TABLE 2

Carotenoids identified in extracted oil from modified strains via HPLC.

| Strains | Carotenoids | Retention time | Percent (%) |
|---|---|---|---|
| 120A-2 | Astaxanthin | 7.638 | 29.8938 |
| | Keto Lutein | 9.258 | 39.4228 |
| | Lutein | 12.682 | 11.5903 |
| 123A-5 | Astaxanthin | 7.634 | 30.0058 |
| | Keto Lutein | 9.254 | 39.9874 |
| | Lutein | 12.685 | 7.5039 |
| 120B-2 | Astaxanthin | 7.631 | 71.5094 |
| | Zeaxanthin | 13.571 | 3.3719 |
| 123B-24 | Astaxanthin | 7.632 | 77.876 |
| | Zeaxanthin | 13.582 | 2.5516 |

Example 2. Production of Strains with Accumulating Squalene

Squalene is used extensively in cosmetics as an emollient and moisturizer, while its antioxidant properties are exploited in sunscreens and anti-aging products. There are numerous pharmacological applications, including use in formulations as a chemoprotective agent, an anti-bacterial and anti-fungal agent, an adjuvant for vaccines, and a drug carrier. In vivo studies have demonstrated its value as a food supplement with benefits for weight and cholesterol control. Squalene is also a valuable precursor for the chemical synthesis of steroids and other bioactive molecules.

We have enhanced the value of *A. protothecoides*, PB5, storage lipid by engineering strains to accumulate squalene during the lipid production phase by targeted disruption of the squalene epoxidase (SQE) gene. Squalene epoxidase catalyzes the squalene cyclization step in phytosterol biosynthesis. Knockout of the equivalent ERG1 gene in *S. cerevisiae* led to squalene accumulation. Similar metabolic engineering strategies have been applied in cyanobacteria and purple non-sulfur bacteria, and elevated squalene levels were observed in *C. reinhardtii* strains where RNAi was used to knock-down SQE gene expression.

In this example, we describe genetically engineered *A. protothecoides*, PB5 strains in which we have disrupted both alleles of SQE. These modifications block downstream phytosterol biosynthesis and cause the accumulation of squalene in cellular lipids. The sequence of the transforming construct pPB0065, targeting disruption of ApSQE-2 is provided in FIG. 9. Restriction sites are indicated with bold, lowercase text. HindIII sites delimit the 5' and 3' ends of the transforming DNA. EcoRI and SacI sites flank the selection cassette. Underlined sequences represent SQE-2 genomic DNA targeting integration at the SQE-2 locus via homologous recombination. Proceeding from 5' to 3', the selection cassette contains the ApHUP1 promoter (lowercase, boxed text), driving the expression of codon-optimized AtTHIC. The initiator ATG and terminator TGA for AtTHIC are indicated by uppercase italics, while the coding region is indicated with lowercase italics. The ApHSP90 terminator region is indicated by small capitals.

SQE-2 knockout strains were generated by transformation of pPB0065 into *A. protothecoides* PB5. Primary transformants were selected on glucose-containing growth media without thiamine. Colonies were clonally purified, and targeted disruption of SQE-2 was verified by PCR amplification and sequencing of the regions flanking the integration site. Transformant 65-4 was selected as the parent strain for subsequent transformation with construct pPB0077, targeting ApSQE-1. The sequence of the transforming DNA from pPB0077 is shown below in FIG. 10. Restriction sites are indicated with bold, lowercase text. HindIII sites delimit the 5' and 3' ends of the transforming DNA. EcoRI and SacI sites flank the selection cassette. Underlined sequences represent ApSQE-1 genomic DNA targeting integration at the ApSQE-1 allele via homologous recombination. Proceeding from 5' to 3', the selection cassette contains the CrTUB2 promoter (lowercase, boxed text), driving the expression of codon-optimized ScSUC2. The initiator ATG and terminator TGA for ScSUC2 are indicated by uppercase italics, while the coding region is indicated with lowercase italics. The ApPGH terminator region is indicated by small capitals.

Primary transformants from the introduction of pPB0077 into strain 65-4 were selected on growth media with sucrose and without thiamine. Colonies were clonally purified and targeted disruption of both ApSQE-1 and ApSQE-2 was verified by PCR amplification and sequencing of the regions flanking the integration site.

Figure 11A:
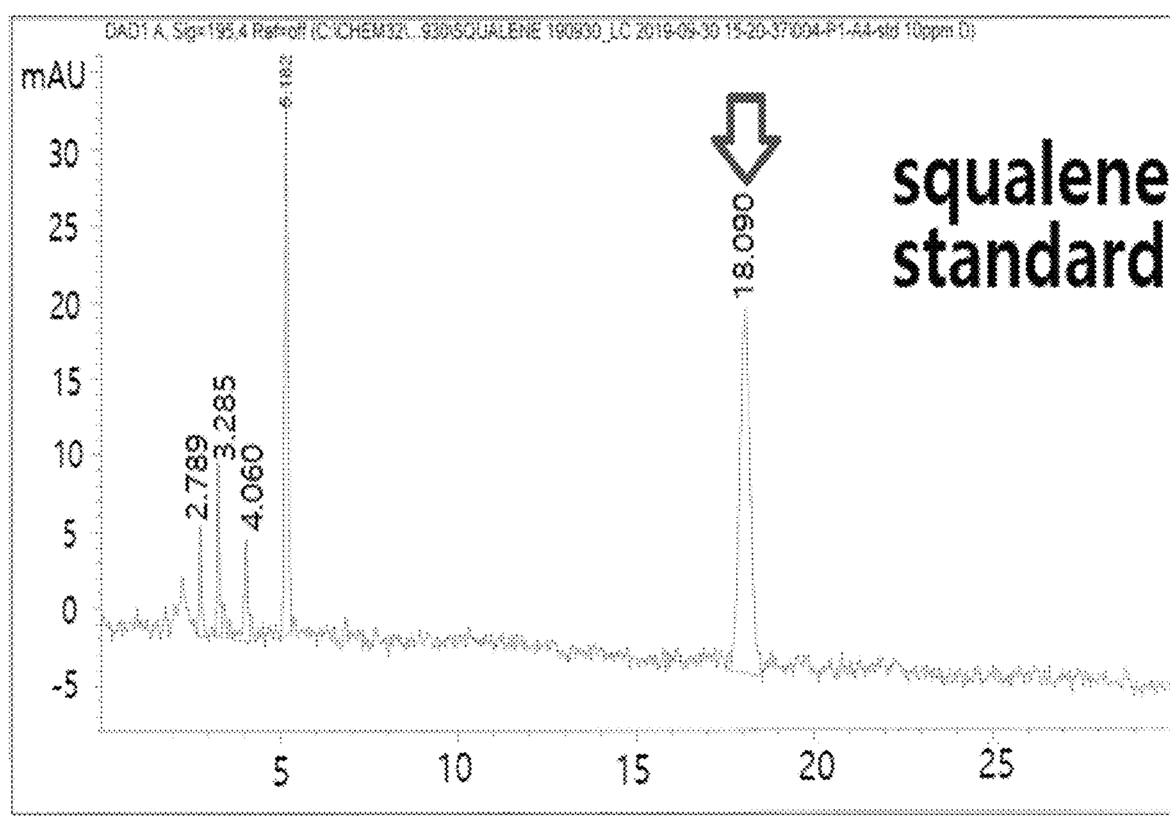
FIGS. 11A-B show the chromatograms of HPLC analysis of the standard squalene (FIG. 11A), the accumulation of squalene in SQE double knockout strain 77B-21 (FIG. 11B).
Figure 11B:
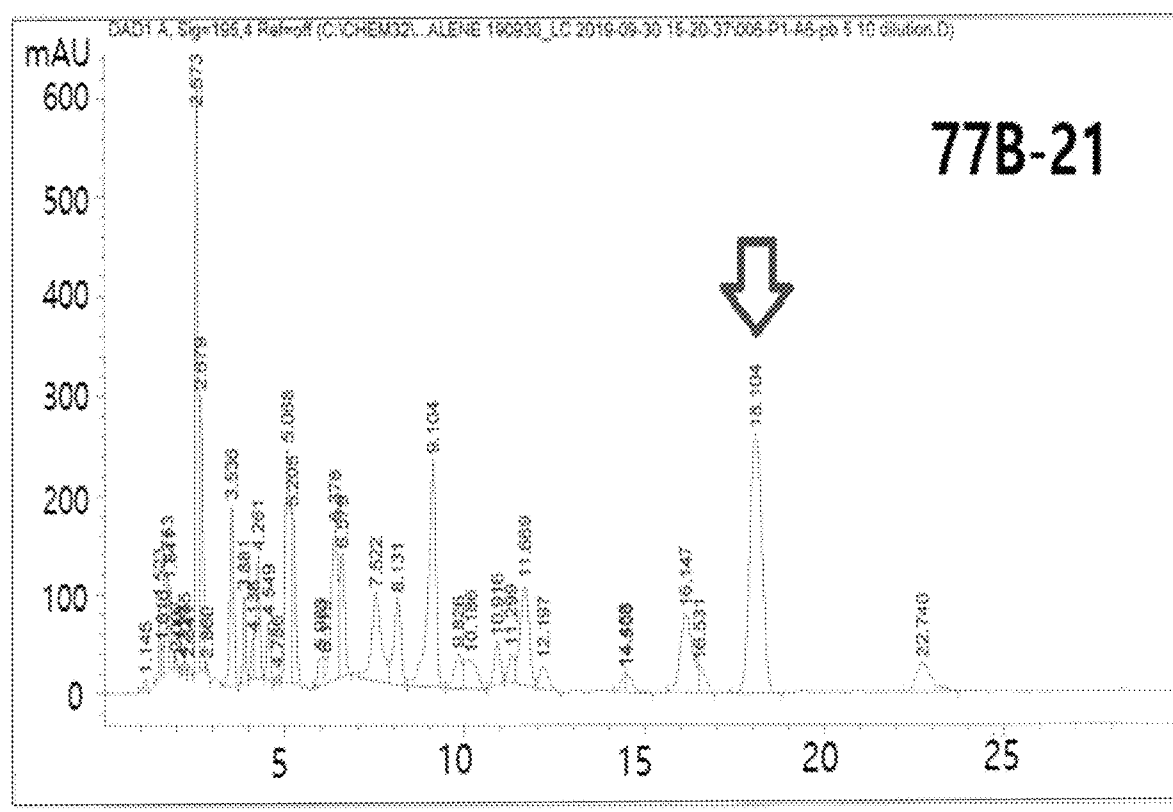

A representative strain, 77B-21, was grown in lipid production media and the squalene content of crude lipid extracts was measured by HPLC (FIG. 11).

Cell cultivation conditions—Cells were grown in a growth medium containing the followings in 1 L deionized water: 4.2 g $K_2HPO_4$, 3.57 g $NaH_2PO_4 \cdot H_2O$, 0.24 g $MgSO_4 \cdot 7H_2O$, 0.025 g $CaCl_2 \cdot 2H_2O$, 0.25 g citric acid, 2 micromolar thiamine-HCl, and 10 mL of trace metal solution. 1 L of trace metal solution contained 2.75 g citric acid, 0.011 g $CuSO_4 \cdot 5H_2O$, 0.081 g $CoCl_2 \cdot 6H_2O$, 0.33 g $H_3BO_3$, 1.4 g $ZnSO_4 \cdot 7H_2O$, 0.9485 g $MnCl_2 \cdot 4H_2O$, 0.039 g $Na_2MoO_4 \cdot 2H_2O$, 0.11 g $FeSO_4 \cdot 7H_2O$, 0.0144 g $NiSO_4 \cdot 6H_2O$. Pre-seed and seed medium contained 0.991 g/L of $(NH_4)_2SO_4$, and lipid production media contained 0.248 g of $(NH_4)_2SO_4$. The pre-seed medium was supplemented with 5 g/L glucose; seed medium contained 20 g/L glucose and lipid production contained 40 g/L glucose.

The lipid extraction method and HPLC parameters for squalene analysis—About 3 g of lyophilized PB5 and modified strain cell powders were finely ground in a mortar using a pestle. 30 ml of ether was added to the ground PB5 powder and the resulting suspension was vortexed for about 30 seconds to extract oil. An additional 30 ml of ether was used to complete oil extraction. The remaining ether was evaporated at room temperature using an evaporator. The extracted oil was dissolved and diluted at a 1:10 ratio with a solvent mixture solvent of Acetonitrile:Methanol (8:2, v/v), which was also used as the mobile phase. 30 ul of the diluted solution was injected into an HPLC (Agilent 1260 Infinity II) and separation of analytes was conducted on a C18 reverse column (15 cm×4.6 mm; Shiseido, Japan). The mobile phase's flow rate was 1.5 ml/min. The column temperature was set at 35° C. and squalene and the standard was detected at 195 nm. Squalene standard eluted at a retention time of 18.090.

Squalene accumulated to 1222 ppm in oil from strain 77B-21, a level that is on par with the squalene content of olive oil, a common commercial source.

The value of *A. protothecoides* oil would be enhanced by further increases in squalene levels. This may be achieved through overexpression of key enzymes in the isoprenoid biosynthesis pathway to increase flux. The amino acid sequences of *A. protothecoides* 1-deoxy-D-xylulose 5-phosphate synthase (DXS), 1-deoxy-D-xylulose 5-phosphate reductoisomerase (DXR), farnesyl diphosphate synthase (FDPS), and squalene synthase are provided in FIGS. 12-15. Overexpression of the native *A. protothecoides* enzymes, or of heterologous enzymes from plants or other algae, in the SQE double knockout background may improve squalene accumulation.

Example 3. Production of Strains with Increased Levels of Omega-3 and Omega-6 Fatty Acids The fatty acid composition of *A. protothecoides* storage lipid is typical for Trebouxiophyte algae, consisting mainly of oleic (~68%), palmitic (~12%), and linoleic (~13%) acids, with minor amounts of stearic, myristic, α-linolenic, and palmitoleic acids. We sought to improve the nutritional quality of *A. protothecoides* triacylglyceride oils by increasing the polyunsaturated fatty acid (PUFA) content. First, we activated the endogenous FAD3 gene, encoding fatty acid desaturase 3, by swapping the native FAD3 promoter with promoters from genes that are strongly upregulated during lipid production. FAD3 introduces a double bond at the Δ15 position of linoleic acid (C18:2) to make α-linolenic acid. The sequence of the transforming construct pPB0039, targeting insertion of the ApSAD2 promoter upstream of the FAD3-1 coding sequence is provided in FIG. 16. Restriction sites are indicated with bold, lowercase text. HindIII sites delimit the 5' and 3' ends of the transforming DNA. KpnI and SpeI sites flank the selection cassette. Underlined sequences represent FAD3-1 genomic DNA targeting integration at the FAD3-1 locus via homologous recombination. Proceeding from 5' to 3', the selection cassette contains the ApHUP1 promoter (lowercase, boxed text), driving the expression of codon-optimized AtTHIC. The initiator ATG and terminator TGA for AtTHIC are indicated by uppercase italics, while the coding region is indicated with lowercase italics. The ApHSP90 terminator region is indicated by small capitals. Lowercase, boxed text delineates the ApSAD2 promoter.

We also made a version of the FAD3 integration construct expression module that replaced the native FAD3 promoter with the promoter from the *A. protothecoides* FATA gene, encoding the acyl-ACP thioesterase. Construct pPB0041 was identical to pPB0039 except that ApFATA promoter shown below in FIG. 17 in lowercase, boxed text, was used to drive the expression of FAD3.

pPB0039 and pPB0041 were transformed into *A. protothecoides* PB5 and primary transformants were selected on glucose-containing growth media without thiamine. Colonies were clonally purified and insertion of the constructs at the FAD3 locus was verified by PCR amplification and sequencing of the regions flanking the integration site.

Cell cultivation conditions—Cells were grown in a growth medium composed of the following chemicals in 1 L of deionized water: 4.2 g $K_2HPO_4$, 3.57 g $NaH_2PO_4 \cdot H_2O$, 0.24 g $MgSO_4 \cdot 7H_2O$, 0.025 g $CaCl_2 \cdot 2H_2O$, 0.25 g citric acid, 2 micromolar thiamine-HCl, and 10 mL of trace metal solution. 1 L of trace metal solution contained 2.75 g citric acid, 0.011 g $CuSO_4 \cdot 5H_2O$, 0.081 g $CoCl_2 \cdot 6H_2O$, 0.33 g $H_3BO_3$, 1.4 g $ZnSO_4 \cdot 7H_2O$, 0.9485 g $MnCl_2 \cdot 4H_2O$, 0.039 g $Na_2MoO_4 \cdot 2H_2O$, 0.11 g $FeSO_4 \cdot 7H_2O$, 0.0144 g $NiSO_4 \cdot 6H_2O$. Pre-seed and seed medium contained 0.991 g/L of $(NH_4)_2SO_4$, and lipid production media contained 0.248 g of $(NH_4)_2SO_4$. The pre-seed medium was supplemented with 5 g/L glucose; seed medium contained 20 g/L glucose and lipid production contained 40 g/L glucose.

Freeze-dried microalgal samples were sent to Microbial ID Inc., (Delaware, USA) for fatty acid methyl ester analysis (FAME). Microbial ID Inc. utilized standardized gas chromatographic analysis of fatty acid methyl esters method developed by MIDI Inc., (Delaware, USA) and the reference could be found in their technical note #101, published and revised in 2006. The fatty acid profiles of lipids from shake flask assays of representative strains are shown in Table 3. Strains driving expression of one allele of FAD3 with the ApSAD2 promoter (39-1 and 39-9 strains) or the ApFATA promoter (41-1 and 41-3 strains) showed a slight increase in α-linolenic acid (ALA, omega-3) from 2% in the wild-type (PB5) to about 3%. The increase in ALA came at the expense of linoleic acid (omega-6), improving the omega-6:omega-3 ratio from 7 to about 4 (lower is better).

TABLE 3

Fatty acid profiles as a percentage of total fatty acids for *A. protothecoides* strains transformed with pPB0039 or pPB0041.

| strain | PB5 | 39-1 | 39-9 | 41-1 | 41-3 |
|---|---|---|---|---|---|
| C14:0 myristic | 1.7 | 1.6 | 1.7 | 1.6 | 1.7 |
| C16:0 palmitic | 12.7 | 13.0 | 12.6 | 12.0 | 12.6 |
| C16:1n-7 palmitoleic | 0.3 | 0.3 | 0.3 | 0.3 | 0.3 |
| C18:0 stearic | 2.5 | 2.5 | 2.6 | 2.4 | 2.3 |
| C18:1n-9 oleic | 66.3 | 68.9 | 67.8 | 68.5 | 67.5 |
| C18:2n-6 linoleic LA | 14.2 | 10.5 | 11.1 | 11.7 | 11.9 |
| C18:3n-3 α-linolenic | 2.0 | 2.9 | 3.3 | 3.0 | 3.1 |
| omega-6:omega-3 | 6.9 | 3.6 | 3.4 | 4.0 | 3.9 |
| % PUFA | 16.2 | 13.4 | 14.4 | 14.6 | 15.0 |

The Δ9 double bond in C18:1 is introduced by the stearoyl-ACP desaturases (SADs) in the plastid. Formation of the Δ12 and Δ15 double bonds, catalyzed by FAD2 and FAD3, respectively, occurs in the endoplasmic reticulum, and these enzymes use membrane lipids as their substrate. The relatively low abundance of C18:2 and C18:3 α in wild-type *A. protothecoides* storage lipid results from the competition between the acyltransferases of the Kennedy pathway for the formation of TAG, and the enzymes of the Lands cycle, which control the exchange of fatty acids between diacylglycerol (DAG) and membrane phospholipids. We considered that increasing the transfer of C18:1 between DAG and phospholipids might improve PUFA production, so we introduced a construct to overexpress *Arabidopsis* PDCT, encoding phosphatidylchloline:diacylglycerol choline phosphotransferase into strain 41-3. The sequence of the transforming construct pPB0118, targeting AtPDCT and ScSUC2 expression to the THI4 locus is provided in FIG. 18. Restriction sites are indicated with bold, lowercase text. HindIII sites delimit the 5' and 3' ends of the transforming DNA. KpnI, SpeI, and XhoI sites separate the AtPDCT expression module and the ScSUC2 expression cassette. Underlined sequences represent THI4 genomic DNA targeting integration at the THI4 locus via homologous recombination. Proceeding from 5' to 3', the selection cassette contains the ApSAD2 promoter (lowercase, boxed text), driving the expression of codon-optimized AtPDCT. The initiator ATG and terminator TGA for AtPDCT are indicated by uppercase italics, while the coding region is indicated with lowercase italics. The ApSAD2 terminator region is indicated by small capitals. Lowercase, boxed text delineates the CrTUB2 promoter, driving the expression of codon-optimized ScSUC2. The initiator ATG and terminator TGA for ScSUC2 are indicated by uppercase italics, while the coding region is indicated with lowercase italics. The ApPGH terminator region is indicated by small capitals.

pPB0118 was transformed into strain 41-3, and primary transformants were selected on sucrose-containing growth media without thiamine. Colonies were clonally purified and insertion of the constructs at the THI4 locus was verified by PCR amplification and sequencing of the regions flanking the integration site. Freeze-dried microalgal cell samples were sent to Microbial ID inc. (Delaware, USA) for fatty acid methyl ester analysis and the profiles of lipids from shake flask assays of representative strains containing the pPB0118 construct are shown in Table 4. C18:2 accumulation increased by 2.5-fold in strains 118B-8 and 118B-20, indicating that expression of AtPDCT during lipid production caused significant enhancement of FAD2 activity. ALA levels only increased by about 1% compared to the 41-3 parent strain, suggesting that incorporation of C18:2 into TAG was favored over desaturation by FAD3. The omega-6:omega-3 ratio increased from 3.8 in 41-3 to above 8, due to the increase in C18:2 without a concomitant increase in ALA.

TABLE 4

Fatty acid profiles as a percentage of total fatty acids for strain 41-3 transformed with pPB0118.

| strain | PB5 | 41-3 | 118B-8 | 118B-20 |
|---|---|---|---|---|
| C14:0 myristic | 1.7 | 1.8 | 2.1 | 2.1 |
| C16:0 palmitic | 12.3 | 12.5 | 12.4 | 13.3 |
| C16:1n-7 palmitoleic | 0.3 | 0.3 | 0.3 | 0.4 |
| C18:0 stearic | 2.4 | 2.3 | 1.8 | 2.2 |
| C18:1n-9 oleic | 67.9 | 67.5 | 45.4 | 46.4 |
| C18:2n-6 linoleic LA | 13.1 | 12.0 | 33.3 | 30.8 |
| C18:3n-3 α-linolenic | 1.8 | 3.1 | 4.0 | 3.9 |
| omega-6:omega-3 | 7.2 | 3.8 | 8.3 | 8.0 |
| % PUFA | 15.0 | 15.1 | 37.3 | 34.7 |

Upregulation of the endogenous FAD3 gene and overexpression of AtPDCT only resulted in small improvements in ALA accumulation, so we tested whether ALA biosynthesis could be further improved by the expression of heterologous FAD3. We chose to test FAD3A from *Linum usitatissimum* (flax), which has been shown previously to have desaturase activity in *Prototheca moriformis*. The sequence of the transforming construct pPB0142, targeting LuFAD3A and neoR expression to the THI4 locus is provided in FIG. 19. Restriction sites are indicated with bold, lowercase text. HindIII sites delimit the 5' and 3' ends of the transforming DNA. KpnI, SpeI, and BamHI sites separate the LuFAD3A expression module and the neoR expression cassette. Underlined sequences represent THI4 genomic DNA targeting integration at the THI4 locus via homologous recombination. Proceeding from 5' to 3', the selection cassette contains the ApSAD2 promoter (lowercase, boxed text), driving the expression of codon-optimized LuFAD3A. The initiator ATG and terminator TGA for LuFAD3A are indicated by uppercase italics, while the coding region is indicated with lowercase italics. The ApFBA1 terminator region is indicated by small capitals. Lowercase, boxed text delineates the ApPGK1 promoter, driving the expression of codon-optimized neoR, which confers resistance to the antibiotic G418. The initiator ATG and terminator TGA for neoR are indicated by uppercase italics, while the coding region is indicated with lowercase italics. The ApPGK1 terminator region is indicated by small capitals.

pPB0142 was transformed into strain 118B-8, and primary transformants were selected on G418-containing growth media supplemented with sucrose and without thiamine. Colonies were clonally purified and insertion of the constructs at the THI4 locus was verified by PCR amplification and sequencing of the regions flanking the integration site. We also verified that strains containing both constructs pPB0118 and pPB0142 disrupted both alleles of the THI4 locus, rendering them unable to grow without supplementation with hydroxymethyl thiazole (FIG. 20).

As shown in FIG. 20, Thiamine prototrophy is observed in strain 118B-8, expressing AtTHIC, targeted to one allele of THI4. Disruption of the second THI4 allele by pPB0142 renders the transformants thiazole auxotrophs.

Freeze-dried microalgal cell pellets were sent to Microbial ID (Delaware, USA) for fatty acid methyl ester analysis (FAME) and the profiles of lipids from shake flask assays of representative strains containing the pPB0142 construct are shown in Table 5. ALA accumulation increased from 5.4% in the 118B-8 parent to up to 8.7% in strain 142B-11, indicating that expression of LuFAD3A during lipid production enhanced desaturation of C18:2. The omega-6:omega-3 ratio was reduced to 4, similar to the original ratio observed in the parent strain 41-3 (see Table 4), but with a 5-fold increase in omega-3 fatty acids and a 3-fold improvement in overall PUFA compared to the wild-type strain.

TABLE 5

Fatty acid profiles as a percentage of total fatty acids for strain 118B-8 transformed with pPB0142.

| strain | PB5 | 118B-8 | 142B-8 | 142B-11 |
|---|---|---|---|---|
| C14:0 myristic | 2.0 | 2.5 | 2.3 | 2.2 |
| C16:0 palmitic | 12.0 | 11.8 | 12.5 | 12.0 |
| C16:1n-7 palmitoleic | 0.4 | 0.3 | 0.4 | 0.4 |
| C18:0 stearic | 2.5 | 1.8 | 1.9 | 1.8 |
| C18:1n-9 oleic | 67.9 | 44.1 | 39.9 | 39.2 |
| C18:2n-6 linoleic LA | 13.5 | 34.0 | 34.4 | 34.6 |
| C18:3n-3 α-linolenic | 1.8 | 5.4 | 8.2 | 8.7 |
| omega-6:omega-3 | 7.6 | 6.3 | 4.2 | 4.0 |
| % PUFA | 15.3 | 39.4 | 42.6 | 43.3 |

We aim to produce a nutritionally superior oil from *A. protothecoides* PB5, with very low saturates and a 1:1 ratio of omega-6:omega-3 fatty acids. Optimization of C18:2 and C18:3 α levels may be achieved by modulating the expression of AtPDCT and LuFAD3A. The main saturated fatty acids in wild-type *A. protothecoides* oil are C14:0, C16:0, and C18:0 (see Tables 3, 4 & 5). Levels of C14:0 and C16:0 can be reduced by over-expressing the native KASII gene, encoding beta-ketoacyl-ACP synthase II, which extends C16:0 to C18:0. The coding sequence of the *Auxenochlorella* KASII gene, optimized for translation, is shown in FIG. 21 and the corresponding amino acid sequence is detailed in FIG. 22.

REFERENCES

1. Single cell oils. (AOCS Press, 2010).
2. Zaimes, G. G. & Khanna, V. Environmental sustainability of emerging algal biofuels: A comparative life cycle evaluation of algal biodiesel and renewable diesel. Environ. Prog. Sustain. Energy 32, 926-936 (2013).
3. Bhujade, R., Chidambaram, M., Kumar, A. & Sapre, A. Algae to Economically Viable Low-Carbon-Footprint Oil. Annu. Rev. Chem. Biomol. Eng. 8, 335-357 (2017).
4. Huang, Y. S. & Sinclair, A. Lipids in Infant Nutrition. (AOCS Publishing, 1998). doi:10.1201/9781439831953.
5. Naguib, Y. M. A. Antioxidant Activities of Astaxanthin and Related Carotenoids. J. Agric. Food Chem. 48, 1150-1154 (2000).
6. Schmidt, I. et al. Biotechnological production of astaxanthin with *Phaffia rhodozyma/Xanthophyllomyces dendrorhous*. Appl. Microbiol. Biotechnol. 89, 555-571 (2011).
7. Elwan, H. a. M., Elnesr, S. S., Abdallah, Y., Hamdy, A. & El-Bogdady, A. H. Red yeast (*Phaffia rhodozyma*) as a source of Astaxanthin and its impacts on productive performance and physiological responses of poultry. Worlds Poult. Sci. J. 75, 273-284 (2019)
8. Nicolaides, N. (1974). Skin lipids: their biochemical uniqueness. Science 186, 19-26
9. Amarowicz, R. (2009). Squalene: a natural antioxidant? Eur. J. Lipid Sci. Technol. 111, 411-412
10. Günes, F. E. (2013). Medical use of squalene as a natural antioxidant. Clin. Exp. Health Sci. 3, 220-228
11. Kim, S. K., and Karadeniz, F. (2012). "Biological importance and applications of squalene and squalane," in Advances in Food and Nutrition Research, Vol. 65. ed S. K. Kim (Walthum, MA: Academic Press), 223-233
12. Huang, Z. R., Lin, Y. K., and Fang, J. Y. (2009). Biological and pharmacological activities of squalene and related compounds: potential uses in cosmetic dermatology. Molecules 14, 540-554
13. Popa, O., Băbeanu, N. E., Popa, I., Niță, S., and Dinu-Pârvu, C. E. (2015). Methods for obtaining and determination of squalene from natural sources. Biomed. Res. Int. 2015:367/202
14. Aioi, A., Shimizu, T., and Kuriyama, K. (1995). Effect of squalene on superoxide anion generation induced by a skin irritant, lauroylsarcosine. Int. J. Pharm. 113, 159-164
15. Budiyanto, A., Ahmed, N. U., Wu, A., Bito, T., Nikaido, O., Osawa, T., et al. (2000). Protective effect of topically applied olive oil against photocarcinogenesis following UVB exposure of mice. Carcinogenesis 21, 2085-2090
16. Smith, T. J. (2000). Squalene: potential chemopreventive agent. Expert Opin. Invest. Drugs 9, 1841-1848
17. Kopicová, Z., and Vavreinová, S. (2007). Occurrence of squalene and cholesterol in various species of Czech freshwater fish. Czech. J. Food Sci. 25, 195-201
18. Del Giudice, G., Fragapane, E., Bugarini, R., Hora, M., Henriksson, T., Palla, E., et al. (2006). Vaccines with the MF59 adjuvant do not stimulate antibody responses against squalene. Clin. Vaccine Immunol. 13, 1010-1013
19. Pasquale, A. D., Preiss, S., Silva, F. T. D., and Gargon, N. (2015). Vaccine adjuvants: from 1920 to 2015 and beyond. Vaccines 3, 320-343
20. Ivanova, S., Tonchev, V., Yokoi, N., Yappert, M. C., Borchman, D., and Georgiev, G. A. (2015). Surface properties of squalene/meibum films and NMR confirmation of squalene in tears. Int. J. Mol. Sci. 16, 21813-21831
21. Rosales-Garcia, T., Jimenez-Martinez, C., and Dávila-Ortiz, G. (2017). Squalene extraction: Biological sources and extraction methods. Int. J. Environ. Agric. Biotechnol. 2, 1662-1670
22. Global Market Insights (2016). Squalene Market Size by Source, by Application, Industry Analysis Report, Regional Outlook, Application Potential, Price Trends, Competitive Market Share & Forecast, 2015-2022
23. Czaplicki, S., Ogrodowska, D., Zadernowski, R., and Derewiaka, D. (2012). Characteristics of biologically-active substances of amaranth oil obtained by various techniques. Pol. J. Food Nutr. Sci. 62, 235-239
24. Xiao Y, Lu Y, Dai J and Wu Q (2015) Industrial fermentation of Auxenochlorella protothecoides for production of biodiesel and its application in vehicle diesel engines. Front. Bioeng. Biotechnol. 3:164.

What is claimed is:

1. A method for producing oils with modified profiles of omega-3 fatty acids, omega-6 fatty acids, lutein, zeaxanthin, astaxanthin, 4-keto-lutein, or squalene, comprising: growing a microalgal mutant, wherein the microalgal mutant is made by knock-out, knock-in or homologous recombination, wherein the microalgal mutant is a mutant of Auxenochlorella protothecoides, wherein the microalgal mutant comprises a knock-out of at least one allele of lycopene cyclase epsilon LCYE-1, lycopene cyclase epsilon LYCE-2, squalene epoxidase SQE-1, or squalene epoxidase SQE-2, or a replacement of a native FAD3 promoter by a FATA gene promoter from Auxenochorella protothecoides or a stearoyl-ACP desaturase (SAD2) promoter from Auxenochorella protothecoides, and isolating the oil from the microalgal mutant.

2. The method of claim 1, wherein the zeaxanthin has a percent (w/w) of zeaxanthin is 2-3-fold higher compared to the wild-type microalgae and the zeaxanthin is present as a major carotenoid.

3. The method of claim 2, wherein the percent (w/w) of zeaxanthin produced ranges between 40 to 90% of a total identified carotenoids.

4. The method of claim 1, wherein the oil contains a mixture of 4-keto lutein and astaxanthin, and wherein the astaxanthin is present as a major carotenoid.

5. The method of claim 4, wherein the percent (w/w) of keto carotenoids produced ranges between 20-90% of a total identified carotenoids.

6. The method of claim 1, wherein the oil contains squalene.

7. The method of claim 1, wherein the omega-6 fatty acids and the omega-3 fatty acids have a weight ratio of omega-6 fatty acids to omega-3 fatty acids in the oil that is low compared to the oil produced from wild type microalgae.

8. The method of claim 7, wherein the weight ratio of omega-6 to omega-3 in the oil ranges from 1:1 to 5:1 compared to the oil produced from wild type microalgae which is 7:1.

9. The method of claim 1, wherein the omega-3 fatty acids increased 3-5-fold and the overall PUFA polyunsaturated fatty acids increased 2-3-fold compared to the wild-type strain.

10. The method of claim 1, wherein the microalgal mutant is characterized in that one or more of the alleles of the lycopene cyclase epsilon LCYE-1 gene, lycopene cyclase epsilon LYCE-2 gene are knocked out.

11. The method of claim 1, wherein the microalgal mutant is characterized in that one or more of the alleles of the squalene epoxidase SQE-1 gene, or squalene epoxidase SQE-2 gene are knocked out.

12. The method of claim 1, wherein the microalgal mutant is characterized in that the native FAD3 promoter is replaced with a stearoyl-ACP desaturase (SAD2) promoter or a promoter from the Auxenochorella protothecoides FATA gene encoding acyl-ACP thioesterase.

* * * * *

SEQUENCE LISTING

```
<160> NUMBER OF SEQ ID NOS: 18

<210> SEQ ID NO 1
<211> LENGTH: 3739
<212> TYPE: DNA
<213> ORGANISM: Artificial Sequence
<220> FEATURE:
<223> OTHER INFORMATION: Nucleotide sequence of the transforming DNA
      from pPB0014

<400> SEQUENCE: 1

aagcttcaag tgcgtgcgtt acagtgttac caacaacagt ctaacctacc cctttcggtc      60

attctgccct ttggcaagag ttcagaatga agtgtgcttg cacatcgagc tagtgctgtg     120

agcgaagaca aggaagtccc cactcaccca cgtggccaga ttctatcttt tttcagattg     180
```

```
caagggccac gcccagcgaa ccccgcgatg gggccgagcc atgcccgaca tctcgacatc    240
ttcatatgat aaggcgcttc aaagtgcaat ttttgtgcat ggcatcaatt aggagagtgc    300
ttgaacacca gcccatcttc caccggggaa ggaccgtcga aatgcctctg cagacggcca    360
ccgtctgatc gctgcctgtc ccgaggtgac ggcgatgtcg tccttatccc aaacaatcgt    420
tcgaagacct ttcttttgtt cgctcaaccc accgaggaga ccgtctggat tccatgctgc    480
tgtgacgcct agcccccctga gaccctccaa gtgggcggtc ccctccctag cccccagcct    540
ctctgacgtg gcagatgcct ccgcggaagc aaatcaggat cgcagggagg gctcctacga    600
gcagcccctg gtccaacgcc aggtgcctag ggggaaagga gggcagaggg gcttgaggcg    660
agcctggccc aggcagggct tccatggtca gtcgtggcag tgccatgaca gccgaagccc    720
aacgcgacac cgtgggtgca gcatgcgtgg acggaaacat tggcaatgcc ttgccccatt    780
ggccccccag gcccggaaac gggacgatca gcaggacccc ttgtccagcc tcctccccac    840
ggtacccttt cttgcgctat gacacttcca gcaaaaggta gggcgggctg cgagacggct    900
tcccggcgct gcatgcaaca ccgatgatgc ttcgaccccc cgaagctcct tcggggctgc    960
atgggcgctc cgatgccgct ccagggcgag cgctgtttaa atagccaggc ccccgattgc   1020
aaagacatta tagcgagcta ccaaagccat attcaaacac ctagatcact accacttcta   1080
cacaggccac tcgagcttgt gatcgcactc cgctaagggg gcgcctcttc ctcttcgttt   1140
cagtcacaac ccgcaaacat gctgctgcag gccttcctgt tcctgctggc cggcttcgcc   1200
gccaagatca gcgcctccat gacgaacgag acgtccgacc gccccctggt gcacttcacc   1260
cccaacaagg gctggatgaa cgaccccaac ggcctgtggt acgacgagaa ggacgccaag   1320
tggcacctgt acttccagta caacccgaac gacaccgtct gggggacgcc cttgttctgg   1380
ggccacgcca cgtccgacga cctgaccaac tgggaggacc agcccatcgc catcgccccg   1440
aagcgcaacg actccggcgc cttctccggc tccatggtgg tggactacaa caacacctcc   1500
ggcttcttca acgacaccat cgacccgcgc cagcgctgcg tggccatctg gacctacaac   1560
accccggagt ccgaggagca gtacatctcc tacagcctgg acggcggcta caccttcacc   1620
gagtaccaga agaaccccgt gctggccgcc aactccaccc agttccgcga cccgaaggtc   1680
ttctggtacg agccctccca gaagtggatc atgaccgcgg ccaagtccca ggactacaag   1740
atcgagatct actcctccga cgacctgaag tcctggaagc tggagtccgc gttcgccaac   1800
gagggcttcc tcggctacca gtacgagtgc cccggcctga tcgaggtccc caccgagcag   1860
gaccccagca agtcctactg ggtgatgttc atctccatca accccggcgc cccggccggc   1920
ggctccttca accagtactt cgtcggcagc ttcaacggca cccacttcga ggccttcgac   1980
aaccagtccc gcgtggtgga cttcggcaag gactactacg ccctgcagac cttcttcaac   2040
accgacccga cctacgggag cgccctgggc atcgcgtggg cctccaactg ggagtactcc   2100
gccttcgtgc ccaccaaccc ctggcgctcc tccatgtccc tcgtgcgcaa gttctccctc   2160
aacaccgagt accaggccaa cccggagacg gagctgatca acctgaaggc cgagccgatc   2220
ctgaacatca gcaacgccgg cccctggagc cggttcgcca ccaacaccac gttgacgaag   2280
gccaacagct acaacgtcga cctgtccaac agcaccggca ccctggagtt cgagctggtg   2340
tacgccgtca acaccaccca gacgatctcc aagtccgtgt tcgcggacct ctccctctgg   2400
ttcaagggcc tggaggaccc cgaggagtac ctccgcatgg gcttcgaggt gtccgcgtcc   2460
tccttcttcc tggaccgcgg gaacagcaag gtgaagttcg tgaaggagaa cccctacttc   2520
```

-continued

```
accaaccgca tgagcgtgaa caaccagccc ttcaagagcg agaacgacct gtcctactac   2580
aaggtgtacg gcttgctgga ccagaacatc ctggagctgt acttcaacga cggcgacgtc   2640
gtgtccacca acacctactt catgaccacc gggaacgccc tgggctccgt gaacatgacg   2700
acgggggtgg acaacctgtt ctacatcgac aagttccagg tgcgcgaggt caagtgattg   2760
attggaactc acaaagcggc ccacggcttc gaacgtcccg tgtcaattgc gcggggtgtg   2820
ccagagtttc tgcgccaccg atgctcaccc taggggggga tgccctttga cattcatgtg   2880
tgcctgcatg cacgtttgta tcagtctcac cacaccttga agatttttgg gagggggggg   2940
gaagtcggaa tggaaacgag ctccgcgatt gtcagatggt ggagtgggtg gatggccctg   3000
ctccgaggag ctttctaggg cgcgaacttg gcccttctcc cctctgatgc agtgtggggg   3060
gacgcggtgt gctatttctc cgagggccgc ccaactaggg tggggcgggc atacgcccgc   3120
gtcgacaggt gggtgtggcc tcgaggtgtt gagaggagtg ttatgtcgac agccaaagtg   3180
gagactgatt gaaccctact ccaggtgcta tcttgggagc acactgcgcc caccgtggct   3240
ggactgcccg aattccaacc ttggtgccca gaaacagggc aaagccggtc atcagtgcag   3300
catgagactc aagctcccta gctcatgacc gttggcatag gcagaagctg cggcagcacc   3360
tggtggaggc ctgccaggca aacggtgtca ccttccagcc gggggaggta gtggatgtgg   3420
gcgtgaagaa cggcacagcc tcggtcacct gccaagatgg ctccgtcctg actgcgaggt   3480
gggcgctgtg catggcattt gttggcacga gtctgcatct ctgaagctgc tgggtagcgt   3540
cagagcagtg gagtcaacag cacacagctc tggcggtgct cagggaacat acatcgcact   3600
gtttcctgga gttgctggcc ctctgtgggg caaccaggac cccccgacgc atgcatgccc   3660
cctcgcacat cccgcacagg ctggtgaccc tggcctccgg cgcggcggcg gggcgcttcc   3720
tcaagtacga gagaagctt                                                3739
```

<210> SEQ ID NO 2
<211> LENGTH: 4611
<212> TYPE: DNA
<213> ORGANISM: Artificial Sequence
<220> FEATURE:
<223> OTHER INFORMATION: Nucleotide sequence of the transforming DNA from pPB0038

<400> SEQUENCE: 2

```
aagcttcaag tgcgtgcgtt acagtgttac caacaacagt ccaacctaac cctttcggtc     60
attctgtcct ttggcaaggg ctcagaatga agtgtgcctg cacatcgagc tagtgctgtg    120
agcgaagaca aggaagtccc cactcaccca cgtggccaga ttttatcttt tttcagattg    180
caagggccac gcccagcgaa ccccgcgatg gggccgagcc atgcccgaca tctcgacatc    240
ttcatatgac aaggcgcttc aaagtgcaat ttatgtgcat ggcatcgatt aggagagtgg    300
ttgaacacca gcccatcttc caccggggaa ggaccgtcga aatgcctctg cagacggcca    360
ccgtctgatc gctgcctgtc ccgaggtgac ggcgatgtcg tccttatccc aaacaatcgt    420
tcgaagacct ttcttttgtt cgctcaaccc accgaggaga ccgtctggat tccatgccgc    480
tgtgacgcct agccccctga gaccctccaa gtgggcggtc cctccctag ccccccagcct    540
ctctgacgtg gcagatgcct ccgcggaagc aaatcaggat cgcagggagg gctcctacga    600
gcagcccctg gtccaacgcc aggtgcctag ggggaaagga gggcaggggg ccttgaggcg    660
agcctggccc aggcagggct tccatggtca gtcgtggcag tgccatgaca gccgaagccc    720
accgcgacac cgtgggtgca gcatgcgtgg acggaaacat tggcaatgcc ttgccccatt    780
```

-continued

```
ggacccccag gcccggaaac gggacgatca gcaggacccc ctgtccagcc tcctccccac    840
ggtacctccc gctttttaat tgagcccctt tcgtcgctga atcagcgaaa gcaccgcgaa    900
acaatgcctg tcccgtccat gcatctcaac agcctcatgc aaggtttgca caagcaagac    960
cattctgatc tgggaacttg taggtgttgt atgggggagg ttgtgctctt gaatcaagtg   1020
gtatcacgtt tccggaacac cccgaaacgt gcatgggctt attgcgatga gagcatttcc   1080
caccgcgatt gtctcacgcg catttcggag aaggtttgca gaacactcca ggacatgaaa   1140
tgccttgtca cgtatgaacc atctcccacg gccttgaaaa gatcgctcga cttccattct   1200
agatggtgca aaccctacg actcaagaag gtgccaccga ctcaggcatt gggcacggcg   1260
ggcagggaga agagaggagt tgatcaaaac tgctcgatca cgttccccca tggcgatccg   1320
agcagcacat gatgcatcga ggtggcgccg ttgcaaagga gttgcgcatg ggtcgaagca   1380
gggagaagga aacggcgagg cgtgccgcgg gggtgaattc agagtcaaat ctgcgcctgc   1440
cccggcgctc ctgacgggga ttaaccccca cgactgtatc catcgacact cgtctcgggg   1500
gaataaaagc ggcgacccag ctccagaggc gcaatccttc tcacaatctg tttaactttc   1560
aacaaagtat aagtcaattc aacttgacac aatggccgcg tccgtccact gcaccctgat   1620
gtccgtggtc tgcaacaaca agaaccactc cgcccgcccc aagctgccca actcctccct   1680
gctgcccggc ttcgacgtgg tggtccaggc cgcggccacc cgcttcaaga aggagacgac   1740
gaccacccgc gccacgctga cgttcgaccc ccccacgacc aactccgagc gcgccaagca   1800
gcgcaagcac accatcgacc cctcctcccc cgacttccag cccatcccct ccttcgagga   1860
gtgcttcccc aagtccacga aggagcacaa ggaggtggtg cacgaggagt ccggccacgt   1920
cctgaaggtg cccttccgcc gcgtgcacct gtccggcggc gagcccgcct tcgacaacta   1980
cgacacgtcc ggcccccaga acgtcaacgc ccacatcggc ctggcgaagc tgcgcaagga   2040
gtggatcgac cgccgcgaga agctgggcac gccccgctac acgcagatgt actacgcgaa   2100
gcagggcatc atcacggagg agatgctgta ctgcgcgacg cgcgagaagc tggaccccga   2160
gttcgtccgc tccgaggtcg cgcggggccg cgccatcatc ccctccaaca agaagcacct   2220
ggagctggag cccatgatcg tgggccgcaa gttcctggtg aaggtgaacg cgaacatcgg   2280
caactccgcc gtggcctcct ccatcgagga ggaggtctac aaggtgcagt gggccaccat   2340
gtggggcgcc gacaccatca tggacctgtc cacgggccgc cacatccacg agacgcgcga   2400
gtggatcctg cgcaactccg cggtccccgt gggcaccgtc cccatctacc aggcgctgga   2460
gaaggtggac ggcatcgcgg agaacctgaa ctgggaggtg ttccgcgaga cgctgatcga   2520
gcaggccgag cagggcgtgg actacttcac gatccacgcg ggcgtgctgc tgcgctacat   2580
ccccctgacc gccaagcgcc tgacgggcat cgtgtcccgc ggcggctcca tccacgcgaa   2640
gtggtgcctg gcctaccaca aggagaactt cgcctacgag cactgggacg acatcctgga   2700
catctgcaac cagtacgacg tcgccctgtc catcggcgac ggcctgcgcc ccggctccat   2760
ctacgacgcc aacgacacgg cccagttcgc cgagctgctg acccagggcg agctgacgcg   2820
ccgcgcgtgg gagaaggacg tgcaggtgat gaacgagggc cccggccacg tgcccatgca   2880
caagatcccc gagaacatgc agaagcagct ggagtggtgc aacgaggcgc ccttctacac   2940
cctgggcccc ctgacgaccg acatcgcgcc cggctacgac cacatcacct ccgccatcgg   3000
cgcggccaac atcggcgccc tgggcaccgc cctgctgtgc tacgtgacgc ccaaggagca   3060
cctgggcctg cccaaccgcg acgacgtgaa ggcgggcgtc atcgcctaca agatcgccgc   3120
ccacgcggcc gacctggcca agcagcaccc ccacgcccag gcgtgggacg acgcgctgtc   3180
```

```
caaggcgcgc ttcgagttcc gctggatgga ccagttcgcg ctgtccctgg accccatgac   3240

ggcgatgtcc ttccacgacg agacgctgcc cgcggacggc gcgaaggtcg cccacttctg   3300

ctccatgtgc ggccccaagt tctgctccat gaagatcacg gaggacatcc gcaagtacgc   3360

cgaggagaac ggctacggct ccgccgagga ggccatccgc cagggcatgg acgccatgtc   3420

cgaggagttc aacatcgcca agaagacgat ctccggcgag cagcacggcg aggtcggcgg   3480

cgagatctac ctgcccgagt cctacgtcaa ggccgcgcag aagtgagtcc tggcgaccct   3540

gctcccctga cccctgttcc cctgcgctgc ttctccccgg tgacatccga cctgctgcaa   3600

aattcccgtt cctgcacaac acttgcctga ccgagggtcg ggtcgcgaag taaaagccac   3660

aatcaacacc ccaggcacat taagagtgca cagcatgacg cagcataggg tttgtgtcgg   3720

aggaaggggg tcgagtcgcg ttggcgaggg ggtggtcacg atgaccacat ctgcgggata   3780

attgaatcct caggggaaaa taccagtctc tgcttccagg tgctccggag ctccgcgatt   3840

gtcagatggt ggagtgggtg gatggccctg ctccagagga gcgttctagg gcgcaaactt   3900

ggcactttcc cccctctgat gcagtgtggg gggacgcggt gtgctatttc tccgagggcc   3960

gcccaaccag ggtggggcgg gcatatgccc gcgtcgacag gtgggtgtgg cctcgaggtg   4020

ttgagaggag ggttatgtcg acagccaaag tggagactga gtgaacccta ctccaggtgc   4080

tgtcgtggga gcgcactgcg cccaccgtgg ctggactgct cgtattccaa ccttggtgcc   4140

cagaaacagg gcaaagccgg tcatcagtgc agcatgagac tcaagctccc taactcatga   4200

ccgttggcat aggcagaagc tgcggcagca cctggtggag gcctgccagg caaacggtgt   4260

caccttccag ccgggggagg tagtggatgt gggcgtgaag aacggcacag cctcggtcac   4320

ctgccgagac ggctccgtcc tgactgcgag gtgggcgctg tgcatggcac ttgttggcac   4380

gagtctgcat ccctgaagct gctgggtagc gtcagagcag tggcgtcaac agcacacagc   4440

tctggcggtg cccagggaac atacatcgct ctgtttcctg gagttgcggg ccctctgtgt   4500

ggcagccagg gccccccgac gcatgcatgc ctcctcgcac atcccgcaca ggctggtgac   4560

cctggcctcc ggcgcggcgg cggggcgctt cctcaagtac gagagaagct t            4611
```

<210> SEQ ID NO 3
<211> LENGTH: 2081
<212> TYPE: DNA
<213> ORGANISM: Artificial Sequence
<220> FEATURE:
<223> OTHER INFORMATION: Nucleotide sequence of the CrBKT1 expression module from pPB0120

<400> SEQUENCE: 3

```
ggtacccttg cagtgcccca aaaactggct accacctaac aattctcacg cagttttatc     60

ctctgcactt tgatgtcagc tttttgattc gtctgcgtac attacagcgt tgagtggcca    120

gcaggaagga gaccgcggtc cgagacgagt ctgagggcgc gctctcgcaa cttggattcc    180

ggatttctta ccctgcatcg acctcggcct ggagtcgatc agaaattgtc attgccagat    240

tgcctggcga ggacgggtga tatactcaag gcgttgcatc gcccacaaaa cacacactta    300

tctgcaaggg agttactgca tcaggctctg ctcaacagct cgtgacatcg atcgttcagc    360

tccccagcag gtgcgtgtcc gcatggagca cccctcccga gacacctgcg ttgggtgtcg    420

gaggagctca catgccaggg aggtgcccac attgcaccac gcgaccgcga aataggcaga    480

cttcgggcat cctgtcatcg catgtccgct ggccgggaat catggcctcc ccaccaggcg    540

tcacgcgctg cccacctccc tcccttgct gcgcagggca ccgcgttcct gtggagagcc    600
```

```
gaccacatgg gccccggcat ccagcccacc tccgcccgcc cctgctcccg caccaagcac    660

tcccgcttcg ccctgctggc cgccgccctg accgcccgcc gcgtgaagca gttcaccaag    720

cagttccgct cccgccgcat ggccgaggac atcctgaagc tgtggcagcg ccagtaccac    780

ctgccccgcg aggactccga caagcgcacc ctgcgcgagc gcgtgcacct gtaccgcccc    840

ccccgctccg acctgggcgg catcgccgtg gccgtgaccg tgatcgccct gtgggccacc    900

ctgttcgtgt acggcctgtg gttcgtgaag ctgccctggg ccctgaaggt gggcgagacc    960

gccacctcct gggccaccat cgccgccgtg ttcttctccc tggagttcct gtacaccggc   1020

ctgttcatca ccacccacga cgccatgcac ggcaccatcg ccctgcgcaa ccgccgcctg   1080

aacgacttcc tgggccagct cgcgatctcc ctgtacgcct ggttcgacta ctccgtgctg   1140

caccgcaagc actgggagca ccacaaccac accggcgagc cccgcgtgga ccccgacttc   1200

caccgcggca accccaacct ggccgtgtgg ttcgcccagt tcatggtgtc ctacatgacc   1260

ctgtcccagt tcctgaagat cgccgtgtgg tccaacctgc tgctgctggc cggcgccccc   1320

ctggccaacc agctgctgtt catgaccgcc gcccccatcc tgtccgcctt ccgcctgttc   1380

tactacggca cctacgtgcc ccaccacccc gagaagggcc acaccggcgc catgccctgg   1440

caggtgtccc gcacctcctc cgcctcccgc ctgcagtcct tcctgacctg ctaccacttc   1500

gacctccact gggagcacca ccgctggccc tacgcccccct ggtgggagct gcccaagtgc   1560

cgccagatcg cccgcggcgc cgccctggcc tgagcggagg ccttggaaat attcgcgtca   1620

cgcgaggagt aggctctgct ggtcggccct ggatacgctg actcttcaag cagtggggca   1680

ccacacccac cttttgccaa gggcaaggag tcggaagggg gcggggctgc catgcacccc   1740

tgacgggcat ggccgttccg cgagggcgcc aactgcggcg gcctgcccgc tggctcgtgc   1800

ccccctaccc ccaccattgc ctggagcgtt tccatcccca aatcacattc catccaagtt   1860

gtatcactat gccccttttgg ctctatacac tcacggcctg aggtcccttc tcggccgtgg   1920

cggcacacgc ccaacccccc accatactct ttccatacac tgcaatgctt cgagcctgcc   1980

tgccacctgc tctgcttgtc tcccctccct tcccttgagg ttttccaatg cagtaagaga   2040

agtcgacgtg catggacaga tgattgagag atgagactag t                       2081
```

<210> SEQ ID NO 4
<211> LENGTH: 981
<212> TYPE: DNA
<213> ORGANISM: Artificial Sequence
<220> FEATURE:
<223> OTHER INFORMATION: Nucleotide sequence of the ApSAD2tp_CrBKT1 expression module from pPB0123

<400> SEQUENCE: 4

```
atggccaccg catccacttt ctcggcgttc aatgcccgct gcggcgacct gcgtcgctcg     60

gcgggctccg ggccccggcg cccagcgagg cccctccccg tgcgcgctgc catccgctcc    120

cgccgcatgg ccgaggacat cctgaagctg tggcagcgcc agtaccacct gccccgcgag    180

gactccgaca agcgcaccct gcgcgagcgc gtgcacctgt accgcccccc ccgctccgac    240

ctgggcggca tcgccgtggc cgtgaccgtg atcgccctgt gggccaccct gttcgtgtac    300

ggcctgtggt tcgtgaagct gccctgggcc ctgaaggtgg gcgagaccgc cacctcctgg    360

gccaccatcg ccgccgtgtt cttctccctg gagttcctgt acaccggcct gttcatcacc    420

acccacgacg ccatgcacgg caccatcgcc ctgcgcaacc gccgcctgaa cgacttcctg    480

ggccagctcg cgatctccct gtacgcctgg ttcgactact ccgtgctgca ccgcaagcac    540
```

```
tgggagcacc acaaccacac cggcgagccc cgcgtggacc ccgacttcca ccgcggcaac    600

cccaacctgg ccgtgtggtt cgcccagttc atggtgtcct acatgaccct gtcccagttc    660

ctgaagatcg ccgtgtggtc caacctgctg ctgctggccg gcgccccct ggccaaccag    720

ctgctgttca tgaccgccgc ccccatcctg tccgccttcc gcctgttcta ctacggcacc    780

tacgtgcccc accaccccga gaagggccac accggcgcca tgccctggca ggtgtcccgc    840

acctcctccg cctcccgcct gcagtccttc ctgacctgct accacttcga cctccactgg    900

gagcaccacc gctggcccta cgccccctgg tgggagctgc ccaagtgccg ccagatcgcc    960

cgcggcgccg ccctggcctg a                                              981
```

<210> SEQ ID NO 5
<211> LENGTH: 328
<212> TYPE: PRT
<213> ORGANISM: Artificial Sequence
<220> FEATURE:
<223> OTHER INFORMATION: Amino acid sequence of native CrBKT1

<400> SEQUENCE: 5

```
Met Gly Pro Gly Ile Gln Pro Thr Ser Ala Arg Pro Cys Ser Arg Thr
1               5                   10                  15

Lys His Ser Arg Phe Ala Leu Leu Ala Ala Ala Leu Thr Ala Arg Arg
            20                  25                  30

Val Lys Gln Phe Thr Lys Gln Phe Arg Ser Arg Arg Met Ala Glu Asp
        35                  40                  45

Ile Leu Lys Leu Trp Gln Arg Gln Tyr His Leu Pro Arg Glu Asp Ser
    50                  55                  60

Asp Lys Arg Thr Leu Arg Glu Arg Val His Leu Tyr Arg Pro Pro Arg
65                  70                  75                  80

Ser Asp Leu Gly Gly Ile Ala Val Ala Val Thr Val Ile Ala Leu Trp
                85                  90                  95

Ala Thr Leu Phe Val Tyr Gly Leu Trp Phe Val Lys Leu Pro Trp Ala
            100                 105                 110

Leu Lys Val Gly Glu Thr Ala Thr Ser Trp Ala Thr Ile Ala Ala Val
        115                 120                 125

Phe Phe Ser Leu Glu Phe Leu Tyr Thr Gly Leu Phe Ile Thr Thr His
    130                 135                 140

Asp Ala Met His Gly Thr Ile Ala Leu Arg Asn Arg Arg Leu Asn Asp
145                 150                 155                 160

Phe Leu Gly Gln Leu Ala Ile Ser Leu Tyr Ala Trp Phe Asp Tyr Ser
                165                 170                 175

Val Leu His Arg Lys His Trp Glu His His Asn His Thr Gly Glu Pro
            180                 185                 190

Arg Val Asp Pro Asp Phe His Arg Gly Asn Pro Asn Leu Ala Val Trp
        195                 200                 205

Phe Ala Gln Phe Met Val Ser Tyr Met Thr Leu Ser Gln Phe Leu Lys
    210                 215                 220

Ile Ala Val Trp Ser Asn Leu Leu Leu Leu Ala Gly Ala Pro Leu Ala
225                 230                 235                 240

Asn Gln Leu Leu Phe Met Thr Ala Ala Pro Ile Leu Ser Ala Phe Arg
                245                 250                 255

Leu Phe Tyr Tyr Gly Thr Tyr Val Pro His His Pro Glu Lys Gly His
            260                 265                 270

Thr Gly Ala Met Pro Trp Gln Val Ser Arg Thr Ser Ser Ala Ser Arg
```

```
        275                 280                 285

Leu Gln Ser Phe Leu Thr Cys Tyr His Phe Asp Leu His Trp Glu His
    290                 295                 300

His Arg Trp Pro Tyr Ala Pro Trp Trp Glu Leu Pro Lys Cys Arg Gln
305                 310                 315                 320

Ile Ala Arg Gly Ala Ala Leu Ala
                325


<210> SEQ ID NO 6
<211> LENGTH: 326
<212> TYPE: PRT
<213> ORGANISM: Artificial Sequence
<220> FEATURE:
<223> OTHER INFORMATION: Amino acid sequence of chimeric ApSAD2tp_CrBKT1

<400> SEQUENCE: 6

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Arg Ser Arg Arg Met Ala Glu Asp Ile Leu
        35                  40                  45

Lys Leu Trp Gln Arg Gln Tyr His Leu Pro Arg Glu Asp Ser Asp Lys
    50                  55                  60

Arg Thr Leu Arg Glu Arg Val His Leu Tyr Arg Pro Pro Arg Ser Asp
65                  70                  75                  80

Leu Gly Gly Ile Ala Val Ala Val Thr Val Ile Ala Leu Trp Ala Thr
                85                  90                  95

Leu Phe Val Tyr Gly Leu Trp Phe Val Lys Leu Pro Trp Ala Leu Lys
            100                 105                 110

Val Gly Glu Thr Ala Thr Ser Trp Ala Thr Ile Ala Ala Val Phe Phe
        115                 120                 125

Ser Leu Glu Phe Leu Tyr Thr Gly Leu Phe Ile Thr Thr His Asp Ala
    130                 135                 140

Met His Gly Thr Ile Ala Leu Arg Asn Arg Arg Leu Asn Asp Phe Leu
145                 150                 155                 160

Gly Gln Leu Ala Ile Ser Leu Tyr Ala Trp Phe Asp Tyr Ser Val Leu
                165                 170                 175

His Arg Lys His Trp Glu His His Asn His Thr Gly Glu Pro Arg Val
            180                 185                 190

Asp Pro Asp Phe His Arg Gly Asn Pro Asn Leu Ala Val Trp Phe Ala
        195                 200                 205

Gln Phe Met Val Ser Tyr Met Thr Leu Ser Gln Phe Leu Lys Ile Ala
    210                 215                 220

Val Trp Ser Asn Leu Leu Leu Leu Ala Gly Ala Pro Leu Ala Asn Gln
225                 230                 235                 240

Leu Leu Phe Met Thr Ala Ala Pro Ile Leu Ser Ala Phe Arg Leu Phe
                245                 250                 255

Tyr Tyr Gly Thr Tyr Val Pro His His Pro Glu Lys Gly His Thr Gly
            260                 265                 270

Ala Met Pro Trp Gln Val Ser Arg Thr Ser Ser Ala Ser Arg Leu Gln
        275                 280                 285

Ser Phe Leu Thr Cys Tyr His Phe Asp Leu His Trp Glu His His Arg
    290                 295                 300

Trp Pro Tyr Ala Pro Trp Trp Glu Leu Pro Lys Cys Arg Gln Ile Ala
```

-continued 305 310 315 320

Arg Gly Ala Ala Leu Ala
325

<210> SEQ ID NO 7
<211> LENGTH: 4637
<212> TYPE: DNA
<213> ORGANISM: Artificial Sequence
<220> FEATURE:
<223> OTHER INFORMATION: Nucleotide sequence of the transforming DNA from pPB0065

<400> SEQUENCE: 7
aagctttcac tgctccattc acacccaatt tcccaccgcc gcacccgctc ccaggtggga 60
ggatgggagg gaacccagct gggagccgga ggagcatgtg accccggacc tgatcgagct 120
atatgccgcc agggacgctc gagcacggga tgtcaaggcc gcggctgaca aggctggcaa 180
gggtaggaca cctgcgttga ggcaaacgct ggagacggcc ggtctcagca tgtgatcctg 240
tacttgctgt gacaaggtgg acaatgcagt acgaggtgta ccaggctaag tattcctagt 300
ataccggcac gccagatcat ctgtacagga gtctgtgcag gagtgaaaag gtaagagcca 360
gagccatgac cggcgaccat ccatgtcccg tcactcggat gcactggctg acatcggcgg 420
caggtcatcc aacggtcctg aatgatcgag aggaagctgc ccgatttcaa aacgcccccc 480
cacgtcgccc tccatggccg cacagcatgc tcagcacagg ttgctgcgtg tcctcacaca 540
aactgctcct ttaaagcgat caactttcca gggcatgggg cactcgtact gacaatcacc 600
cacattcgta tacctttgac gtcattattt tttcgcccca acgcggttgc catcccgagt 660
tgtacctccg cggctaccat acccctgtct tctggccctc accgtcgctc gcaggcggga 720
tccagcgcag ccagtctgaa tacttttaca caacatagta cgtaacgcgc attaggcccc 780
caataccagc agctggctcc agcatgggca agggtgcgcg gcaggaggaa ttctcccgct 840
ttttaattga gccccttcg tcgctgaatc agcgaaagca ccgcgaaaca atgcctgtcc 900
cgtccatgca tctcaacagc ctcatgcaag gtttgcacaa gcaagaccat tctgatctgg 960
gaacttgtag gtgttgtatg ggggaggttg tgctcttgaa tcaagtggta tcacgtttcc 1020
ggaacacccc gaaacgtgca tgggcttatt gcgatgagag catttcccac cgcgattgtc 1080
tcacgcgcat ttcggagaag gtttgcagaa cactccagga catgaaatgc cttgtcacgt 1140
atgaaccatc tcccacggcc ttgaaaagat cgctcgactt ccattctaga tggtgcaaaa 1200
ccctacgact caagaaggtg ccaccgactc aggcattggg cacggcgggc agggagaaga 1260
gaggagttga tcaaaactgc tcgatcacgt tcccccatgg cgatccgagc agcacatgat 1320
gcatcgaggt ggcgccgttg caaaggagtt gcgcatgggt cgaagcaggg agaaggaaac 1380
ggcgaggcgt gccgcggggg tgaattcaga gtcaaatctg cgcctgcccc ggcgctcctg 1440
acggggatta acccccacga ctgtatccat cgacactcgt ctcgggggaa taaaagcggc 1500
gacccagctc cagaggcgca atccttctca caatctgttt aactttcaac aaagtataag 1560
tcaattcaac ttgacacaat ggccgcgtcc gtccactgca ccctgatgtc cgtggtctgc 1620
aacaacaaga accactccgc ccgccccaag ctgcccaact cctccctgct gcccggcttc 1680
gacgtggtgg tccaggccgc ggccacccgc ttcaagaagg agacgacgac cacccgcgcc 1740
acgctgacgt tcgacccccc cacgaccaac tccgagcgcg ccaagcagcg caagcacacc 1800
atcgacccct cctcccccga cttccagccc atcccctcct tcgaggagtg cttccccaag 1860
tccacgaagg agcacaagga ggtggtgcac gaggagtccg gccacgtcct gaaggtgccc 1920

```
ttccgccgcg tgcacctgtc cggcggcgag cccgccttcg acaactacga cacgtccggc   1980
ccccagaacg tcaacgccca catcggcctg gcgaagctgc gcaaggagtg gatcgaccgc   2040
cgcgagaagc tgggcacgcc ccgctacacg cagatgtact acgcgaagca gggcatcatc   2100
acggaggaga tgctgtactg cgcgacgcgc gagaagctgg accccgagtt cgtccgctcc   2160
gaggtcgcgc ggggccgcgc catcatcccc tccaacaaga agcacctgga gctggagccc   2220
atgatcgtgg gccgcaagtt cctggtgaag gtgaacgcga acatcggcaa ctccgccgtg   2280
gcctcctcca tcgaggagga ggtctacaag gtgcagtggg ccaccatgtg gggcgccgac   2340
accatcatgg acctgtccac gggccgccac atccacgaga cgcgcgagtg gatcctgcgc   2400
aactccgcgg tccccgtggg caccgtcccc atctaccagg cgctggagaa ggtggacggc   2460
atcgcggaga acctgaactg ggaggtgttc cgcgagacgc tgatcgagca ggccgagcag   2520
ggcgtggact acttcacgat ccacgcgggc gtgctgctgc gctacatccc cctgaccgcc   2580
aagcgcctga cgggcatcgt gtcccgcggc ggctccatcc acgcgaagtg gtgcctggcc   2640
taccacaagg agaacttcgc ctacgagcac tgggacgaca tcctggacat ctgcaaccag   2700
tacgacgtcg ccctgtccat cggcgacggc ctgcgccccg gctccatcta cgacgccaac   2760
gacacggccc agttcgccga gctgctgacc cagggcgagc tgacgcgccg cgcgtgggag   2820
aaggacgtgc aggtgatgaa cgagggcccc ggccacgtgc ccatgcacaa gatccccgag   2880
aacatgcaga agcagctgga gtggtgcaac gaggcgccct tctacaccct gggccccctg   2940
acgaccgaca tcgcgcccgg ctacgaccac atcacctccg ccatcggcgc ggccaacatc   3000
ggcgccctgg gcaccgccct gctgtgctac gtgacgccca aggagcacct gggcctgccc   3060
aaccgcgacg acgtgaaggc gggcgtcatc gcctacaaga tcgccgccca cgcggccgac   3120
ctggccaagc agcaccccca cgcccaggcg tgggacgacg cgctgtccaa ggcgcgcttc   3180
gagttccgct ggatggacca gttcgcgctg tccctggacc ccatgacggc gatgtccttc   3240
cacgacgaga cgctgcccgc ggacggcgcg aaggtcgccc acttctgctc catgtgcggc   3300
cccaagttct gctccatgaa gatcacggag gacatccgca agtacgccga ggagaacggc   3360
tacggctccg ccgaggaggc catccgccag ggcatggacg ccatgtccga ggagttcaac   3420
atcgccaaga agacgatctc cggcgagcag cacggcgagg tcggcggcga gatctacctg   3480
cccgagtcct acgtcaaggc cgcgcagaag tgagtcctgg cgaccctgct cccctgaccc   3540
ctgttcccct gcgctgcttc tccccggtga catccgacct gctgcaaaat tcccgttcct   3600
gcacaacact tgcctgaccg agggtcgggt cgcgaagtaa aagccacaat caacacccca   3660
ggcacattaa gagtgcacag catgacgcag catagggttt gtgtcggagg aagggggtcg   3720
agtcgcgttg gcgagggggt ggtcacgatg accacatctg cgggataatt gaatcctcag   3780
gggaaaatac cagtctctgc ttccaggtgc tccggagctc cccaggcgag tcaatcagtt   3840
gtgtcatgag attgatctgc ctgttgcaga tcccccgacc cgctgccggc ccctctgccg   3900
tgcgacaccc cttgccctgg ggtgtgcctc ttgtcctgca tcgcacacct cctccgccgg   3960
accttcaccc cctcccacct cgacacaagc aggtgtggga cgtgatagtg gtgggcgcgg   4020
gcgtggccgg cgcggcgctg gcgcatcagc agggcttgga cggccgacgc gtgctgctcc   4080
tcgagcggga tctggcccag cccgaccgca tcgtgggcga gctgctgcag cctggcggcg   4140
tgctggccct ggagcgcctg ggcctgggcg gcgccgtgga cggcatcgac gcgcagcccg   4200
tggtcgggta ctgcatgttc aagggcgggc gcgaggcgtg catcgcctac cccacccccg   4260
```

```
ccgagctggg gggtccagcg gctgcggctg cggcatgcag gggccccact ggaagcgcca   4320

gcgccgcgcc cgccggcgac gcccccgtca cgggcttctc cttccacaac gggcgattcg   4380

tgcagcggct gcgcgccgcg gcggcggctg cgcccggggt cacgctgcgt cgcggcacgg   4440

tgcgcgcgct ggtggatgac gccggcgcgg actgggagga ggggcgcgtg gtgacgggcg   4500

tgcggtaccg cgcgggcgac ggcggcgagc gcgtggcact gggccacctc accgtggtct   4560

gcgacggcat gtactcggcc ctgcggtcca agctggcggt gcccgacctg cgcacgccct   4620

cccacttcat caagctt                                                  4637
```

<210> SEQ ID NO 8
<211> LENGTH: 3767
<212> TYPE: DNA
<213> ORGANISM: Artificial Sequence
<220> FEATURE:
<223> OTHER INFORMATION: Nucleotide sequence of the transforming DNA from pPB0077

<400> SEQUENCE: 8

```
aagctttcac tgctccattc acacccaatt tcccaccgcc gcacccgctc ccaggtggga     60

ggatgggagg gaacccagct gggagccaga ggagcatgtg accccggacc tgatcaagct    120

atatgccgcc agggacgctc gagcacggga tgtcaaggcc gcggctgaca aggctggcaa    180

gggcaggaca cctgcgccga ggcaaacgct ggagacggcc ggtctcagca tgtgatcctg    240

tacttgctgt gacaaggtgg acaatgcagt acgagttgta ccaggctaag tatccctagt    300

ataccggcac gccagatcat ctgtacagga gtctgtgcag gagtaaaaag gcaacagcca    360

gagccatgac cggcgactat ccacatcccg tcactccgat gcactggctg acatcggcgg    420

caggtcgtcc aacggtcctg aatgatcgag aggaagctgc ccgatttcac cccccccccc    480

cacgtcgccc tccatggccg cacagcatgc tcagcacagg ttgctgcgtg tcctcacaca    540

aactgctcct ttaaagcgat caactttcca gggcatgggg cactcgtact gacaatcacc    600

cacattcgta tacctttgac gtcatttttt tttcgcccca acgcggttgc catcccgagt    660

tgtacctccg cggctaccat accccctgtct tctggccctc accgtcgctc gcaggcggga    720

tccagcgcag ccagtctgaa tacttttaca caacatagta cgtaacgcgc attaggcccc    780

caataccagc agctggctcc agcatgggca agggtgcgcg gcaggaggaa ttcctttctt    840

gcgctatgac acttccagca aaaggtaggg cgggctgcga gacggcttcc cggcgctgca    900

tgcaacaccg atgatgcttc gaccccccga agctccttcg gggctgcatg ggcgctccga    960

tgccgctcca gggcgagcgc tgtttaaata gccaggcccc cgattgcaaa gacattatag   1020

cgagctacca aagccatatt caaacaccta gatcactacc acttctacac aggccactcg   1080

agcttgtgat cgcactccgc taagggggcg cctcttcctc ttcgtttcag tcacaacccg   1140

caaacatgct gctgcaggcc ttcctgttcc tgctggccgg cttcgccgcc aagatcagcg   1200

cctccatgac gaacgagacg tccgaccgcc ccctggtgca cttcaccccc aacaagggct   1260

ggatgaacga ccccaacggc ctgtggtacg acgagaagga cgccaagtgg cacctgtact   1320

tccagtacaa cccgaacgac accgtctggg ggacgccctt gttctggggc cacgccacgt   1380

ccgacgacct gaccaactgg gaggaccagc ccatcgccat cgccccgaag cgcaacgact   1440

ccggcgcctt ctccggctcc atggtggtgg actacaacaa cacctccggc ttcttcaacg   1500

acaccatcga cccgcgccag cgctgcgtgg ccatctggac ctacaacacc ccggagtccg   1560

aggagcagta catctcctac agcctggacg gcggctacac cttcaccgag taccagaaga   1620
```

```
accccgtgct ggccgccaac tccacccagt tccgcgaccc gaaggtcttc tggtacgagc   1680
cctcccagaa gtggatcatg accgcggcca agtcccagga ctacaagatc gagatctact   1740
cctccgacga cctgaagtcc tggaagctgg agtccgcgtt cgccaacgag ggcttcctcg   1800
gctaccagta cgagtgcccc ggcctgatcg aggtccccac cgagcaggac cccagcaagt   1860
cctactgggt gatgttcatc tccatcaacc ccggcgcccc ggccggcggc tccttcaacc   1920
agtacttcgt cggcagcttc aacggcaccc acttcgaggc cttcgacaac cagtcccgcg   1980
tggtggactt cggcaaggac tactacgccc tgcagacctt cttcaacacc gacccgacct   2040
acgggagcgc cctgggcatc gcgtgggcct ccaactggga gtactccgcc ttcgtgccca   2100
ccaacccctg gcgctcctcc atgtccctcg tgcgcaagtt ctccctcaac accgagtacc   2160
aggccaaccc ggagacggag ctgatcaacc tgaaggccga gccgatcctg aacatcagca   2220
acgccggccc ctggagccgg ttcgccacca acaccacgtt gacgaaggcc aacagctaca   2280
acgtcgacct gtccaacagc accggcaccc tggagttcga gctggtgtac gccgtcaaca   2340
ccacccagac gatctccaag tccgtgttcg cggacctctc cctctggttc aagggcctgg   2400
aggaccccga ggagtacctc cgcatgggct tcgaggtgtc cgcgtcctcc ttcttcctgg   2460
accgcgggaa cagcaaggtg aagttcgtga aggagaaccc ctacttcacc aaccgcatga   2520
gcgtgaacaa ccagcccttc aagagcgaga acgacctgtc ctactacaag gtgtacggct   2580
tgctggacca gaacatcctg gagctgtact tcaacgacgg cgacgtcgtg tccaccaaca   2640
cctacttcat gaccaccggg aacgccctgg gctccgtgaa catgacgacg gggtggaca    2700
acctgttcta catcgacaag ttccaggtgc gcgaggtcaa gtgattgatt ggaactcaca   2760
aagcggccca cggcttcgaa cgtcccgtgt caattgcgcg gggtgtgcca gagtttctgc   2820
gccaccgatg ctcaccctag gggggatgc cctttgacat tcatgtgtgc ctgcatgcac    2880
gtttgtatca gtctcaccac accttgaaga tttttgggag gggggggaa gtcggaatgg    2940
aaacgagctc cccaggcgag tcaatcagtt gtgtcatgag attgatctgc ctgttgcaga   3000
tcccccgacc cgctgccggc ccctctgccg tgcgacaccc cttgccctgg ggtgtgcctc   3060
ttgtcctgca tcgcacacct cctccgccgg accttcaccc cctcccacct cgacacaagc   3120
aggtgtggga cgtgatagtg gtgggcgcgg gcgtggccgg cgcggcgctg gcgcatcagc   3180
agggcttgga cggccgacgc gtgctgctcc tcgagcggga tctggcccag cccgaccgca   3240
tcgtgggcga gctgctgcag cctggcggcg tgctggccct ggagcgcctg ggcctgggcg   3300
gcgccgtgga cggcatcgac gcgcagcccg tggtcgggta ctgcatgttc aagggcgggc   3360
gcgaggcgtg catcgcctac cccacccccg ccgagctggg gggtccagcg gctgcggctg   3420
cggcatgcag gggccccact ggaagcgcca gcgccgcgcc cgccggcgac gcccccgtca   3480
cgggcttctc cttccacaac gggcgattcg tgcagcggct gcgcgccgcg gcggcggctg   3540
cgcccggggt cacgctgcgt cgcggcacgg tgcgcgcgct ggtggatgac gccggcgcgg   3600
actgggagga ggggcgcgtg gtgacgggcg tgcggtaccg cgcgggcgac ggcggcgagc   3660
gcgtggcact gggccacctc accgtggtct gcgacggcat gtactcggcc ctgcggtcca   3720
agctggcggt gcccgacctg cgcacgccct cccacttcat caagctt                 3767
```

<210> SEQ ID NO 9
<211> LENGTH: 730
<212> TYPE: PRT
<213> ORGANISM: Artificial Sequence
<220> FEATURE:
<223> OTHER INFORMATION: Amino acid sequence of A. protothecoides 1-deoxy-D-xylulose 5-phosphate synthase (DXS)

<400> SEQUENCE: 9

```
Met Gln Phe Ser Leu Ala Gly Met Asn Thr Arg Ala Leu Gln Thr Gly
1               5                   10                  15

Ala Arg Pro Ser Leu Pro Ala Ala Arg Pro Ser Arg Arg Val Arg Pro
            20                  25                  30

Ala Arg Arg Ser Ala Pro Cys Pro Val Ala Arg Thr Met Gly Gly Gly
        35                  40                  45

Glu Glu Gln Pro Ser Ser Ala Glu Gly Val Ala Trp Asp Lys Ile Ser
    50                  55                  60

Thr Asp Glu Leu Ala Asp Trp Ala Gly Ala Gly Pro Pro Thr Pro Leu
65                  70                  75                  80

Leu Asp Thr Val Ala Phe Pro Val His Ile Lys Asn Phe Asn Ser Arg
                85                  90                  95

Gln Leu Gln Gln Leu Cys Lys Glu Leu Arg Ala Asp Leu Ile His Thr
            100                 105                 110

Val Ala Lys Thr Gly Gly His Leu Gly Ser Ser Leu Gly Val Val Glu
        115                 120                 125

Leu Thr Val Ala Leu His His Val Phe Asn Thr Pro Glu Asp Arg Ile
    130                 135                 140

Val Trp Asp Val Gly His Gln Ala Tyr Ile His Lys Met Leu Thr Gly
145                 150                 155                 160

Arg Arg Ala Arg Met His Thr Ile Arg Gln Gln Gly Gly Leu Ser Gly
                165                 170                 175

Phe Thr Arg Arg Ala Glu Ser Val Tyr Asp Pro Phe Gly Ala Gly His
            180                 185                 190

Ser Ser Thr Ser Val Ser Ala Ala Leu Gly Met Ala Val Gly Arg Asp
        195                 200                 205

Arg Lys Gly Arg Ala Asn Asn Cys Ile Ala Val Ile Gly Asp Gly Ala
    210                 215                 220

Ile Thr Gly Gly Met Ala Tyr Glu Ala Met Asn His Ala Gly Phe Leu
225                 230                 235                 240

Asp Thr Asn Met Ile Val Ile Leu Asn Asp Asn Gln Gln Val Ser Leu
                245                 250                 255

Pro Thr Gln Tyr Asn Gly Lys Asn Gln Glu Pro Val Gly Ala Leu Ser
            260                 265                 270

Ser Ala Leu Ala Arg Leu Gln Ala Asn Arg Gln Leu Arg Glu Leu Arg
        275                 280                 285

Glu Ile Ala Lys Gly Val Thr Lys Gln Leu Pro Asp Val Ile Gln Asn
    290                 295                 300

Ala Thr Ala Lys Ile Asp Glu Tyr Ala Arg Gly Met Ile Ser Gly Thr
305                 310                 315                 320

Gly Ser Thr Leu Phe Glu Glu Leu Gly Phe Tyr Tyr Ile Gly Pro Val
                325                 330                 335

Asp Gly His Asn Met Gln Asp Leu Val Asp Val Leu Ser Glu Ile Lys
            340                 345                 350

Ala Thr Glu Thr Val Gly Pro Val Leu Leu His Val Val Thr Gln Lys
        355                 360                 365

Gly Arg Gly Tyr Thr Pro Ala Glu Thr Ala Ser Asp Arg Met His Gly
    370                 375                 380

Val Val Gln Tyr Asp Thr Leu Thr Gly Lys Gln Lys Lys Gly Ser Gly
385                 390                 395                 400
```

```
Gly Pro Gln Ser Tyr Thr Asn Tyr Phe Ala Asp Ala Leu Val Ala Glu
                405                 410                 415

Ala Lys Arg Asp Ala Arg Val Leu Gly Ile His Ala Ala Met Gly Gly
            420                 425                 430

Gly Thr Gly Met Asn Arg Phe Glu Ala Ala Phe Pro Asp Arg Val Phe
        435                 440                 445

Asp Thr Gly Ile Ala Glu Gln His Ala Val Thr Phe Ala Ala Gly Leu
    450                 455                 460

Ala Thr Glu Gly Leu Val Pro Phe Val Ala Ile Tyr Ser Thr Phe Leu
465                 470                 475                 480

Gln Arg Gly Tyr Asp Gln Ile Val His Asp Val Ser Leu Gln Ser Leu
                485                 490                 495

Pro Val Arg Phe Ala Leu Asp Arg Ala Gly Asn Val Gly Ala Asp Gly
            500                 505                 510

Ala Thr His Ala Gly Ala Phe Asp Val Thr Tyr Leu Ala Cys Leu Pro
        515                 520                 525

Asn Met Val Val Met Ala Pro Ser Asn Glu Ala Glu Leu Val His Ala
    530                 535                 540

Val Ala Thr Ala Ala Ala Ile Asp Asp Arg Pro Ser Ala Phe Arg Phe
545                 550                 555                 560

Pro Arg Gly Asn Gly Leu Gly Val Asp Leu Ala Ala Ala Gly Val Thr
                565                 570                 575

Asp Asp Leu Lys Gly Gln Pro Met Glu Val Gly Arg Gly Val Val Arg
            580                 585                 590

Arg Gly Gly Ala Asp Val Ala Leu Leu Gly Tyr Gly Thr Cys Val Asn
        595                 600                 605

Ala Cys Leu Ala Ala Ala Asp Leu Leu Ala Ala Gln Gly Val Ser Ala
    610                 615                 620

Thr Val Val Asp Ala Arg Phe Cys Lys Pro Leu Asp Thr Ala Leu Val
625                 630                 635                 640

Arg Arg Met Ala Ala Glu His Pro Val Met Ile Thr Val Glu Glu Gly
                645                 650                 655

Ser Ile Gly Gly Phe Ala Ala His Val Met Gln Phe Leu Ala Leu Glu
            660                 665                 670

Gly Leu Leu Asp Gly Lys Leu Lys Phe Arg Pro Met Thr Leu Pro Asp
        675                 680                 685

Arg Tyr Ile Glu His Gly Thr Gln Ala Glu Gln Met Ala Glu Ala Gly
    690                 695                 700

Leu Thr Ala Ser His Ile Ala Gly Thr Ala Leu Ser Val Met Gly Val
705                 710                 715                 720

Lys Arg Asp Ala Pro Ser Ile Phe Ser Thr
                725                 730


<210> SEQ ID NO 10
<211> LENGTH: 453
<212> TYPE: PRT
<213> ORGANISM: Artificial Sequence
<220> FEATURE:
<223> OTHER INFORMATION: Amino acid sequence of A. protothecoides
      1-deoxy-D-xylulose 5-phosphate reductoisomerase (DXR)

<400> SEQUENCE: 10

Met Arg Cys Ser Ala Gln Leu Asn Thr Arg Gly Pro Thr Leu Pro Asn
1               5                   10                  15

Ser Ala Arg Pro Arg Thr Cys Arg Val Val Ser Ala Ser Ala Ala Pro
            20                  25                  30
```

```
Val Pro Ser Ala Trp Pro Gly Arg Val Val Leu Pro Glu Lys Ser Ala
        35                  40                  45

Ser Arg Thr Gly Pro Lys Lys Phe Ser Leu Leu Gly Ser Thr Gly Ser
    50                  55                  60

Ile Gly Thr Gln Thr Leu Asp Ile Val Ala Glu His Pro Asp Arg Phe
65                  70                  75                  80

Gln Val Val Ser Leu Ala Ala Gly Gly Asn Val Ala Leu Leu Ala Glu
                85                  90                  95

Gln Ile Ala Arg Phe Ser Pro Ser Leu Val Ser Val Arg Asp Ser Gly
            100                 105                 110

Gly Ala Arg Ala Leu Glu Ala Ala Leu Asp Ala Ala Gly Val Asp Arg
        115                 120                 125

Arg Pro Glu Ile Gln Ile Gly Ala Ala Gly Ile Asp Ala Val Ala Ala
    130                 135                 140

His Pro Glu Ala Asp Ala Cys Val Thr Gly Ile Val Gly Cys Ala Gly
145                 150                 155                 160

Leu Arg Pro Thr Met Ala Ala Ile Glu Ala Gly Lys Asp Ile Cys Leu
                165                 170                 175

Ala Asn Lys Glu Thr Leu Ile Ala Gly Gly Pro Thr Val Leu Pro Ala
            180                 185                 190

Ala Ala Lys His Gly Val Ser Ile Leu Pro Ala Asp Ser Glu His Ser
        195                 200                 205

Ala Ile Phe Gln Cys Leu Gln Gly Leu Pro Glu Gly Gly Leu Arg Arg
    210                 215                 220

Ile Ile Leu Thr Ala Ser Gly Gly Ala Phe Arg Asp Leu Pro Val Ser
225                 230                 235                 240

Glu Leu Pro Lys Val Thr Val Ala Asp Ala Leu Lys His Pro Asn Trp
                245                 250                 255

Ala Met Gly Lys Lys Ile Thr Ile Asp Ser Ala Thr Leu Met Asn Lys
            260                 265                 270

Gly Leu Glu Val Ile Glu Ala His Tyr Leu Phe Gly Ala Ser Tyr Asp
        275                 280                 285

Asn Ile Asp Ile Val Ile His Pro Gln Ser Ile Val His Ser Met Ile
    290                 295                 300

Glu Thr Gln Asp Ser Ser Val Leu Ala Gln Leu Gly Trp Pro Asp Met
305                 310                 315                 320

Arg Leu Pro Ile Leu Tyr Thr Met Ser Trp Pro Glu Arg Val Pro Cys
                325                 330                 335

Ser Glu Val Thr Trp Pro Arg Leu Asp Phe Val Lys Ala Gly Asn Leu
            340                 345                 350

Thr Phe Arg Gln Pro Asp His Ala Lys Tyr Pro Ala Met Glu Leu Ala
        355                 360                 365

Tyr Ser Ala Gly Arg Ala Gly Gly Thr Met Thr Gly Val Met Ser Ala
    370                 375                 380

Ala Asn Glu Ala Ala Val Glu Leu Phe Leu Glu Glu Ala Ile Gly Tyr
385                 390                 395                 400

Leu Asp Ile Val Pro Val Val Glu Ala Ala Cys Glu Ala His Arg Val
                405                 410                 415

Glu Leu Val Glu Arg Pro Ser Leu Glu Glu Ile Val His Tyr Asp Gln
            420                 425                 430

Trp Ala Arg Arg His Val Arg Glu Ser Val Ala Lys Arg Ala Pro Ala
        435                 440                 445
```

```
Ala Val Pro Ala Leu
    450


<210> SEQ ID NO 11
<211> LENGTH: 359
<212> TYPE: PRT
<213> ORGANISM: Artificial Sequence
<220> FEATURE:
<223> OTHER INFORMATION: Amino acid sequence of A. protothecoides
      farnesyl diphosphate synthase (FDPS)

<400> SEQUENCE: 11

Met Ala Ala Val Val Glu Ala Gly His Ala Ala Ser Lys Gln Lys Thr
1               5                   10                  15

Glu Ala His Gln Thr Lys Gln Glu Phe Leu Ala Val Phe Glu Lys Leu
            20                  25                  30

Arg Asp Glu Leu Leu Glu Asp Ser Ile Leu Ala Gly Gln Pro Glu Ser
        35                  40                  45

Ser Lys Asp Trp Leu Arg Thr Met Leu Asp Tyr Asn Val Pro His Gly
    50                  55                  60

Lys Leu Asn Arg Gly Met Ala Val Leu Asp Val Leu Leu Ala Ala Arg
65                  70                  75                  80

Gly Gly Asp Val Thr Glu Lys Glu Arg Glu Ala Ala Asn Val Leu Gly
                85                  90                  95

Trp Cys Ile Glu Leu Leu Gln Ala Tyr Phe Leu Val Ala Asp Asp Ile
            100                 105                 110

Met Asp Ser Ser Leu Thr Arg Arg Gly Gln Pro Cys Trp Tyr Arg Gln
        115                 120                 125

Pro His Val Gly Met Val Ala Ile Asn Asp Gly Ile Ile Leu Glu Ser
    130                 135                 140

Cys Ile Tyr Arg Leu Leu Lys Leu His Phe Arg Ala His Pro Ala Tyr
145                 150                 155                 160

Val His Leu Leu Glu Leu Phe His Asp Thr Thr His Arg Thr Ala His
                165                 170                 175

Gly Gln Leu Leu Asp Thr Thr Thr Ala Pro Pro Gly Gly Val Asp Leu
            180                 185                 190

Thr Arg Tyr Thr Glu Gly Thr Tyr Leu Arg Ile Val Thr Tyr Lys Thr
        195                 200                 205

Ala Phe Tyr Thr Ile Tyr Leu Pro Val Ala Cys Gly Leu Ala Leu Ala
    210                 215                 220

Gly Val Thr Asp Glu Ala Ser Leu Ala Leu Ala Glu Asp Leu Ser Val
225                 230                 235                 240

Arg Met Gly Arg Tyr Phe Gln Ile Gln Asp Asp Val Leu Asp Ala Phe
                245                 250                 255

Gly Glu Pro Glu Val Ile Gly Lys Val Gly Thr Asp Ile Gln Asp Ser
            260                 265                 270

Lys Cys Ser Trp Leu Val Val Arg Ala Leu Ala Val Ala Ser Ala Glu
        275                 280                 285

Gln Arg Glu Ala Ile Lys Ala Asn Tyr Gly Arg Asp Asp Ala Glu Ala
    290                 295                 300

Val Glu Ala Val Lys Ala Val Tyr Arg Glu Leu Asp Leu Pro Ala Ala
305                 310                 315                 320

Phe Ala Ala Tyr Glu Gln Glu Ser Tyr Asp Gly Leu Val Gln Ala Ile
                325                 330                 335

Glu Gly Gln Asp Lys Phe Pro Pro Ala Val Phe Met Gly Ile Leu Ala
            340                 345                 350
```

```
Lys Ile Tyr Lys Arg Thr Lys
        355


<210> SEQ ID NO 12
<211> LENGTH: 458
<212> TYPE: PRT
<213> ORGANISM: Artificial Sequence
<220> FEATURE:
<223> OTHER INFORMATION: Amino acid sequence of A. protothecoides
      squalene synthase (SQS)

<400> SEQUENCE: 12

Met Gly Lys Leu Gly Glu Leu Leu Ser His Pro Asp Glu Ile Ile Pro
1               5                   10                  15

Met Ala Ala Met Tyr Leu Ala Ala Arg Arg Ala Ala Val Leu Pro His
            20                  25                  30

Asp Pro Asp Leu Ala Phe Cys Tyr Ser Met Leu Asn Lys Val Ser Arg
        35                  40                  45

Ser Phe Ala Ile Val Ile Gln Gln Leu Pro Glu Gln Leu Arg Asp Ala
    50                  55                  60

Val Cys Val Phe Tyr Leu Val Leu Arg Ala Leu Asp Thr Val Glu Asp
65                  70                  75                  80

Asp Met Ala Ile Asp Gln Ala Glu Lys Val Pro Ile Leu Leu Ser Phe
                85                  90                  95

His Glu Lys Thr Tyr Glu Lys Asp Trp Ser Met Lys Cys Gly His Gly
            100                 105                 110

His Tyr Val Glu Leu Met Glu Gln Tyr Pro Val Val Cys Ala Ala Phe
        115                 120                 125

Gln Gly Leu Glu Pro Gln Tyr Gln Glu Val Ile Thr Asp Ile Cys Arg
    130                 135                 140

Arg Met Gly Ala Gly Met Ala Glu Phe Ile Val Lys Glu Val Glu Thr
145                 150                 155                 160

Val Lys Asp Tyr Asp Leu Tyr Cys His Tyr Val Ala Gly Leu Val Gly
                165                 170                 175

Val Gly Leu Ser Asn Leu Phe Ala Gly Ser Gly Leu Glu Ser Glu Asp
            180                 185                 190

Phe Ala Ser Leu His Glu Leu Ser Asn Gly Met Gly Leu Phe Leu Gln
        195                 200                 205

Lys Thr Asn Ile Ile Arg Asp Tyr Leu Glu Asp Ile Met Glu Glu Pro
    210                 215                 220

Ala Pro Arg Met Phe Trp Pro Lys Glu Ile Trp Gly Lys His Gly Asp
225                 230                 235                 240

Ser Leu Glu Asp Phe Lys Asp Pro Glu Asn Ala Glu Ala Ala Val Ala
                245                 250                 255

Cys Leu Asn Asp Met Ile Ala Asp Ala Leu Arg His Val Asp Ala Ser
            260                 265                 270

Leu Asp Tyr Met Gln Arg Leu Arg Asn Arg Pro Ile Phe Arg Phe Cys
        275                 280                 285

Ala Val Pro Gln Ile Met Ala Ile Gly Thr Leu Ala Ala Cys Phe Asp
    290                 295                 300

Asn Pro Ser Val Phe Thr Gly Val Val Lys Met Arg Arg Gly Gln Thr
305                 310                 315                 320

Ala Lys Ile Met His Asp Val Glu Asp Tyr Ala Asp Leu Leu Ala Tyr
                325                 330                 335

Phe Arg Ala Phe Gly Gln Ala Leu Ala Ala Lys Ala Arg Ala Ala Arg
```

```
        340                 345                 350

Gly Lys Gly Ala Glu Ser Val Gly Arg Ala Ala Glu Arg Val Val Ala
    355                 360                 365

Gly Cys Ser Ala Ala Leu Ala Asp Leu Ser Arg Ala Glu Asn Ala Arg
370                 375                 380

Met Ala Ala Ala Ala Arg Arg Pro Leu Ser Leu Pro Ala Arg Ala Leu
385                 390                 395                 400

Leu Leu Val Ala Ala Leu Leu Tyr Leu Phe Leu Ala Trp Arg Ala Glu
                405                 410                 415

Gly Val Arg Arg Trp Leu Gly Val Asp Ser Pro Pro Ala Ala His Lys
            420                 425                 430

Leu Asp Tyr Tyr Asn Gln Ile Val Ala Ser Met Phe Leu Gly Tyr Ser
        435                 440                 445

Leu Phe Ala Val Gly Thr Gly Arg Arg Pro
    450                 455


<210> SEQ ID NO 13
<211> LENGTH: 5161
<212> TYPE: DNA
<213> ORGANISM: Artificial Sequence
<220> FEATURE:
<223> OTHER INFORMATION: Nucleotide sequence of the transforming DNA
      from pPB0039

<400> SEQUENCE: 13

aagcttgcac agtcagtcgt catccacgaa gtcgcgcccg tctgtccacc ggggtctcct     60

gaacgcagca atctcctcct gagtgtatga gcccgtggcc gggagtttgt atgcagggcg    120

aggcaaggac gaccatgccg ggagaaaccc aaggtgacga agtgacattg tgctcgatca    180

ctccatgcac tgcctcactc gcccatgtac cttggtcatg tactccccag tctgcatctt    240

ggtgttcctg ttcagctcgc ggagctcctc caggcgctgc tcgtcgcggc ggtcccgcga    300

gatgtaaaag gcagggacac ccacccccag ggccactccc agtagagccc cccctacagc    360

aaccagggtg tccggatcgc taaagtcgat gttgatcgcg cggcacggtg gcattatcgg    420

gcgtggatgg ccccatgatc ggtgcaacga aggcgccctc atggcaggtc cgcatggtcg    480

tccattgcag gggatacccg ctcgcacttt cgttgacaat aacatcctcg tatagttgga    540

gaaaggattt gtgatctgtc tctggaggcc cttaaagtcc tgcccctcct ctgctggaac    600

ctgacctctc atgcccctgc gccacgcccc cggatctgat atggctctga tatgggtggc    660

tcgtacctct tggctaggcg acccccctaa gcacgcgtgc gggccagggc acaacattat    720

attttgccct ctccttcgtc aacgctcatt tttttggaat actaacgttt aaaagctctc    780

gggtacctcc cgctttttaa ttgagcccct ttcgtcgctg aatcagcgaa agcaccgcga    840

aacaatgcct gtcccgtcca tgcatctcaa cagcctcatg caaggtttgc acaagcaaga    900

ccattctgat ctgggaactt gtaggtgttg tatgggggag gttgtgctct tgaatcaagt    960

ggtatcacgt ttccggaaca ccccgaaacg tgcatgggct tattgcgatg agagcatttc   1020

ccaccgcgat tgtctcacgc gcatttcgga gaaggtttgc agaacactcc aggacatgaa   1080

atgccttgtc acgtatgaac catctcccac ggccttgaaa agatcgctcg acttccattc   1140

tagatggtgc aaaaccctac gactcaagaa ggtgccaccg actcaggcat tgggcacggc   1200

gggcagggag aagagaggag ttgatcaaaa ctgctcgatc acgttccccc atggcgatcc   1260

gagcagcaca tgatgcatcg aggtggcgcc gttgcaaagg agttgcgcat gggtcgaagc   1320

agggagaagg aaacggcgag gcgtgccgcg ggggtgaatt cagagtcaaa tctgcgcctg   1380
```

```
ccccggcgct cctgacgggg attaacccccc acgactgtat ccatcgacac tcgtctcggg   1440
ggaataaaag cggcgaccca gctccagagg cgcaatcctt ctcacaatct gtttaacttt   1500
caacaaagta taagtcaatt caacttgaca caatggccgc gtccgtccac tgcaccctga   1560
tgtccgtggt ctgcaacaac aagaaccact ccgcccgccc caagctgccc aactcctccc   1620
tgctgcccgg cttcgacgtg gtggtccagg ccgcggccac ccgcttcaag aaggagacga   1680
cgaccacccg cgccacgctg acgttcgacc cccccacgac caactccgag cgcgccaagc   1740
agcgcaagca caccatcgac ccctcctccc ccgacttcca gcccatcccc tccttcgagg   1800
agtgcttccc caagtccacg aaggagcaca aggaggtggt gcacgaggag tccggccacg   1860
tcctgaaggt gcccttccgc cgcgtgcacc tgtccggcgg cgagcccgcc ttcgacaact   1920
acgacacgtc cggcccccag aacgtcaacg cccacatcgg cctggcgaag ctgcgcaagg   1980
agtggatcga ccgccgcgag aagctgggca cgcccccgcta cacgcagatg tactacgcga   2040
agcagggcat catcacggag gagatgctgt actgcgcgac gcgcgagaag ctggaccccg   2100
agttcgtccg ctccgaggtc gcgcggggcc gcgccatcat cccctccaac aagaagcacc   2160
tggagctgga gcccatgatc gtgggccgca agttcctggt gaaggtgaac gcgaacatcg   2220
gcaactccgc cgtggcctcc tccatcgagg aggaggtcta caaggtgcag tgggccacca   2280
tgtggggcgc cgacaccatc atggacctgt ccacgggccg ccacatccac gagacgcgcg   2340
agtggatcct gcgcaactcc gcggtccccg tgggcaccgt ccccatctac caggcgctgg   2400
agaaggtgga cggcatcgcg gagaacctga actgggaggt gttccgcgag acgctgatcg   2460
agcaggccga gcagggcgtg gactacttca cgatccacgc gggcgtgctg ctgcgctaca   2520
tccccctgac cgccaagcgc ctgacgggca tcgtgtcccg cggcggctcc atccacgcga   2580
agtggtgcct ggcctaccac aaggagaact tcgcctacga gcactgggac gacatcctgg   2640
acatctgcaa ccagtacgac gtcgccctgt ccatcggcga cggcctgcgc cccggctcca   2700
tctacgacgc caacgacacg gcccagttcg ccgagctgct gacccagggc gagctgacgc   2760
gccgcgcgtg ggagaaggac gtgcaggtga tgaacgaggg ccccggccac gtgcccatgc   2820
acaagatccc cgagaacatg cagaagcagc tggagtggtg caacgaggcg cccttctaca   2880
ccctgggccc cctgacgacc gacatcgcgc ccggctacga ccacatcacc tccgccatcg   2940
gcgcggccaa catcggcgcc ctgggcaccg ccctgctgtg ctacgtgacg cccaaggagc   3000
acctgggcct gcccaaccgc gacgacgtga aggcgggcgt catcgcctac aagatcgccg   3060
cccacgcggc cgacctggcc aagcagcacc cccacgccca ggcgtgggac gacgcgctgt   3120
ccaaggcgcg cttcgagttc cgctggatgg accagttcgc gctgtccctg gaccccatga   3180
cggcgatgtc cttccacgac gagacgctgc ccgcggacgg cgcgaaggtc gcccacttct   3240
gctccatgtg cggccccaag ttctgctcca tgaagatcac ggaggacatc cgcaagtacg   3300
ccgaggagaa cggctacggc tccgccgagg aggccatccg ccagggcatg gacgccatgt   3360
ccgaggagtt caacatcgcc aagaagacga tctccggcga gcagcacggc gaggtcggcg   3420
gcgagatcta cctgcccgag tcctacgtca aggccgcgca gaagtgagtc ctggcgaccc   3480
tgctccccctg accccctgttc ccctgcgctg cttctccccg gtgacatccg acctgctgca   3540
aaattcccgt tcctgcacaa cacttgcctg accgagggtc gggtcgcgaa gtaaaagcca   3600
caatcaacac cccaggcaca ttaagagtgc acagcatgac gcagcatagg gtttgtgtcg   3660
gaggaagggg gtcgagtcgc gttggcgagg gggtggtcac gatgaccaca tctgcgggat   3720
```

-continued

```
aattgaatcc tcaggggaaa ataccagtct ctgcttccag gtgctccgac tagtcttgca   3780

gtgccccaaa aactggctac cacctaacaa ttctcacgca gttttatcct ctgcactttg   3840

atgtcagctt tttgattcgt ctgcgtacat tacagcgttg agtggccagc aggaaggaga   3900

ccgcggtccg agacgagtct gagggcgcgc tctcgcaact tggattccgg atttcttacc   3960

ctgcatcgac ctcggcctgg agtcgatcag aaattgtcat tgccagattg cctggcgagg   4020

acgggtgata tactcaaggc gttgcatcgc ccacaaaaca cacacttatc tgcaagggag   4080

ttactgcatc aggctctgct caacagctcg tgacatcgat cgttcagctc cccagcaggt   4140

gcgtgtccgc atggagcacc cctcccgaga cacctgcgtt gggtgtcgga ggagctcaca   4200

tgccagggag gtgcccacat tgcaccacgc gaccgcgaaa taggcagact tcgggcatcc   4260

tgtcatcgca tgtccgctgg ccgggaatca tggcctcccc accaggcgtc acgcgctgcc   4320

cacctccctc cccttgctgc gcagggcacc gcgttcctgt ggagagccga ccacatggtc   4380

ctgtgcgctg gtagtttgag ctgcagggcg ccgccttcag gcggtgctag gttggagcgg   4440

gggtccccct tcgtgcgcct gggccaccat gcccgcccac aagctcgcag acggatgtca   4500

gacctcgtaa taaggtccat cgcagcccct gctccgcccc cgctgcgacc tgcatctcag   4560

cctcaagccc cacctgcatc agagaccttc acggtgagtc atgatcgagg tcggcccctg   4620

cagcgctcgt gctccggaaa cgacccgcta ctcaatccct gaaccatgaa tacttcaggg   4680

gggccgcgaa ctggccaacc gccctccctt ctccctccaa gacatccgca acgccatccc   4740

ggcggagtgc tggaagaagg acaccttcaa gtccttcgcc tacctggcgc tagatgtagg   4800

aatcgttgct gccctggccg tgacagcaca tgccgtcaac tcgccatggc tctggccctt   4860

ctactggctg gcgcagggga ccatgttctg ggccctgttt gtcgtcggcc acgactggtg   4920

cggttggagg gggtaatctg gcgaccctgc agggcatgca gtggggacaa gagcatcgcc   4980

aggctccgcc ttgcctgctg atcccagccc gacttggctg gacaatagat gctgtcgggg   5040

acatgccgca gtgcatgcca caatgggccc cttcaacaac tgaccaccac tatgacccat   5100

attccctgca gcggccacca gagcttcagc acaaacaagc agctgaatga cgtggaagct   5160

t                                                                    5161
```

<210> SEQ ID NO 14
<211> LENGTH: 774
<212> TYPE: DNA
<213> ORGANISM: Artificial Sequence
<220> FEATURE:
<223> OTHER INFORMATION: Nucleotide sequence of the ApFATA promoter in pPB0041

<400> SEQUENCE: 14

```
ggaatcccgc ctccgagatg aagccgtggt tggcacggag gaggccgctg cgggccagag     60

tgttcttctg ctgcacgtcc tccggctttg gtggctcgct gggcttgggt gcggccatga    120

gctgcagtgc aagtgtacat ataggtcaat cttatgaccc ggcactacca atgatgatca    180

acaccgagcg gccctctgtg ttgtgcttgc ctctttacct tcactgcgta ctgctgcagg    240

agcttcatga ggatcacact gacggtcagg gggatcagca cccagtcccg gacatcccga    300

tccagtacga ggtcctggct gaccatgatg gtaggtgaag ttgggccctg ggaggagcgc    360

tagaggagcc tcggggcaaa gatcacccta ctctgacgtg gctggctcaa tcacccatcc    420

ctcccctttg aagtcggctc tcagtttgcg ttgtttcgaa atcgagccac aatcgaatat    480

acactaccta aaggctctca ccacctggcg tacctcggaa tgcccatcag cccaaacaca    540
```

```
tgagaaaagg cgcgcgcggt tcgaccccag tccgtcgatt gacgcagtgg ggagctccat    600

tctgtcagct cttgggtggc caggtcgctg acagattggc acatacagga ccctgccgac    660

ccgttcctcc agcactttgt gaatttaagc agcgcattag atcgtcgatg gcttagagaa    720

ccccgcgcct gctcccccat ctccctttca cacgtttgaa cacccggacc ggcc          774
```

```
<210> SEQ ID NO 15
<211> LENGTH: 5651
<212> TYPE: DNA
<213> ORGANISM: Artificial Sequence
<220> FEATURE:
<223> OTHER INFORMATION: Nucleotide sequence of the transforming DNA
      from pPB0118

<400> SEQUENCE: 15

aagcttagca tactcctatt ctgacaatgt cacagtcggt ctgccaggcg atagtggctt     60

tgctgtcaga ctcggccccg gactctcccc tgaactgcga cgccgggaat ctgttgagag    120

gaggcgatct gcgagggttc gcctccatgg cccgcatgta caccatcgag tatgccatga    180

agcgatgatg tctgtgaaaa tgatgttcag aattcattat atactcatgt ttttgtgtaa    240

atgctgtgtc gacttaagtt accgagctgg ctgacagaga caatcttcag gtcaaatgtt    300

ggcaccaatg atcgcgacga tcgttcaggg gttatcaagt cagatctgaa cgaaaaccag    360

aaatcaaatt tgccaaagcg catgtttgta tgtcgagaat tatcatgcgg gtgactggct    420

cgctaattct ggcatggaag gatgccacat cgaattgatc cggggagact aacacttgtc    480

agaattgcaa tgtgccatat tccagatatc ccagccggcc cttctataaa ccacctgcgg    540

gctcagatac ctacgaagag gctcagataa ctcaaggacg tgcattcgaa ttatccctgc    600

cgcgcggaaa catcagacca ggtgcggatg ctgagcgtcg agttgggtgc ttgatagacc    660

ttcaccttga tctgaggttc ccgtccccag agcactcgaa tctccggcat cttacaggca    720

aaccgcaaac agtaaataat ggcgagcacc atcaccatgg gtacccttgc agtgccccaa    780

aaactggcta ccacctaaca attctcacgc agttttatcc tctgcacttt gatgtcagct    840

ttttgattcg tctgcgtaca ttacagcgtt gagtggccag caggaaggag accgcggtcc    900

gagacgagtc tgagggcgcg ctctcgcaac ttggattccg gatttcttac cctgcatcga    960

cctcggcctg gagtcgatca gaaattgtca ttgccagatt gcctggcgag gacgggtgat   1020

atactcaagg cgttgcatcg cccacaaaac acacacttat ctgcaaggga gttactgcat   1080

caggctctgc tcaacagctc gtgacatcga tcgttcagct ccccagcagg tgcgtgtccg   1140

catggagcac ccctcccgag acacctgcgt tgggtgtcgg aggagctcac atgccaggga   1200

ggtgcccaca ttgcaccacg cgaccgcgaa ataggcagac ttcgggcatc ctgtcatcgc   1260

atgtccgctg gccgggaatc atggcctccc caccaggcgt cacgcgctgc ccacctccct   1320

ccccttgctg cgcagggcac cgcgttcctg tggagagccg accacatgtc cgccgccgcc   1380

gccgagaccg acgtgtccct gcgccgccgc tccaactccc tgaacggcaa ccacaccaac   1440

ggcgtggcca tcgacggcac cctggacaac aacaaccgcc gcgtgggcga caccaacacc   1500

cacatggaca tctccgccaa gaagaccgac aacggctacg ccaacggcgt gggcggcggc   1560

ggctggcgct ccaaggcctc cttcaccacc tggaccgccc gcgacatcgt gtacgtggtg   1620

cgctaccact ggatcccctg catgttcgcc gccggcctgc tgttcttcat gggcgtggag   1680

tacaccctgc agatgatccc cgcccgctcc gagcccttcg acctgggctt cgtggtgacc   1740

cgctccctga accgcgtgct ggcctcctcc cccgacctga acaccgtgct ggccgccctg   1800
```

```
aacaccgtgt tcgtgggcat gcagaccacc tacatcgtgt ggacctggct ggtggagggc   1860
cgcgcccgcg ccaccatcgc cgccctgttc atgttcacct gccgcggcat cctgggctac   1920
tccacccagc tgcccctgcc ccaggacttc ctgggctccg gcgtggactt ccccgtgggc   1980
aacgtgtcct tcttcctgtt cttctccggc cacgtggccg gctccatgat cgcctccctg   2040
gacatgcgcc gcatgcagcg cctgcgcctg gccatggtgt tcgacatcct gaacgtgctg   2100
cagtccatcc gcctgctggg cacccgcggc cactacacca tcgacctggc cgtgggcgtg   2160
ggcgccggca tcctgttcga ctccctggcc ggcaagtacg aggagatgat gtccaagcgc   2220
cacctgggca ccggcttctc cctgatctcc aaggactccc tggtgaactg agcggaggcc   2280
ttggaaatat tcgcgtcacg cgaggagtag gctctgctgg tcggccctgg atacgctgac   2340
tcttcaagca gtggggcacc acacccacct tttgccaagg gcaaggagtc ggaagggggc   2400
ggggctgcca tgcacccctg acgggcatgg ccgttccgcg agggcgccaa ctgcggcggc   2460
ctgcccgctg gctcgtgccc ccctacccc accattgcct ggagcgtttc catccccaaa   2520
tcacattcca tccaagttgt atcactatgc ccctttggct ctatacactc acggcctgag   2580
gtcccttctc ggccgtggcg gcacacgccc aaccccccac catactcttt ccatacactg   2640
caatgcttcg agcctgcctg ccacctgctc tgcttgtctc ccctcccttc ccttgaggtt   2700
ttccaatgca gtaagagaag tcgacgtgca tggacagatg attgagagat gagactagtc   2760
tttcttgcgc tatgacactt ccagcaaaag gtagggcggg ctgcgagacg gcttcccggc   2820
gctgcatgca acaccgatga tgcttcgacc ccccgaagct ccttcggggc tgcatgggcg   2880
ctccgatgcc gctccagggc gagcgctgtt taaatagcca ggcccccgat tgcaaagaca   2940
ttatagcgag ctaccaaagc catattcaaa cacctagatc actaccactt ctacacaggc   3000
cactcgagct tgtgatcgca ctccgctaag gggcgcctc ttcctcttcg tttcagtcac   3060
aacccgcaaa catgctgctg caggccttcc tgttcctgct ggccggcttc gccgccaaga   3120
tcagcgcctc catgacgaac gagacgtccg accgcccct ggtgcacttc accccaaca   3180
agggctggat gaacgacccc aacggcctgt ggtacgacga gaaggacgcc aagtggcacc   3240
tgtacttcca gtacaacccg aacgacaccg tctgggggac gcccttgttc tggggccacg   3300
ccacgtccga cgacctgacc aactgggagg accagcccat cgccatcgcc ccgaagcgca   3360
acgactccgg cgccttctcc ggctccatgg tggtggacta caacaacacc tccggcttct   3420
tcaacgacac catcgacccg cgccagcgct gcgtggccat ctggacctac aacaccccgg   3480
agtccgagga gcagtacatc tcctacagcc tggacggcgg ctacaccttc accgagtacc   3540
agaagaaccc cgtgctggcc gccaactcca cccagttccg cgacccgaag gtcttctggt   3600
acgagccctc ccagaagtgg atcatgaccg cggccaagtc ccaggactac aagatcgaga   3660
tctactcctc cgacgacctg aagtcctgga agctggagtc cgcgttcgcc aacgagggct   3720
tcctcggcta ccagtacgag tgccccggcc tgatcgaggt ccccaccgag caggacccca   3780
gcaagtccta ctgggtgatg ttcatctcca tcaaccccgg cgccccggcc ggcggctcct   3840
tcaaccagta cttcgtcggc agcttcaacg gcacccactt cgaggccttc gacaaccagt   3900
cccgcgtggt ggacttcggc aaggactact acgccctgca gaccttcttc aacaccgacc   3960
cgacctacgg gagcgccctg ggcatcgcgt gggcctccaa ctgggagtac tccgccttcg   4020
tgcccaccaa cccctggcgc tcctccatgt ccctcgtgcg caagttctcc ctcaacaccg   4080
agtaccaggc caacccggag acggagctga tcaacctgaa ggccgagccg atcctgaaca   4140
tcagcaacgc cggcccctgg agccggttcg ccaccaacac cacgttgacg aaggccaaca   4200
```

```
gctacaacgt cgacctgtcc aacagcaccg gcaccctgga gttcgagctg gtgtacgccg   4260

tcaacaccac ccagacgatc tccaagtccg tgttcgcgga cctctccctc tggttcaagg   4320

gcctggagga ccccgaggag tacctccgca tgggcttcga ggtgtccgcg tcctccttct   4380

tcctggaccg cgggaacagc aaggtgaagt tcgtgaagga gaacccctac ttcaccaacc   4440

gcatgagcgt gaacaaccag cccttcaaga gcgagaacga cctgtcctac tacaaggtgt   4500

acggcttgct ggaccagaac atcctggagc tgtacttcaa cgacggcgac gtcgtgtcca   4560

ccaacaccta cttcatgacc accgggaacg ccctgggctc cgtgaacatg acgacggggg   4620

tggacaacct gttctacatc gacaagttcc aggtgcgcga ggtcaagtga ttgattggaa   4680

ctcacaaagc ggcccacggc ttcgaacgtc ccgtgtcaat tgcgcggggt gtgccagagt   4740

ttctgcgcca ccgatgctca ccctaggggg ggatgccctt tgacattcat gtgtgcctgc   4800

atgcacgttt gtatcagtct caccacacct tgaagatttt tgggaggggg ggggaagtcg   4860

gaatggaaac ctcgagcaac gctacgcaac tcccttcgat ggcttcaagt acggagatgt   4920

gggcatccag gattcgcatg tgctgcttca gccctcctca tgccactagc actcattttt   4980

cgactcccgg attgccaggt tcaagggcat caaggagtcg gagatcagcc gcgccatgac   5040

ctcccgctac ttcgaggacc taaacgtcaa tgccgaggtg cttttgcata tatttacagc   5100

taattatgat gggtgtggtg cgcgatatgc ttgcaaggtc tccggtgagc taatgatcgg   5160

cacatccctt ccgcgcatcc gcaggtcgat gtcgtcattg ttggggctgg gtctgcgggc   5220

ctctcgtgcg cctatgagct gagcaagcac ccggatgtca aggtatgggc tgagcagggc   5280

acatcctcag atgatgttgc tgtaattgca attgaaactt gcggttgttc ccagcacagc   5340

ctcaatcaat catgtgtgct gcgttggaaa cgctatgata ccccagcctt caacatgggg   5400

cagggatatc gtttacacct gcttgaaccc cccgcaacag gtggccatca tcgagcaggg   5460

cgtcgcccct gggggtggag cgtggctggg gggtcagctc ttctcggcta tgtgtgtgag   5520

tctaggcacg gggacgggtg gactgaagca agggttgggc gcagggtgtt gatatccatg   5580

tgttggacat tctcgttggg aaaacaagat gtgtgtattt agtgctatct cggtggctgc   5640

attccaagct t                                                        5651
```

```
<210> SEQ ID NO 16
<211> LENGTH: 5526
<212> TYPE: DNA
<213> ORGANISM: Artificial Sequence
<220> FEATURE:
<223> OTHER INFORMATION: Nucleotide sequence of the transforming DNA
      from pPB0142

<400> SEQUENCE: 16

aagcttagca tactcctatt ctgacaatgt cacagtcggt ctgccaggcg atagtggctt     60

tgctgtcaga ctcggccccg gactctcccc tgaactgcga cgccgggaat ctgttgagag    120

gaggcgatct gcgagggttc gcctccatgg cccgcatgta caccatcgag tatgccatga    180

agcgatgatg tctgtgaaaa tgatgttcag aattcattat atactcatgt ttttgtgtaa    240

atgctgtgtc gacttaagtt accgagctgg ctgacagaga caatcttcag gtcaaatgtt    300

ggcaccaatg atcgcgacga tcgttcaggg gttatcaagt cagatctgaa cgaaaaccag    360

aaatcaaatt tgccaaagcg catgtttgta tgtcgagaat tatcatgcgg gtgactggct    420

cgctaattct ggcatggaag gatgccacat cgaattgatc cggggagact aacacttgtc    480

agaattgcaa tgtgccatat tccagatatc ccagccggcc cttctataaa ccacctgcgg    540
```

```
gctcagatac ctacgaagag gctcagataa ctcaaggacg tgcattcgaa ttatccctgc    600
cgcgcggaaa catcagacca ggtgcggatg ctgagcgtcg agttgggtgc ttgatagacc    660
ttcaccttga tctgaggttc ccgtccccag agcactcgaa tctccggcat cttacaggca    720
aaccgcaaac agtaaataat ggcgagcacc atcaccatgg gtacccttgc agtgccccaa    780
aaactggcta ccacctaaca attctcacgc agttttatcc tctgcacttt gatgtcagct    840
ttttgattcg tctgcgtaca ttacagcgtt gagtggccag caggaaggag accgcggtcc    900
gagacgagtc tgagggcgcg ctctcgcaac ttggattccg gatttcttac cctgcatcga    960
cctcggcctg gagtcgatca gaaattgtca ttgccagatt gcctggcgag gacgggtgat   1020
atactcaagg cgttgcatcg cccacaaaac acacacttat ctgcaaggga gttactgcat   1080
caggctctgc tcaacagctc gtgacatcga tcgttcagct ccccagcagg tgcgtgtccg   1140
catggagcac ccctcccgag acacctgcgt tgggtgtcgg aggagctcac atgccaggga   1200
ggtgcccaca ttgcaccacg cgaccgcgaa ataggcagac ttcgggcatc ctgtcatcgc   1260
atgtccgctg gccgggaatc atggcctccc caccaggcgt cacgcgctgc ccacctccct   1320
ccccttgctg cgcagggcac cgcgttcctg tggagagccg accacatgtc ccccccaac   1380
tccatgtccc ccgccaccaa cggctccacc aacggcgtgg ccatcaacgg cgccaagaag   1440
ctgctggact tcgacccctc cgccgccccc cccttcaaga tcgccgacat ccgcgccgcc   1500
atcccccccc actgctgggt gaagaacccc tggcgctccc tgtcctacgt gctgcgcgac   1560
ctgctggtga tcctgtcctt cgccgtggcc gccaccaagc tggactcctg gaccgtgtgg   1620
cccctgtact ggatcgccca gggcaccatg ttctgggccg tgttcgtgct gggccacgac   1680
tgcggccacg gctccttctc cgactcctgg ctgctgaaca acgtgatggg ccacatcctg   1740
cactcctcca tcctggtgcc ctaccacggc tggcgcatct cccacaagac ccaccaccag   1800
aaccacggca acgtggagaa ggacgagtcc tgggtgcccc tgcccgagaa ggtgtacaag   1860
tccctggaca ccggcaccaa gttcatgcgc ttcaccatcc ccctgcccat gttcgcctac   1920
cccatctacc tgtggcgccg ctcccccggc aagaagggct cccacttcaa cccctactcc   1980
gacctgttcg cccccaacga gcgcacctcc gtgatgatct ccaccctgtg ctggaccgcc   2040
atggccctgc tgctgtgcta ctcctccttc atctacggct tcctgcccgt gttcaagatc   2100
tacggcgtgc cctacctgat cttcgtggcc tggctggaca tggtgaccta cctgcaccac   2160
cacggctacg agcagaagct gccctggtac aggggcaagg agtggtccta cctgcgcggc   2220
ggcctgacca ccgtggaccg cgactacggc gtgatcaaca acatccacca cgacatcggc   2280
acccacgtga tccaccacct gttcccccag atgccccact accacctggt ggaggccacc   2340
caggccgcca agcacgtgct gggcaagtac taccgcgagc ccaagaagtc cggccccttc   2400
cccttccacc tgttcggcta cctggtgcgc tccctgggcg aggaccacta cgtgtccgac   2460
accggcgacg tggtgttcta ccagtccgac ccccacatcc ccaagttccc cacctccgcc   2520
accaccaagt ccaagtcctc ctgagtgatc cgggaggagg gagtgagcgg ggaagggggc   2580
agccacacgg ggcccgtctc gacctgccac ccctcccctc gtcgagccct gcccaggggg   2640
cgccgcaacg agccatgcgt gtgcatgtgt ctggagggcc cttccaccgg gcgatgtgcg   2700
agccatcctc gcctatttca acacaccgct gccggcatgc gctccactcc ccccaaaacc   2760
acctcgaccc tcccagggct cctcccccgc cccaccctgc ctgctgatat agaaaccagt   2820
gttctgtgaa cgtttgacat gctcaacgag ggtacagggg tgcaccaaca gaggaggagt   2880
```

-continued

```
ggttcacaca gtcggataca ctagtccttc ctgtcccaca atgcttggtg aatgcagtgg   2940
gttgatcacc gcggaggagc tgtggcttac tcgttctgat caagggagcc tctgcacctt   3000
aaccctgcca ggatcgaaac caaccttgtc agtcccgtgg tgggcaacat catcctcgtg   3060
aagctgattg accaggaaaa catgatgagt cggtatgagg acgagcatga gtggcccaac   3120
atcgatatga cacatcttgg agtttacggc aaatgtatca cacttccatc ctggcttgca   3180
ccacaatatt agtggacccc tccttgcagt ggcacggtga gaagctagtt tgtagtaatc   3240
ttcttaattg acgaaccaga cgtgtgtaat ggcctccttt gagtgatgga aggatggaac   3300
ctaccccccc cctccccagt actctgcggt acatccgagt aacccttcca ttgatcagcc   3360
caaacgcaat atgcaacgac tctacatacg gccaccgagt gcttattcct tcgctatcac   3420
cgcacaaaaa tcccatccgc gaactcatcc gaggtgatag attgcgatcg gggttattcg   3480
ggttaaggtg cgactaggga tccctgaatc ttttggggat ttccccgggt ctcgtcctgc   3540
atgcttatca tcagtctcgt gggttatttg gatcgctgcg catgccataa cagagcgctc   3600
ataatatttg ctgcggcggt ggtgctggca aaatcccctg cgtaccgggc gcctgtcaag   3660
ccaaccccgc cgtgcggcac tcccctgcag atccatcacc atgatcgagc aggacggcct   3720
ccacgccggc tcccccgccg cctgggtgga gcgcctgttc ggctacgact gggcccagca   3780
gaccatcggc tgctccgacg ccgccgtgtt ccgcctgtcc gcccagggcc gccccgtgct   3840
gttcgtgaag accgacctgt ccggcgccct gaacgagctg caggacgagg ccgcccgcct   3900
gtcctggctg gccaccaccg gcgtgccctg cgccgccgtg ctggacgtgg tgaccgaggc   3960
cggccgcgac tggctgctgc tgggcgaggt gcccggccag gacctgctgt cctcccacct   4020
ggcccccgcc gagaaggtgt ccatcatggc cgacgccatg cgccgcctgc acaccctgga   4080
ccccgccacc tgccccttcg accaccaggc caagcaccgc atcgagcgcg cccgcacccg   4140
catggaggcc ggcctggtgg accaggacga cctggacgag gagcaccagg gcctggcccc   4200
cgccgagctg ttcgcccgcc tgaaggcccg catgcccgac ggcgaggacc tggtggtgac   4260
ccacggcgac gcctgcctgc ccaacatcat ggtggagaac ggccgcttct ccggcttcat   4320
cgactgcggc cgcctgggcg tggccgaccg ctaccaggac atcgccctgg ccacccgcga   4380
catcgccgag gagctgggcg gcgagtgggc cgaccgcttc ctggtgctgt acggcatcgc   4440
cgcccccgac tcccagcgca tcgccttcta ccgcctgctg gacgagttct tctgagctgt   4500
tcctaggaac gtggaggagg tgcaaggagg gtgatctcac cctggtgtgt ctcttcatgg   4560
agctcagatc ttgaaaactg tgaggtgctt atccgatacc tgcttcgtgc atggcttgtg   4620
cgatatgtac acgcatttgc agattggtgg gagcagcaga ttggtgggag cagcatagag   4680
ctttagaagg ggcttaggag cgggaatgtg aaactcaggc ggttgggcca gatgagagcg   4740
caaagggatc ccaacgctac gcaactccct tcgatggctt caagtacgga gatgtgggca   4800
tccaggattc gcatgtgctg cttcagccct cctcatgcca ctagcactca tttttcgact   4860
cccggattgc caggttcaag ggcatcaagg agtcggagat cagccgcgcc atgacctccc   4920
gctacttcga ggacctaaac gtcaatgccg aggtgctttt gcatatattt acagctaatt   4980
atgatgggtg tggtgcgcga tatgcttgca aggtctccgg tgagctaatg atcggcacat   5040
cccttccgcg catccgcagg tcgatgtcgt cattgttggg gctgggtctg cgggcctctc   5100
gtgcgcctat gagctgagca agcacccgga tgtcaaggta tgggctgagc agggcacatc   5160
ctcagatgat gttgctgtaa ttgcaattga aacttgcggt tgttcccagc acagcctcaa   5220
tcaatcatgt gtgctgcgtt ggaaacgcta tgatacccca gccttcaaca tggggcaggg   5280
```

```
atatcgttta cacctgcttg aacccccgc aacaggtggc catcatcgag cagggcgtcg   5340

cccctggggg tggagcgtgg ctggggggtc agctcttctc ggctatgtgt gtgagtctag   5400

gcacggggac gggtggactg aagcaagggt tgggcgcagg gtgttgatat ccatgtgttg   5460

gacattctcg ttgggaaaac aagatgtgtg tatttagtgc tatctcggtg gctgcattcc   5520

aagctt                                                              5526
```

<210> SEQ ID NO 17
<211> LENGTH: 1380
<212> TYPE: DNA
<213> ORGANISM: Artificial Sequence
<220> FEATURE:
<223> OTHER INFORMATION: Coding sequence of KASII from A. protothecoides, optimized for translation

<400> SEQUENCE: 17

```
atggccaccg cctccctgcc cgtgcaggtg gccgtgacct ccacccactg cttcggcctg     60

cgcgagcccc gccgcaagcg ccagtgggcc cgccagaccc gctgccacgc ctccgccgcc    120

ggcaagccca agcgccgcgt ggtggtgacc ggccagggcg tggtgacctc cctgggccag    180

tccacccagc agttctacga ccagctgctg gccggcgcct ccggcatcac ccacatcgag    240

ggcttcgaca cctccgacta ctccaccaag atcgccggcg aggtgaagtc cgtggacgcc    300

gcccccctacg tggcccgcaa gtgggtgaag cgcatggacg aggtgatgaa gttcatgttc   360

gtggccggca agcaggccct ggaggacgcc ggcctgccct tcgagggccc cggcctggag    420

gacctggacc gcaagctgtg cggcatcctg atcggcaccg ccatgggcgg catgaccacc    480

ttcgcctccg gcgtggaggc cctgaccctg tccggccacc gcaagatgaa cccctcctgc    540

atccccttct ccatcggcaa catgggcggc gccatgctgg ccatggacct gggcttcatg    600

ggccccaact actccatctc caccgcctgc gccaccggca actactgcat catctccgcc    660

gccgaccaca tccgcaacgg cgacgccgtg ctgatgctgg cgggcggcgc cgacgccgcc    720

gtgatcccct ccggcatcgg cggcttcatc gcctgcaagg ccctgtcccg ccgcaacgac    780

gcccccgagc gcgcctcccg cccctgggac gccggccgcg acggcttcgt gatgggcgag    840

ggcgccggcg tgctggtgct ggaggagctg gagcacgccc gcgcccgcgg cgccaccatc    900

ctggccgagt tcatcggcgg cgcggccacc tgcgacgccc accacatgac cgagcccgag    960

ccctccggcc gcggcgtgcg cctgtgcctg gagcgcggcc tggccgccgc cggcgtggcc   1020

cccgaggagg tgacctacgt gaacgcccac ggcacctcca cccccgccgg cgacgtggcc   1080

gagttccgcg ccatccgcgc cgtgctgggc cacgacggcc tgcgcatcaa ctcctccaag   1140

ggcgccatcg gccacctgct gggcgcggcg ggcgccgtgg aggccgtggc caccatccag   1200

gccctgcgca ccggctggct gcaccccaac ctgaacctgg acgagcccga caagggcgtg   1260

gacgcctccg tgctggtggg cggcgtgaag gagcaggccg acgtgaaggt ggccctgtcc   1320

aactccttcg gcttcggcgg ccacaactcc tgcgtgctgt tccgcaagtt cgaggagtga   1380
```

<210> SEQ ID NO 18
<211> LENGTH: 459
<212> TYPE: PRT
<213> ORGANISM: Artificial Sequence
<220> FEATURE:
<223> OTHER INFORMATION: Amino acid sequence of A. protothecoides beta-ketoacyl-ACP synthase II

<400> SEQUENCE: 18

```
Met Ala Thr Ala Ser Leu Pro Val Gln Val Ala Val Thr Ser Thr His
1               5                   10                  15

Cys Phe Gly Leu Arg Glu Pro Arg Arg Lys Arg Gln Trp Ala Arg Gln
            20                  25                  30

Thr Arg Cys His Ala Ser Ala Ala Gly Lys Pro Lys Arg Arg Val Val
        35                  40                  45

Val Thr Gly Gln Gly Val Val Thr Ser Leu Gly Gln Ser Thr Gln Gln
    50                  55                  60

Phe Tyr Asp Gln Leu Leu Ala Gly Ala Ser Gly Ile Thr His Ile Glu
65                  70                  75                  80

Gly Phe Asp Thr Ser Asp Tyr Ser Thr Lys Ile Ala Gly Glu Val Lys
                85                  90                  95

Ser Val Asp Ala Ala Pro Tyr Val Ala Arg Lys Trp Val Lys Arg Met
            100                 105                 110

Asp Glu Val Met Lys Phe Met Phe Val Ala Gly Lys Gln Ala Leu Glu
        115                 120                 125

Asp Ala Gly Leu Pro Phe Glu Gly Pro Gly Leu Glu Asp Leu Asp Arg
    130                 135                 140

Lys Leu Cys Gly Ile Leu Ile Gly Thr Ala Met Gly Gly Met Thr Thr
145                 150                 155                 160

Phe Ala Ser Gly Val Glu Ala Leu Thr Leu Ser Gly His Arg Lys Met
                165                 170                 175

Asn Pro Phe Cys Ile Pro Phe Ser Ile Gly Asn Met Gly Gly Ala Met
            180                 185                 190

Leu Ala Met Asp Leu Gly Phe Met Gly Pro Asn Tyr Ser Ile Ser Thr
        195                 200                 205

Ala Cys Ala Thr Gly Asn Tyr Cys Ile Ile Ser Ala Ala Asp His Ile
    210                 215                 220

Arg Asn Gly Asp Ala Val Leu Met Leu Ala Gly Gly Ala Asp Ala Ala
225                 230                 235                 240

Val Ile Pro Ser Gly Ile Gly Gly Phe Ile Ala Cys Lys Ala Leu Ser
                245                 250                 255

Arg Arg Asn Asp Ala Pro Glu Arg Ala Ser Arg Pro Trp Asp Ala Gly
            260                 265                 270

Arg Asp Gly Phe Val Met Gly Glu Gly Ala Gly Val Leu Val Leu Glu
        275                 280                 285

Glu Leu Glu His Ala Arg Ala Arg Gly Ala Thr Ile Leu Ala Glu Phe
    290                 295                 300

Ile Gly Gly Ala Ala Thr Cys Asp Ala His His Met Thr Glu Pro Glu
305                 310                 315                 320

Pro Ser Gly Arg Gly Val Arg Leu Cys Leu Glu Arg Gly Leu Ala Ala
                325                 330                 335

Ala Gly Val Ala Pro Glu Glu Val Thr Tyr Val Asn Ala His Gly Thr
            340                 345                 350

Ser Thr Pro Ala Gly Asp Val Ala Glu Phe Arg Ala Ile Arg Ala Val
        355                 360                 365

Leu Gly His Asp Gly Leu Arg Ile Asn Ser Ser Lys Gly Ala Ile Gly
    370                 375                 380

His Leu Leu Gly Ala Ala Gly Ala Val Glu Ala Val Ala Thr Ile Gln
385                 390                 395                 400

Ala Leu Arg Thr Gly Trp Leu His Pro Asn Leu Asn Leu Asp Glu Pro
                405                 410                 415

Asp Lys Gly Val Asp Ala Ser Val Leu Val Gly Gly Val Lys Glu Gln
```

-continued

```
        420                 425                 430

Ala Asp Val Lys Val Ala Leu Ser Asn Ser Phe Gly Phe Gly Gly His
        435                 440                 445

Asn Ser Cys Val Leu Phe Arg Lys Phe Glu Glu
    450                 455
```